US012734172B2

(12) United States Patent
Chen et al.

(10) Patent No.: US 12,734,172 B2
(45) Date of Patent: Sep. 15, 2026

(54) METHOD AND COMPOSITION FOR TREATING PAIN

(71) Applicants: ACADEMIA SINICA, Taipei (TW); KAOHSIUNG MEDICAL UNIVERSITY, Kaohsiung City (TW); Ming-Che Shih, Culver City, CA (US)

(72) Inventors: Chin-Cheng Chen, Nankang (TW); Chin-Hsien Hung, Kaohsiung City (TW)

(73) Assignee: ACADEMIA SINICA (TW)

(*) Notice: Subject to any disclaimer, the term of this patent is extended or adjusted under 35 U.S.C. 154(b) by 1136 days.

(21) Appl. No.: 17/625,434

(22) PCT Filed: Jul. 10, 2020

(86) PCT No.: PCT/US2020/041488

§ 371 (c)(1),
(2) Date: Jan. 7, 2022

(87) PCT Pub. No.: WO2021/007470

PCT Pub. Date: Jan. 14, 2021

(65) Prior Publication Data

US 2022/0288075 A1 Sep. 15, 2022

Related U.S. Application Data

(60) Provisional application No. 62/872,353, filed on Jul. 10, 2019.

(51) Int. Cl.

| | |
|---|---|
| ***A61K 31/517*** | (2006.01) |
| ***A61K 49/00*** | (2006.01) |
| ***A61P 25/04*** | (2006.01) |

(52) U.S. Cl.

CPC ........ *A61K 31/517* (2013.01); *A61K 49/0008* (2013.01); *A61P 25/04* (2018.01)

(58) Field of Classification Search

CPC ... A61K 31/517; A61K 49/0008; A61P 25/04; A61P 29/00

See application file for complete search history.

(56) References Cited

U.S. PATENT DOCUMENTS

| | | | |
|---|---|---|---|
| 2005/0288255 | A1 | 12/2005 | Hui |
| 2008/0279846 | A1 | 11/2008 | Shi |
| 2008/0280829 | A1 | 11/2008 | Shi |

OTHER PUBLICATIONS

Kalinin and Holl, Expert Opin Ther Pat., 27(11):1227-1250, Epub Aug. 4, 2017 (Year: 2017).*

Nishio et al., Neuroscience, 247: 201-212, (Year: 2013).*

Ionue, M., "Lysophosphat idylcholine induces neuropathic pain through an action of autotaxin to generate lysophosphatidic acid", Neuroscience, 2008, vol. 152 pp. 296-298.

Wang, H.-Y., "Lysophosphat idylcholine causes neuropathic pain via the increase of neuronal nitric oxide synthase in the dorsal root ganglion and cuneate nucleus", Pharmacology, Biochemistry and Behavior, 2013, vol. 106, pp. 47-56.

International Search Report issued on Nov. 5, 2020, in connection with International Patent Application No. PCT/US2020/041488.

Hassett, A. L. & Clauw, D. J. Does psychological stress cause chronic pain? Psychiatr. Clin. North Am. 34, pp. 579-594, doi:10.1016/j.psc.2011.05.004 (2011).

Clauw, D. J. Fibromyalgia: an overview. Am. J. Med. 122, pp. S3-S13, doi:10.1016/j.amjmed.2009.09.006 (2009).

Kivimaki, M. et al. Work stress and incidence of newly diagnosed fibromyalgia: prospective cohort study. J. Psychosom. Res. 57, pp. 417-422, doi:10.1016/j.jpsychores.2003.10.013 (2004).

McBeth, J., Morris, S., Benjamin, S., Silman, A. J. & Macfarlane, G. J. Associations between adverse events in childhood and chronic widespread pain in adulthood: are they explained by differential recall? J. Rheumatol. 28, pp. 2305-2309 (2001).

Aaron, L. A. et al. Perceived physical and emotional trauma as precipitating events in fibromyalgia. Associations with health care seeking and disability status but not pain severity. Arthritis Rheum. 40, pp. 453-460 (1997).

Arnold, L. M. et al. Comorbidity of fibromyalgia and psychiatric disorders. J. Clin. Psychiatry 67, pp. 1219-1225 (2006).

Sluka, K. A. & Clauw, D. J. Neurobiology of fibromyalgia and chronic widespread pain. Neuroscience 338, pp. 114-129, doi:10.1016/j.neuroscience.2016.06.006 (2016).

Yunus, M. B. Central sensitivity syndromes: a new paradigm and group nosology for fibromyalgia and overlapping conditions, and the related issue of disease versus illness. Semin. Arthritis Rheum. 37, pp. 339-352, doi:10.1016/j.semarthrit.2007.09.003 (2008).

Staud, R. & Smitherman, M. L. Peripheral and central sensitization in fibromyalgia: pathogenetic role. Curr. Pain. Headache Rep. 6, pp. 259-266 (2002).

Simms, R. W. et al. Lack of association between fibromyalgia syndrome and abnormalities in muscle energy metabolism. Arthritis Rheum. 37, pp. 794-800 (1994).

Taguchi, T. et al. Peripheral and spinal mechanisms of nociception in a rat reserpine-induced pain model. Pain 156, pp. 415-427, doi:10.1097/01.j.pain.0000460334.49525.5e (2015).

Serra, J. et al. Hyperexcitable C nociceptors in fibromyalgia. Ann. Neurol. 75, pp. 196-208, doi:10.1002/ana.24065 (2014).

DeSantana, J. M., da Cruz, K. M. & Sluka, K. A. Animal models of fibromyalgia. Arthritis Res. Ther. 15, p. 222, doi:10.1186/ar4402 (2013).

Khasar, S. G., Dina, O. A., Green, P. G. & Levine, J. D. Sound stress-induced long-term enhancement of mechanical hyperalgesia in rats is maintained by sympathoadrenal catecholamines. J. Pain 10, pp. 1073-1077, doi:10.1016/j.jpain.2009.04.005 (2009).

(Continued)

*Primary Examiner* — Stacey N Macfarlane
(74) *Attorney, Agent, or Firm* — Lee & Hayes, P.C.

(57) ABSTRACT

Provided are methods and compositions for prevention or treatment of pain, e.g., stress-related pain. Also provided is a method for producing a non-human animal model for pain, the non-human animal model produced therefrom, and a method of screening an agent pharmaceutically active in prevention or treatment of pain using such non-human animal model.

5 Claims, 42 Drawing Sheets

(56) References Cited

OTHER PUBLICATIONS

Campos, A. C., Fogaca, M. V., Aguiar, D. C. & Guimaraes, F. S. Animal models of anxiety disorders and stress. Rev. Bras. Psiquiatr. 35 Suppl. 2, pp. S101-111, doi:10.1590/1516-4446-2013-1139 (2013).
Reichling, D. B. & Levine, J. D. Critical role of nociceptor plasticity in chronic pain. Trends Neurosci. 32, pp. 611-618, doi:10.1016/j.tins.2009.07.007 (2009).
Sluka, K. A. et al. Chronic hyperalgesia induced by repeated acid injections in muscle is abolished by the loss of ASIC3, but not ASIC1. Pain 106, pp. 229-239 (2003).
Nishiyori, M. et al. Permanent relief from intermittent cold stress-induced fibromyalgia-like abnormal pain by repeated intrathecal administration of antidepressants. Mol. Pain 7, p. 69, doi:10.1186/1744-8069-7-69 (2011).
Tsujino, H. et al. Activating transcription factor 3 (ATF3) induction by axotomy in sensory and motoneurons: A novel neuronal marker of nerve injury. Mol. Cell Neurosci. 15, pp. 170-182, doi:10.1006/mcne.1999.0814 (2000).
Dai, Y. et al. Phosphorylation of extracellular signal-regulated kinase in primary afferent neurons by noxious stimuli and its involvement in peripheral sensitization. J. Neurosci. 22, pp. 7737-7745 (2002).
Epel, E. S. et al. Accelerated telomere shortening in response to life stress. Proc. Natl. Acad. Sci. U.S.A. 101, pp. 17312-17315, doi:10.1073/pnas.0407162101 (2004).
Hagan, K. A., Wu, T., Rimm, E. B., Eliassen, A. H. & Okereke, O. I. Phobic Anxiety and Plasma Levels of Global Oxidative Stress in Women. Eur. J. Psychiatry 29, pp. 7-20, doi:10.4321/S0213-61632015000100001 (2015).
Irie, M., Asami, S., Ikeda, M. & Kasai, H. Depressive state relates to female oxidative DNA damage via neutrophil activation. Biochem. Biophys. Res. Commun. 311, pp. 1014-1018 (2003).
Bagis, S. et al. Free radicals and antioxidants in primary fibromyalgia: an oxidative stress disorder? Rheumatol. Int. 25, pp. 188-190, doi:10.1007/s00296-003-0427-8 (2005).
Cordero, M. D. et al. Clinical symptoms in fibromyalgia are better associated to lipid peroxidation levels in blood mononuclear cells rather than in plasma. PLoS One 6 pages, e26915, doi:10.1371/journal.pone.0026915 (2011).
Ayala, A., Munoz, M. F. & Arguelles, S. Lipid peroxidation: production, metabolism, and signaling mechanisms of malondialdehyde and 4-hydroxy-2-nonenal. Oxid. Med. Cell Longev. 2014, 31 pages, 360438, doi:10.1155/2014/360438 (2014).
Schieber, M. & Chandel, N. S. ROS function in redox signaling and oxidative stress. Curr. Biol. 24, pp. R453-462, doi:10.1016/j.cub.2014.03.034 (2014).
Caboni, P. et al. Metabolomics analysis and modeling suggest a lysophosphocholines-PAF receptor interaction in fibromyalgia. PLoS One 9, 8 pages, e107626, doi:10.1371/journal.pone.0107626 (2014).
Inoue, M. et al. Lysophosphatidylcholine induces neuropathic pain through an action of autotaxin to generate lysophosphatidic acid. Neuroscience 152, pp. 296-298, doi:10.1016/j.neuroscience.2007.12.041 (2008).
Marra, S., Ferru-Clement, R., Breuil, V., Delaunay, A. & Christin, M. Non-acidic activation of pain-related Acid-Sensing Ion Channel 3 by lipids. EMBO 35, pp. 414-428, doi:10.15252/embj.201592335 (2016).
Immke, D. C. & McCleskey, E. W. Lactate enhances the acid-sensing Na+ channel on ischemia-sensing neurons. Nat. Neurosci. 4, pp. 869-870, doi:10.1038/nn0901-869 (2001).
Choi, J. et al. Lysophosphatidylcholine is generated by spontaneous deacylation of oxidized phospholipids. Chem. Res. Toxicol. 24, pp. 111-118, doi:10.1021/tx100305b (2011).
Karabina, S. A. & Ninio, E. Plasma PAF-acetylhydrolase: an unfulfilled promise? Biochim. Biophys. Acta 1761, pp. 1351-1358, doi:10.1016/j.bbalip.2006.05.008 (2006).
Subbaiah, P. V., Chen, C. H., Bagdade, J. D. & Albers, J. J. Substrate specificity of plasma lysolecithin acyltransferase and the molecular species of lecithin formed by the reaction. J. Biol. Chem. 260, pp. 5308-5314 (1985).
Hodson, L., Skeaff, C. M. & Fielding, B. A. Fatty acid composition of adipose tissue and blood in humans and its use as a biomarker of dietary intake. Prog. Lipid Res. 47, pp. 348-380, doi:10.1016/j.plipres.2008.03.003 (2008).
Molliver, D. C. et al. ASIC3, an acid-sensing ion channel, is expressed in metaboreceptive sensory neurons. Mol. Pain 1, 35, 13 pages, doi:10.1186/1744-8069-1-35 (2005).
McIntyre, T. M., Prescott, S. M. & Stafforini, D. M. The emerging roles of PAF acetylhydrolase. J. Lipid Res. 50 Suppl., pp. S255-259, doi:10.1194/jlr.R800024-JLR200 (2009).
Chrousos, G. P. & Gold, P. W. The concepts of stress and stress system disorders. Overview of physical and behavioral homeostasis. JAMA 267, pp. 1244-1252 (1992).
Salim, S. Oxidative stress and psychological disorders. Curr. Neuropharmacol. 12, pp. 140-147, doi:10.2174/1570159X11666131120230309 (2014).
Cordero, M. D. et al. Oxidative stress and mitochondrial dysfunction in fibromyalgia. Neuro. Endocrinol. Lett. 31, pp. 169-173 (2010).
Chen, C. C. et al. A role for ASIC3 in the modulation of high-intensity pain stimuli. Proc. Natl. Acad. Sci. U.S.A. 99, pp. 8992-8997, doi:10.1073/pnas.122245999 (2002).
Singh, V. B., Corley, K. C., Phan, T. H. & Boadle-Biber, M. C. Increases in the activity of tryptophan hydroxylase from rat cortex and midbrain in response to acute or repeated sound stress are blocked by adrenalectomy and restored by dexamethasone treatment. Brain Res. 516, pp. 66-76 (1990).
Sluka, K. A., Kalra, A. & Moore, S. A. Unilateral intramuscular injections of acidic saline produce a bilateral, long-lasting hyperalgesia. Muscle Nerve 24, pp. 37-46 (2001).
Hargreaves, K., Dubner, R., Brown, F., Flores, C. & Joris, J. A new and sensitive method for measuring thermal nociception in cutaneous hyperalgesia. Pain 32, pp. 77-88 (1988).
Gregory, N. S., Brito, R. G., Fusaro, M. C. & Sluka, K. A. ASIC3 is required for development of fatigue-induced hyperalgesia. Mol. Neurobiol. 53, pp. 1020-1030, doi:10.1007/s12035-014-9055-4 (2016).
Yokoyama, T., Lisi, T. L., Moore, S. A. & Sluka, K. A. Muscle fatigue increases the probability of developing hyperalgesia in mice. J. Pain 8, pp. 692-699, doi:10.1016/j.jpain.2007.05.008 (2007).
Beiser, T., Numa, R., Kohen, R. & Yaka, R. Chronic treatment with Tempol during acquisition or withdrawal from CPP abolishes the expression of cocaine reward and diminishes oxidative damage. Sci. Rep. 7, p. 11162, doi:10.1038/s41598-017-11511-7 (2017).
Ohmichi, Y. et al. Two-week cast immobilization induced chronic widespread hyperalgesia in rats. Eur. J. Pain 16, 338-348, doi:10.1002/j. pp. 1532-2149.2011.00026.x (2012).
Li, J. et al. N-acetyl-cysteine attenuates neuropathic pain by suppressing matrix metalloproteinases. Pain 157, pp. 1711-1723, doi:10.1097/j.pain.0000000000000575 (2016).
Shi, S. Y. et al. DJ-1 links muscle ROS production with metabolic reprogramming and systemic energy homeostasis in mice. Nat. Commun. 6, p. 7415, doi:10.1038/ncomms8415 (2015).
Rammal, H., Bouayed, J., Younos, C. & Soulimani, R. The impact of high anxiety level on the oxidative status of mouse peripheral blood lymphocytes, granulocytes and monocytes. Eur. J. Pharmacol. 589, pp. 173-175, doi:10.1016/j.ejphar.2008.06.053 (2008).
Eruslanov, E. & Kusmartsev, S. Identification of ROS using oxidized DCFDA and flow-cytometry. Methods Mol. Biol. 594, pp. 57-72, doi:10.1007/978-1-60761-411-1_4 (2010).
Hu, P. & McLachlan, E. M. Selective reactions of cutaneous and muscle afferent neurons to peripheral nerve transection in rats. J. Neurosci. 23, pp. 10559-10567 (2003).
Bacskai, T., Rusznak, Z., Paxinos, G. & Watson, C. Musculotopic organization of the motor neurons supplying the mouse hindlimb muscles: a quantitative study using Fluoro-Gold retrograde tracing. Brain Struct. Funct. 219, pp. 303-321, doi:10.1007/s00429-012-0501-7 (2014).
Ho, T. J., Kuo, C. H., Wang, S. Y., Chen, G. Y. & Tseng, Y. J. True ion pick (TIPick): a denoising and peak picking algorithm to extract

(56) References Cited

OTHER PUBLICATIONS ion signals from liquid chromatography/mass spectrometry data. J. Mass Spectrom. 48, pp. 234-242, doi:10.1002/jms.3154 (2013).
Xia, J. & Wishart, D. S. Web-based inference of biological patterns, functions and pathways from metabolomic data using MetaboAnalyst. Nat. Protoc. 6, pp. 743-760, doi:10.1038/nprot.2011.319 (2011).
Caboni P. Liori B, Kumar A. et al. Metabolomics analysis and modeling suggest a lysophosphocholines-PAF receptor interaction in fibromyalgia. PLoS One. 8 pages, Sep. 19, 2014;9(9):e107626 (2014).
Tzellos T. G., Toulis K. A., Goulis D. G. et al. Gabapentin and pregabalin in the treatment of fibromyalgia: a systematic review and a meta-analysis. J. Clin. Pharm. Ther. 2010;35(6): pp. 639-656 (2010).
Arnold L. M., Clauw D. J., Wohlreich M. M., et al. Efficacy of duloxetine in patients with fibromyalgia: pooled analysis of 4 placebo-controlled clinical trials. Prim. Care Companion J. Clin. Psychiatry. 2009:11(5):pp. 237-244 (2009).
Geisser M. E., Palmer R. H., Gendreau R. M., Wang Y., Clauw D. J. A pooled analysis of 2 randomized, double-blind, placebo-controlled trials of milnacipran monotherapy in the treatment of fibromyalgia. Pain Pract. 2011;11(2):pp. 120-131 (2011).
Harris R. E. & Clauw D. J. Newer Treatments for Fibromyalgia Syndrome Ther. Clin. Risk Manag. Dec. 2008;4(6): pp. 1331-1342 (2008).
Malin K. & Littlejohn G. O. Stress modulates key psychological processes and characteristic symptoms in females with fibromyalgia. Clin. Exp. Rheumatol. Nov.-Dec. 2013; p. 31(6 Suppl. 79): S64-71. Epub. Oct. 21, 2013 (2013).
Yunus M. B. Central Sensitivity Syndromes: A new paradigm and group nosology for fibromyalgia and overlapping conditions, and the related issue of disease versus illness. Semin. Arthritis Rheum. Jun. 2008 ;37(6): pp. 339-352 (2008).
Viola-Saltzman M. & Watson N. F. et al. High prevalence of restless legs syndrome among patients with fibromyalgia: a controlled cross-sectional study. J. Clin. Sleep Med. Oct. 15, 2010; 6(5): pp. 423-427 (2010).
Hoogwout S. J. & Paananen M. V et al. Musculoskeletal pain is associated with restless legs syndrome in young adults. BMC Musculoskeletal Disorders 16 (Oct. 2015): pp. 294-294 (2015).
Zhua X. Y. & Wua T. T. Clinical features and subtypes of restless legs syndrome in Chinese population: a study of 359 patients. Sleep Medicine 59 (2019): pp. 15-23 (2019).

* cited by examiner

Ctrl
Cervical
Thoracic
Lumbar
RISS

☐ Ctrl ▨ RISS
% of cells expressing p-ERK in a given population
0
5
10
15
20
*
*
*
Cervical
Thoracic
Lumbar

METHOD AND COMPOSITION FOR TREATING PAIN

CROSS-REFERENCE TO RELATED APPLICATIONS

This application is a 35 U.S.C. 371 national phase application of PCT/US2020/041488, filed on Jul. 10, 2020, entitled METHOD AND COMPOSITION FOR TREATING PAIN, which claims priority to U.S. Provisional Application No. 62/872,353, filed on Jul. 10, 2019, entitled METHODS AND COMPOSITIONS FOR TREATING PAIN, both by Chin Cheng Chen, et al., the contents of each of which are incorporated herein by reference.

TECHNOLOGY FIELD

The present disclosure relates to methods and compositions for treatment of pain, particularly stress-related pain. The present disclosure also relates to methods for producing an animal model for generation and management of pain, an animal model produced therefrom, and a method for screening for an agent pharmaceutically active in the treatment of pain using such animal model.

BACKGROUND

Psychosocial stress is pervasive in modern societies and causatively involved in various illnesses. In addition to psychiatric disorders, stress also results in substantial somatic burden[1]. Stress-related pain has been described in this art[62, 63, 64] Fibromyalgia (FM) is commonly considered a stress-related disorder characterized by chronic non-inflammatory widespread pain[1, 2]. Although the etiology remains unknown, stress is believed to be an important trigger[1, 2]. Numerous lines of clinical evidence suggest that early adverse events precipitate later development of FM[2-5]. Moreover, high stress levels and significant psychiatric disorders are common in patients with FM[1, 6]. Although clinical evidence supports the theoretical link, the cause-effect relation remains poorly defined[1, 2, 7]. As well, the potential mechanisms underlying these psychophysiological interactions are largely unknown.

In past decades, FM has been increasingly considered a central pain disorder[2, 7, 8]. Such attribution not only arises from its distinct psychophysiological trait, but is also compelled by the lack of evidence of peripheral tissue abnormalities[7, 9]. Thus far, whether somatosensory inputs are involved in the pain development remains unclear. On the one hand, lack of detectable tissue damage does not support peripheral sensitization as the cause of hypersensitivity[9, 10]. On the other hand, lack of tissue pathology may not preclude peripheral factors from participating in nociceptive activation[7, 11]. Of note, recent clinical evidence revealed C-fiber hyperexcitability in FM, probably contributing to the pathogenesis[12]. Nonetheless, such observations still leave the unanswered question of how the aberrant excitability develops in the first place. From the psychophysiological perspective, there is also no clue about whether and how the psychological stressors interact with the somatosensory input. A previous clinical report indicated that LPC16:0 is one of the most discriminating metabolites for FM patients as compared with healthy controls by lipidomics analysis[58]. However, the role of LPC16:0 in FM pathogenesis and its algogenic effects in vivo remain undetermined.

Pregabalin, duloxetine, and milnacipran are the drugs that currently approved by the US Food and Drug Administration for FM treatment[59, 60, 61]. Although these drugs provide effects on relieving pain, their functions are limited to symptomatic treatment and the analgesic effects are transient. As well, there is no indication reported for preventive therapy.

Therefore, it is still desirable to develop a method or composition for treating or managing (e.g., preventing) stress-related pain disorders, such as FM.

SUMMARY

In this present disclosure, it is unexpectedly found that platelet-activating factor acetylhydrolase (PAF-AH), also known as lipoprotein-associated phospholipase A2 (Lp-PLA2), participates in generation of certain lysophosphatidylcholines (LPCs) that mediates stress-related pain, and a PAF-AH inhibitor is effective in alleviating the stress-related pain by inhibiting the LPC synthesis. It is also found that ROS scavengers or antioxidants are effective in blocking LPC generation by reducing production of oxidized phosphatidylcholines (PCs), and are effective in treating or preventing stress-related pain.

Therefore, the present disclosure provides an approach to treat or manage pain based on inhibition of activity of platelet-activating factor acetylhydrolase (PAF-AH) and reducing production of oxidized PCs in a subject in need thereof.

In one aspect, the present disclosure provides a method for preventing or treating pain or a related pain disorder comprising administering to a subject in need thereof an effective amount of at least one of an inhibitor of PAF-AH and an antioxidant.

The present disclosure further provides a pharmaceutical composition for use in preventing or treating pain or a related pain disorder in a subject in need thereof, comprising a therapeutically effective amount of a PAF-AH inhibitor or an antioxidant, and a pharmaceutically acceptable carrier. Also provided is a use of a PAF-AH inhibitor for manufacturing a medicament for preventing or treating pain or a related pain disorder in a subject in need thereof.

In some embodiments, the pain is stress-related pain.

In some embodiments, the pain is chronic pain, including chronic, non-inflammatory pain.

In some embodiments, the pain disorder includes fibromyalgia (FM).

In some embodiments, the pain disorder includes primary headache (migraine or tension type headache).

In some embodiments, the pain disorder includes muscular discomfort, limb soreness, lower back pain, cancer pain, arthritis pain or psychogenic pain.

In some embodiment, the muscular discomfort or the limb soreness is caused by restless leg syndrome (RLS).

In some embodiments, the pain is caused by an irritable bowel syndrome, a bladder pain syndrome or a temporomandibular disorder.

In some embodiments, the PAF-AH inhibitor or the antioxidant is administered in an amount effective in blocking development of the pain or the pain disorders. In another embodiment, the PAF-AH inhibitor or the antioxidant provide a long term anti-nociceptive effect.

In some embodiments, the PAF-AH inhibitor is a pyrimidine-based compound. Examples of such pyrimidine-based compound are as described in PCT International Patent Publication No. WO 01/060805A1, U.S. Patent Publication No. 2008/0280829, U.S. Patent Publication No. 2008/0279846, and U.S. Pat. No. 9,029,383B2, for example.

Examples of the pyrimidine-based compound as used herein include N-[2-(diethylamino)ethyl]-2-{2-[(4-fluorobenzyl)sulfanyl]-4-oxo-4,5,6,7-tetrahydro-1H-cyclopenta[d]pyrimidin-1-yl}-N-{[4'-(trifluoromethyl)biphenyl-4-yl]methyl}acetamide, having the formula as follows:

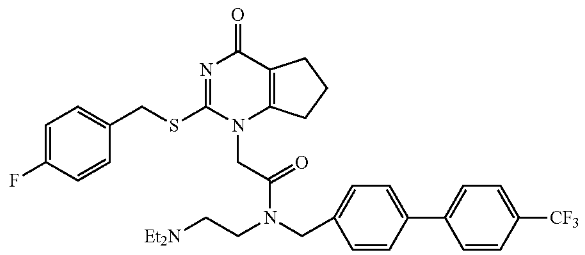

darapladib, and 2-[2-[(2,3-difluorophenyl)methylsulfanyl]-4-oxoquinolin-1-yl]-N-[1-(2-methoxyethyl)piperidin-4-yl]-N-[[4-[4-(trifluoromethyl)phenyl]phenyl]methyl]acetamide, having the formula as follows:

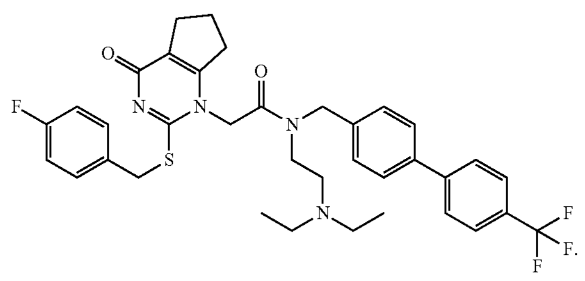 [SMILES: CCN(CC)CCN(Cc1ccc(-c2ccc(C(F)(F)F)cc2)cc1)C(=O)Cn1c(SCc2ccc(F)cc2)nc(=O)c2c1CCC2]

In some embodiments, the antioxidant is a scavenger of reactive oxygen species (ROS). Examples of antioxidants include ascorbic acid, Na-ascorbate, L-cysteine, N-acetylcysteine (NAC), glutathione (GSH), Na2-EDTA, Na2-EDTA-Ca, and sodium bisulfite.

In another aspect, the present disclosure provides a method for producing a non-human animal model for pain, comprising the step of (i) applying repeated sound stimuli, or (ii) administering lysophosphatidylcholine (LPC) 16:0, to a non-human animal, thereby resulting in development of pain behavior.

Also provided is a non-human animal model for pain prepared by the method as described herein.

Further provided is a method of screening an agent effective in treating pan, comprising the steps of:

(i) administering a test agent to an animal model as described herein; and (ii) measuring whether at least one of the pain behaviors is reduced or alleviated, wherein reduction or alleviation of at least one of the pain behaviors in the animal model via administration of the test agent indicates that the test agent is a candidate analgesic agent useful for treating pain.

The details of one or more embodiments of the disclosure are set forth in the description below. Other features or advantages of the present disclosure will be apparent from the following descriptions of several embodiments, and also from the appended claims.

BRIEF DESCRIPTION OF THE DRAWINGS

To illustrate the disclosure, the embodiments are illustrated in the following. However, it should be understood that the disclosure is not limited to the embodiments shown.

In the drawings:

FIG. 1A shows the schematic representation of the RISS protocol: mice were placed in a bedding cage under a speaker emitting continuous pure tone stimuli with randomly varied frequencies (5 to 19 kHz), duration (5 or 10 sec), and amplitude (0 to 100 dB) for 30 min as a set. In the original sound stress (SS) protocol, the stimulus set was given once a day on days 1, 3, and 4. The RISS protocol intensified the stimulus intensity by repeating the stimulus set every 3 hours for 6 times overnight (from 16:00 to 10:00) on the same day. FIG. 1B shows the sensory- and anxiety-related behavior assessed in mice after SS and RISS exposure. Upper left: mechanical hyperalgesia measured by von Frey test. Upper right: muscle hyperalgesia measured as muscle withdrawal threshold. Lower left and right: anxiety state measured as duration of time spent in the center area of the open field test and in the open arm of the plus maze test (n=6). FIG. 1C shows the time course of pain behaviors after RISS. Left: mechanical hyperalgesia. Middle: thermal hyperalgesia measured by Hargreaves test. Right: muscle hyperalgesia (n=6). FIG. 1D shows the time course of fatigue-like behaviors after RISS measured by grip force test (n=6). FIG. 1E shows the hyperalgesic behavior assessed in mice of both genders at day 0 after RISS. Left: mechanical hyperalgesia measured by von Frey test. Right: muscle hyperalgesia measured as muscle withdrawal threshold (n=6). FIG. 1F shows the time course of pain behaviors assessed by von Frey test in female and male mice after RISS (n=6 per group). FIG. 1G shows the analgesic effect of pregabalin, morphine, and diclofenac on RISS-induced pain (n=6 per group). Upper panel: mechanical hyperalgesia. Middle: muscle hyperalgesia. Lower: thermal hyperalgesia. Data are mean±SEM. B: basal status. Ns: non-significant. Ctrl: control. * $p<0.05$,  $p<0.01$, * $p<0.001$ compared with B (FIGS. 1B and 1E) or Ctrl (FIGS. 1C, 1D and 1F). #$p<0.05$, ##$p<0.01$, ###$p<0.001$ compared with RISS-Vehicle injection groups (FIG. 1G). ++$p<0.01$ compared with Ctrl-Vehicle injection groups (FIG. 1G) (All 2-way ANOVA).

FIG. 2A shows representative imaging of pERK expression of L4 DRG neurons in control, SS, and RISS mice. FIG. 2B shows the quantitative analysis of expression of pERK in L4 DRG neurons. FIG. 2C shows the representative imaging of pERK expression of cervical (C8), thoracic (T12) and lumbar (L4) DRG neurons in control and RISS mice, respectively. Scale bar: 100 μm. FIG. 2D shows the quantification of pERK expression in control and RISS mice (n=3 mice per group). FIG. 2E shows the quantitative analysis of pERK colocalization with sensory neurons markers. Left: percentage of pERK-positive DRG neurons immunostained for substance P (SP), calcitonin gene-related peptide (CGRP), isolectin B4 (IB4) and neurofilament 200 (N52). Right: percentage of CGRP-, SP-, IB4-, and N52-positive neurons expressing pERK. FIG. 2F shows the representative double immunofluorescence staining showing colocalization of pERK with SP, CGRP, IB4, and N52 in L4 DRG of RISS mice. Arrowheads indicate examples of colocalized neuronal profiles. Scale bar: 100 μm. FIG. 2G shows the magnified images of FIG. 2F. Scale bar: 25 μm. Ctrl: control. Data are mean±SEM (n=3 mice per group). ** $p<0.01$ compared to controls (Mann-Whitney or Kruskal-Wallis test).

FIG. 3A shows the serum malondialdehyde (MDA) level assayed by the thiobarbituric acid reactive substances method in RISS mice compared with controls (n=6 per group; ANOVA). The day after completing the RISS stimuli is called P0; the post-stress day 1, P1; and so on. FIG. 3O shows the effect of NAC and Tempol on serum LPC16:0 level in RISS mice as assessed by relative quantitative analysis with liquid chromatography-mass spectrometry at P0 (n=6) (left graph), and the effect of NAC and Tempol on the RISS-induced chronic hyperalgesia (n=6) (right graph) (Both ANOVA). B: basal status. Ctrl: control. i.m.: intramuscular injection. i.p.: intraperitoneal injection. LPC: lysophosphatidylcholine. BW: bodyweight. NAC: N-acetylcysteine. Data are mean±SEM. * p<0.05,  p<0.01, * p<0.001 compared to Ctrl or B. #p<0.05, ##p<0.01, ###p<0.001 compared with RISS-Vehicle injection groups.

FIG. 4A shows psychological stress levels in FM patients (n=31) and healthy controls (HCs) (n=30) as assessed by the Perceived Stress Scale-10 (PSS-10) (unpaired t test) (left graph), and plasma malondialdehyde (MDA) level assayed by the thiobarbituric acid reactive substances (TBARS) method in FM patients and HCs (unpaired t test) (right graph). FIG. 4B shows the score plot of principal component analysis based on lipidomic analysis of plasma from FM patients and HCs. FIG. 4C shows the score plot of orthogonal partial least squares discriminant analysis (OPLS-DA) distinguishing FM and HC groups based on plasma lipidomic profiling ($R^2Y=0.593$, $Q^2=0.149$). FIG. 4D shows the S-plot of OPLS-DA and the differentiating metabolites identified for FM (marked as darker circles). FIG. 4E shows the box-and-whisker plots of discriminative lipids for FM and their fold change in peak intensity (Mann-Whitney test). Whiskers represent minimum and maximum values. Data for the remaining lipids selected by OPLS-DA are in FIGS. 9B to 9E. FIG. 4F shows the correlation matrix between lipid expression of peak intensity and FM symptom measures (VRS and FIQR scores) in the HC and FM groups (Spearman's rank correlation test). Spearman correlation coefficients are labelled in each cell. VRS: verbal rating scale of pain. FIQR: the Revised FM Impact Questionnaire. Data are mean±SEM. * p<0.05,  p<0.01, * p<0.001 compared to HC.

FIG. 5A show the subgrouping FM patients based on disease severity by cluster analysis. Patients were classified into two subgroups (Clusters 1 and 2) based on FIQR score with K-means cluster analysis. FIQR scores were higher in Cluster 2 (n=12) than Cluster 1 (n=19). Patients of Cluster 2 were thus designated as the group with severe symptoms (FM-S), and those of Cluster 1 with mild symptoms (FM-M). FIG. 5B shows the pain intensity assessed by verbal rating scale (VRS; 0-10) among the HC (n=30), FM-M (n=19) and FM-S (n=12) groups (left graph), and extent of pain diffuseness assessed by widespread pain index (WPI; 0-19) (right graph) (ANOVA). FIG. 5C shows the psychological stress levels among HC, FM-M and FM-S groups as assessed by the Perceived Stress Scale10 (PSS-10) (ANOVA) (left graph) and plasma malondialdehyde (MDA) level assayed by the thiobarbituric acid reactive substances (TBARS) method (ANOVA) (right graph). FIG. 5D shows the box-and-whisker plots of peak intensity and fold change of lipid expression in the FM-M and FM-S subgroups versus HCs (Mann-Whitney test). FIG. 5E shows the correlation matrix between lipid expression of peak intensity and clinical symptom measures (VRS and FIQR scores) (Spearman's rank correlation test). Spearman correlation coefficients are labelled in each cell. FIG. 5F shows the schematic presentation of the mechanisms of repeated and intermittent sound stress (RISS)-induced chronic hyperalgesia. FIQR: the Revised Fibromyalgia Impact Questionnaire. WBC: white blood cell. ROS: reactive oxygen species. PCs: phosphatidylcholines.

Ox-PCs: oxidized phosphatidylcholines. Data are mean±SEM. * p<0.05,  p<0.01, * p<0.001 compared to HC (FIGS. 5B to 5D) or with significant relevance (FIG. 5E). #p<0.05, ###p<0.001 comparing FM-S with FM-M.

Figure 6A:
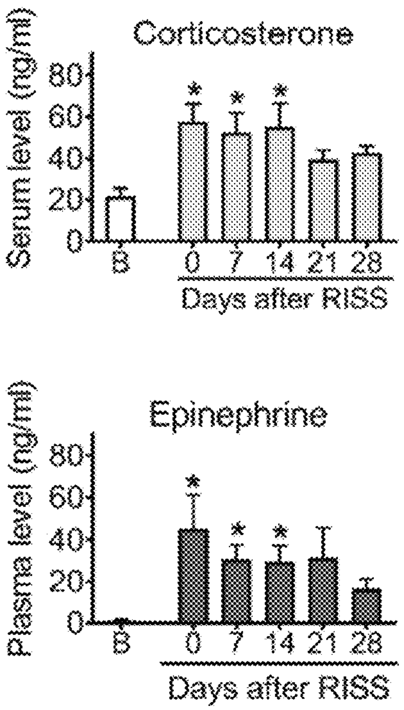
Figure 6B:
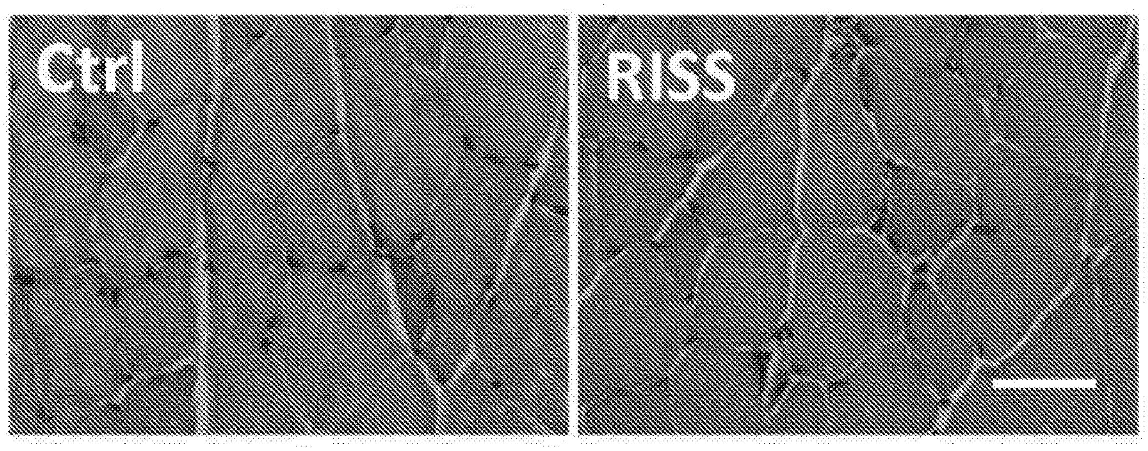
Figure 6C:
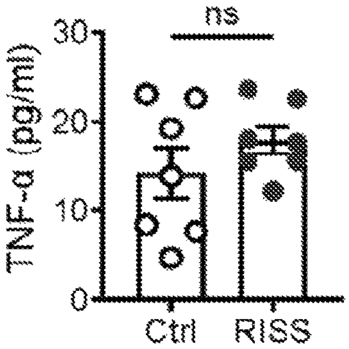
Figure 6D:
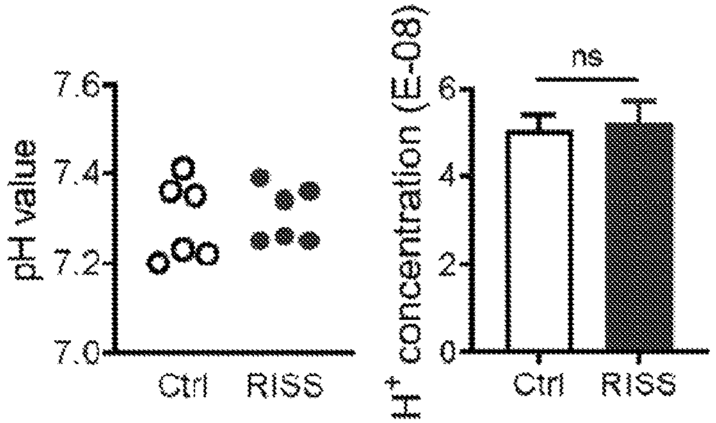
Figure 6E:
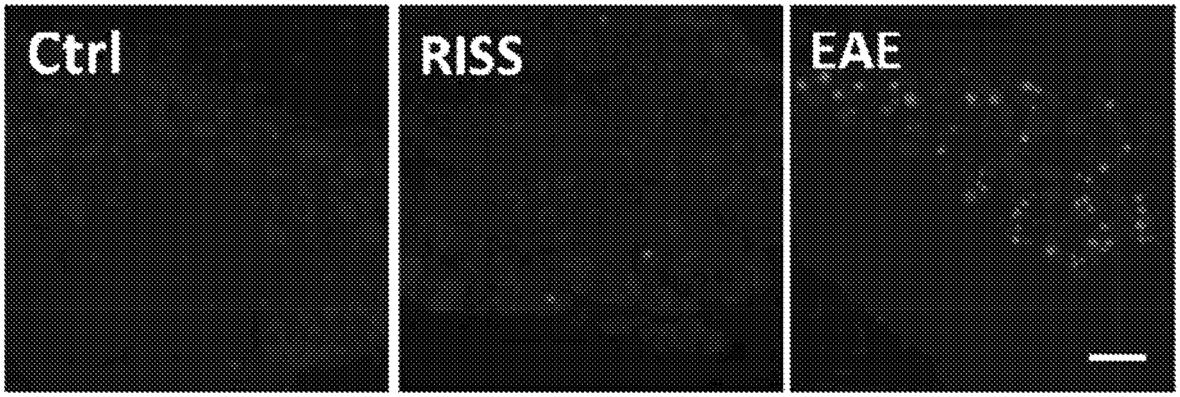
Figure 6F:
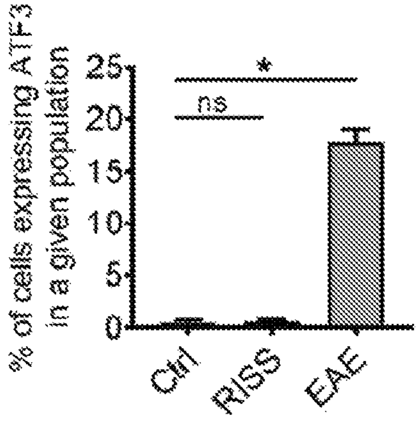

FIGS. 6A to 6F show the effects of RISS on stress hormones, biochemistry and histopathology in mice. FIG. 6A shows the time course of RISS effect on corticosterone and epinephrine levels (n=5 per group). B: baseline. * p<0.05 compared to baseline (Kruskal-Wallis test). FIG. 6B shows the gastrocnemius muscle sections with H&E staining from control and RISS mice. Scale bar: 20 μm. FIG. 6C shows the serum levels of tumor necrosis factor-alpha (TNF-α) in RISS mice compared with controls (n=7 per group; MannWhitney test). FIG. 6D shows the pH values (left) and hydrogen concentration converted from pH values (right) in muscle tissue of RISS mice at P0 as compared with control mice (n=6 per group; Mann-Whitney test). FIG. 6E shows the representative imaging of ATF-3 expression of L4 DRG neurons in control, RISS, and positive control (experimental autoimmune encephalomyelitis; EAE) mice at post-RISS day 0. Scale bar: 100 μm. FIG. 6F shows the quantitative analysis of ATF-3 expression in control, RISS and EAE mice (n=3 mice per group; Kruskal-Wallis test). Ctrl: control. Ns: non-significant. ATF-3: Activating transcription factor 3. Data are mean±SEM. * p<0.05 compared to control mice.

Figure 7A:
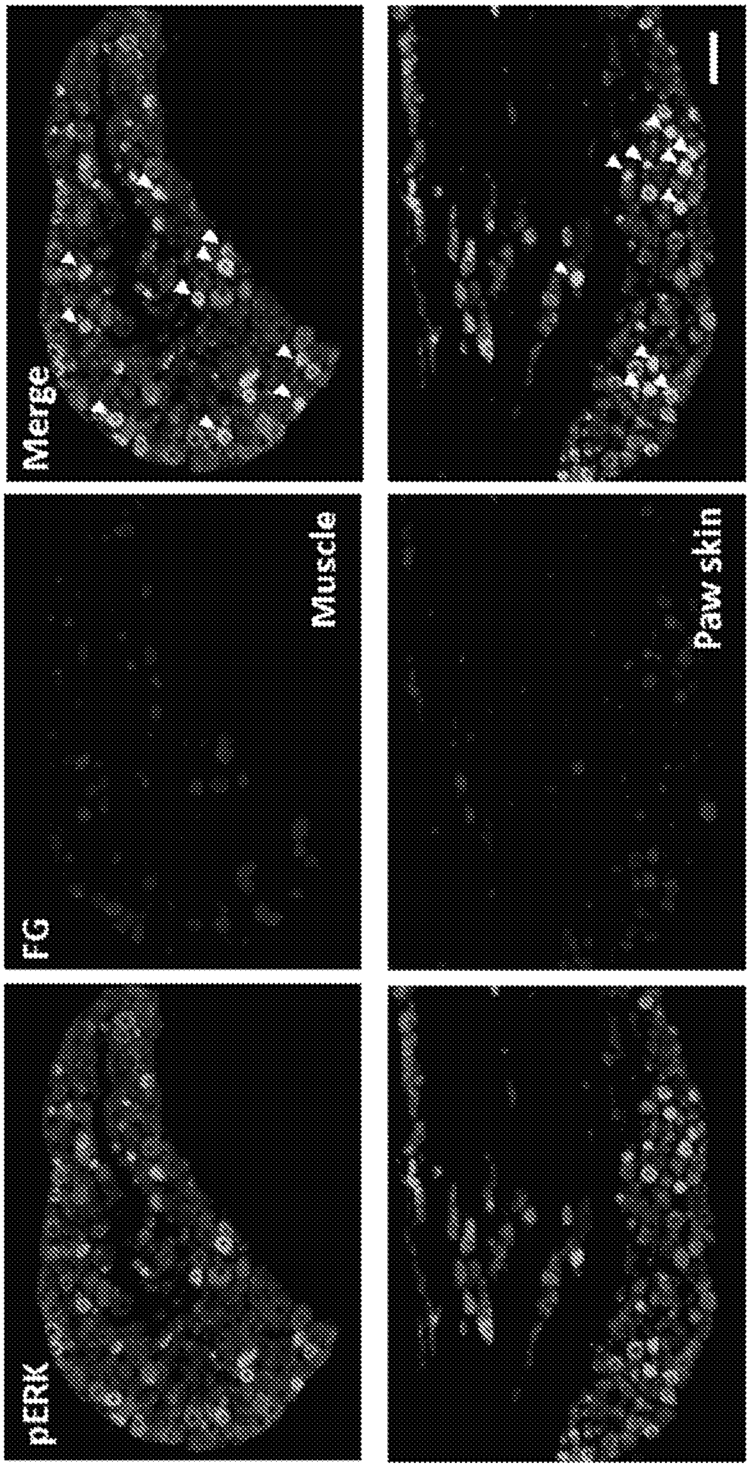
Figure 7B:
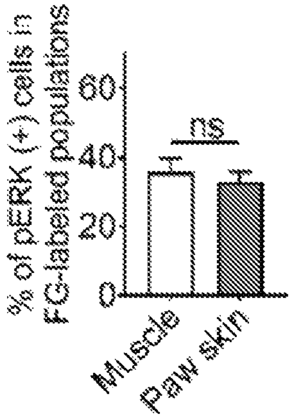
Figure 7C:
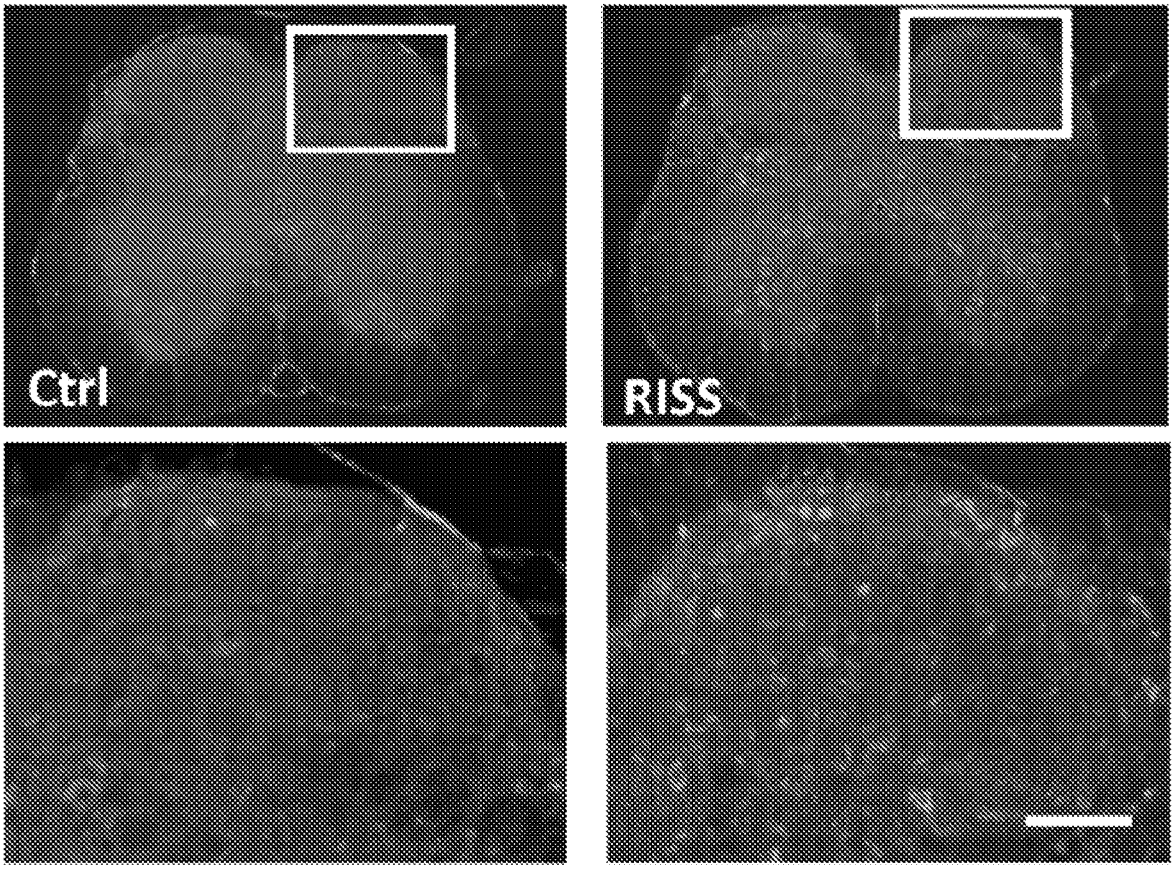
Figure 7D:
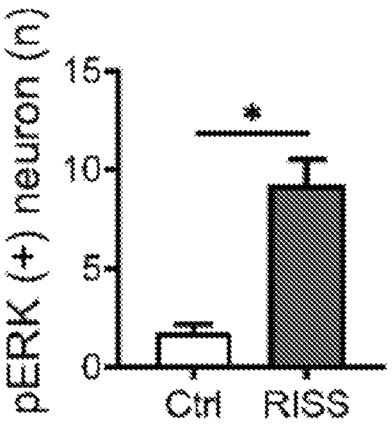
Figure 7E:
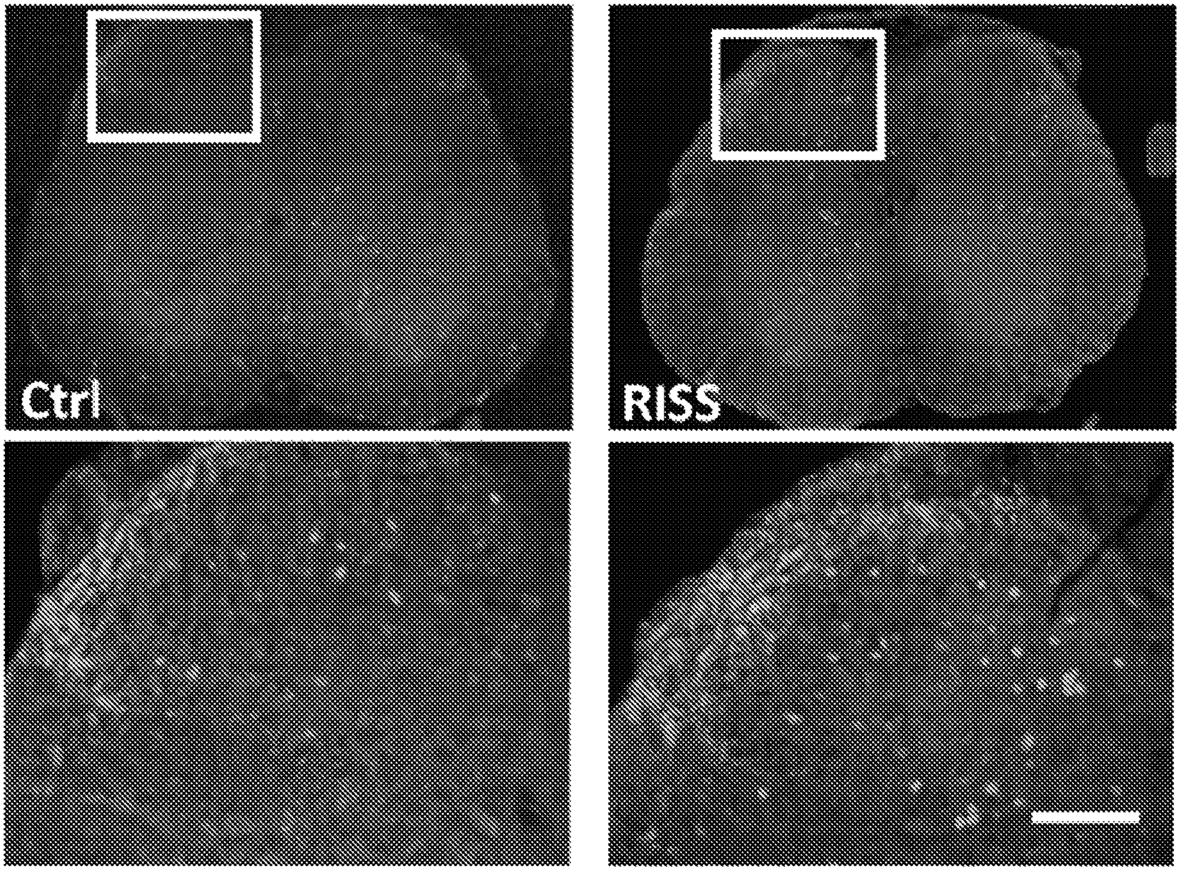
Figure 7F:
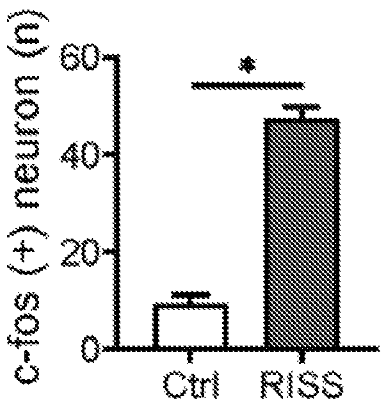

FIGS. 7A to 7F show the immunoreactivity of PERK expression in the DRG neurons and spinal cord at post-RISS day 0. FIG. 7A shows the representative imaging of double immunofluorescence staining of L4 DRG showing colocalization of pERK positive neurons with muscle (upper) and paw-skin (lower) afferent neurons retrogradely labeled with Fluoro-Gold (FG). Arrowheads indicate examples of colocalized neuronal profiles. Scale bar: 100 μm. FIG. 7B shows the quantitative analysis of pERK colocalizing with muscle and paw skin afferent neurons (n=3 mice per group test). FIG. 7C shows the representative imaging of pERK expression of spinal cord in control and RISS mice at the L4 segments at day 0. Lower photographs shows the magnified images of the rectangle region in the upper photographs. Scale bar: 50 μm. FIG. 7D shows the quantification of pERK expression in the dorsal horn area of control and RISS mice (n=3 mice per group). FIG. 7E shows the representative imaging of c-fos expression of spinal cord in control and RISS mice at the L4 segments at day 0. Lower photographs shows the magnified images of the rectangle region in the upper photographs. Scale bar: 50 μm. FIG. 7F shows the quantification of c-fos expression in the dorsal horn area (n=3 mice per group). Ns: nonsignificant. Ctrl: control. N: number. Data are mean±SEM. * p<0.05 compared to control mice (All Mann-Whitney test).

Figure 8A:
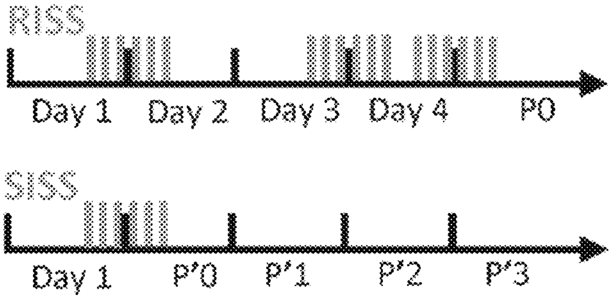
Figure 8B:
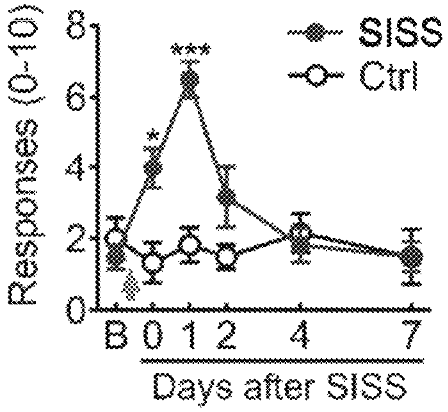
Figure 8C:
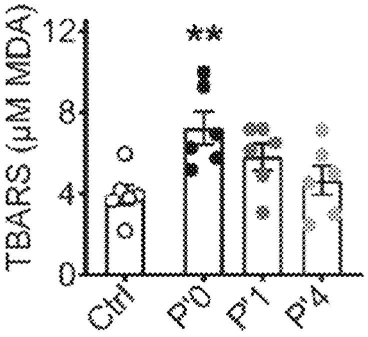
Figure 8D:
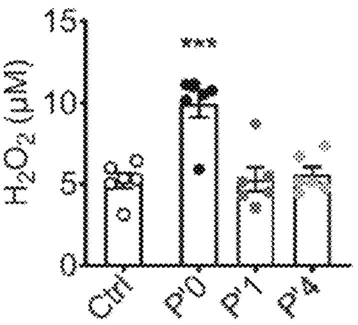
Figure 8E:
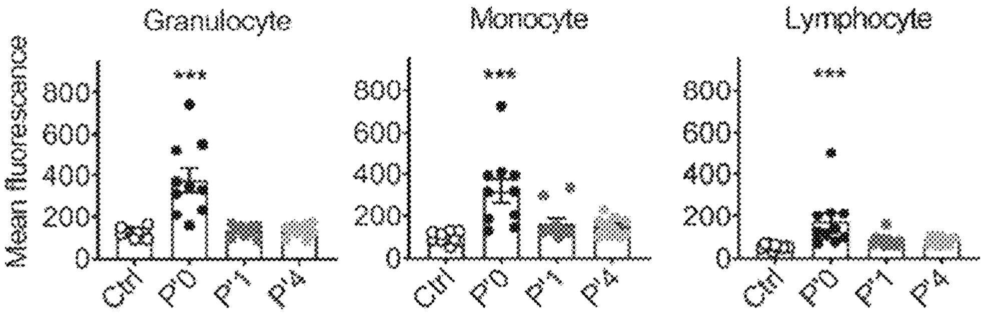

FIGS. 8A to 8E show the effect of single-day stimulus of intermittent sound stress (SISS) on oxidative status and pain behaviors. FIG. 8A shows the schematic representation of the RISS and SISS protocol. The day after completing the SISS stimuli is called P'0; the post-stress day 1, P'1; and so on. FIG. 8B shows the sensory behavioral assessment in mice after SISS exposure (n=6). Arrow: SISS. FIG. 8C shows the effect of SISS on oxidative stress in terms of the serum malondialdehyde (MDA, serum MDA level was assayed by the thiobarbituric acid reactive substance method, n=6 per group) and FIG. 8D shows the effect of SISS on oxidative stress in terms of the $H_2O_2$ levels, respectively, as compared to controls. FIG. 8E shows the effect of SISS on oxidative status of blood granulocytes, monocytes and lymphocytes, respectively. Intracellular ROS levels were measured by fluorescence intensity with CM-$H_2$DCFDA staining using flow cytometry (n=10 to 11 per group). Ctrl: control. Data are mean±SEM. * p<0.05,  p<0.01, * p<0.001 compared to controls (All ANOVA).

Figure 9A:
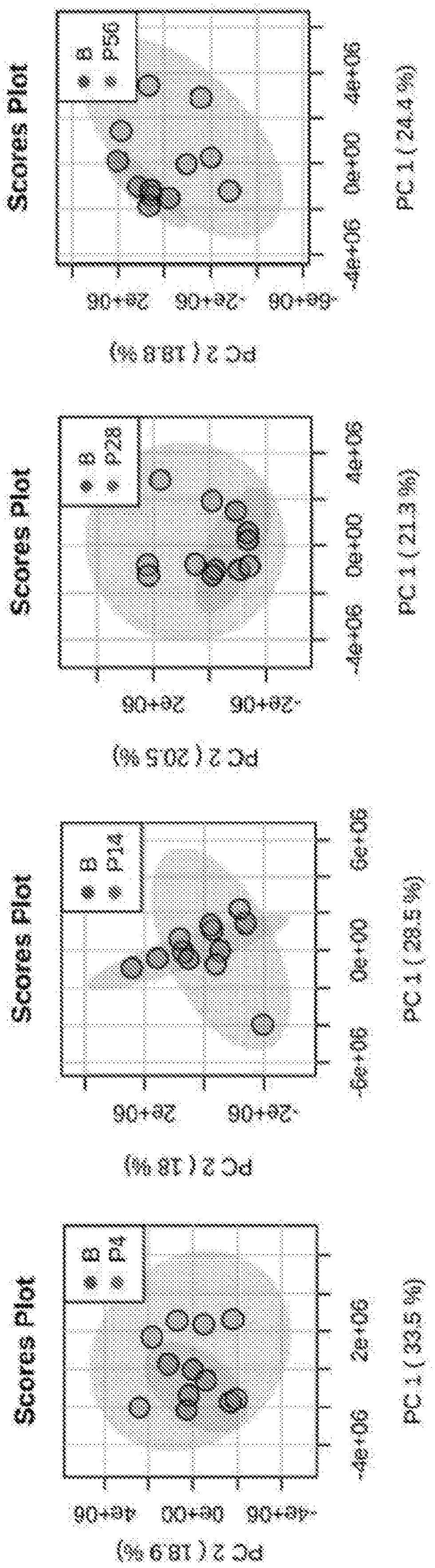
Figure 9B:
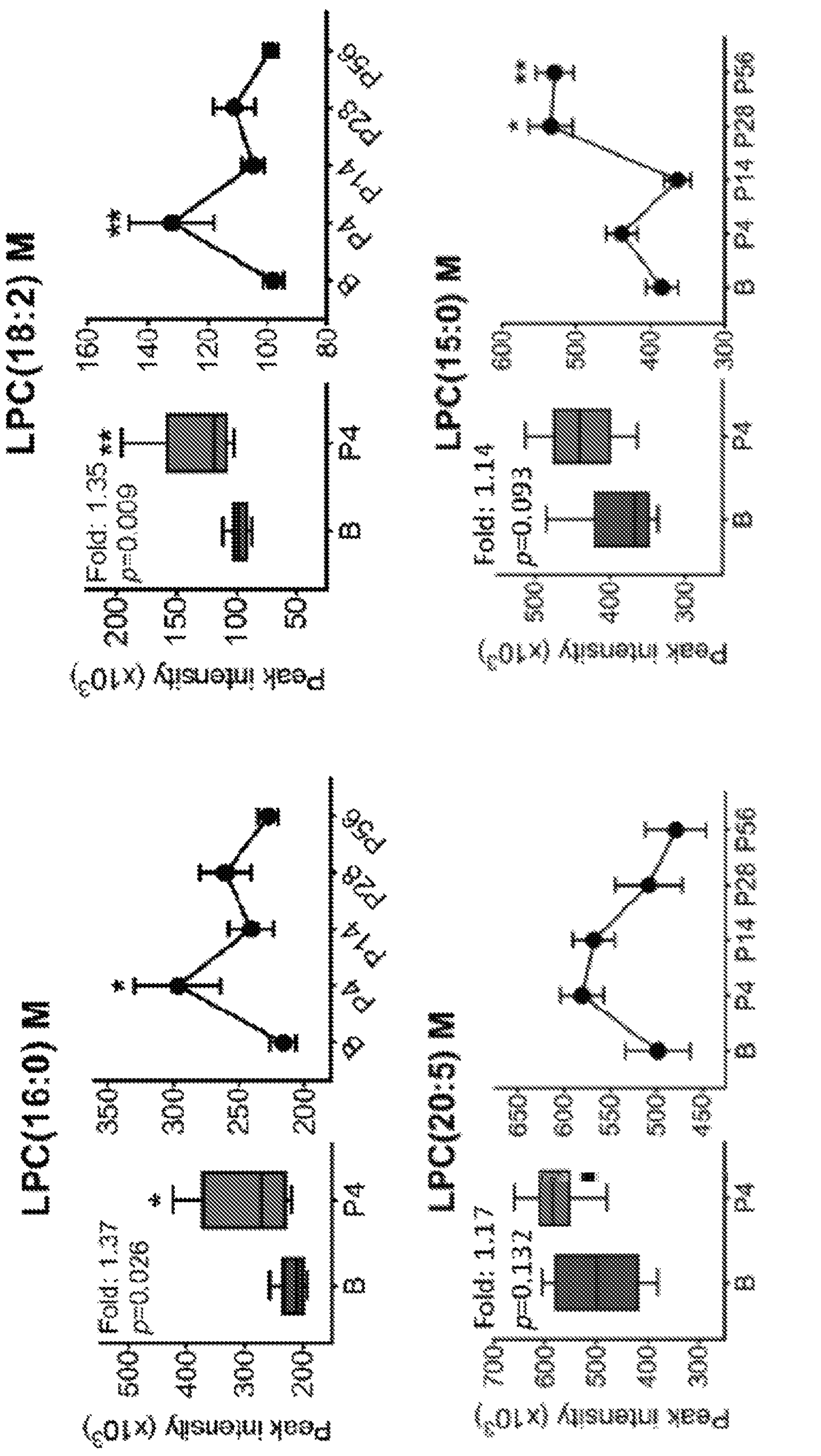
Figure 9C:
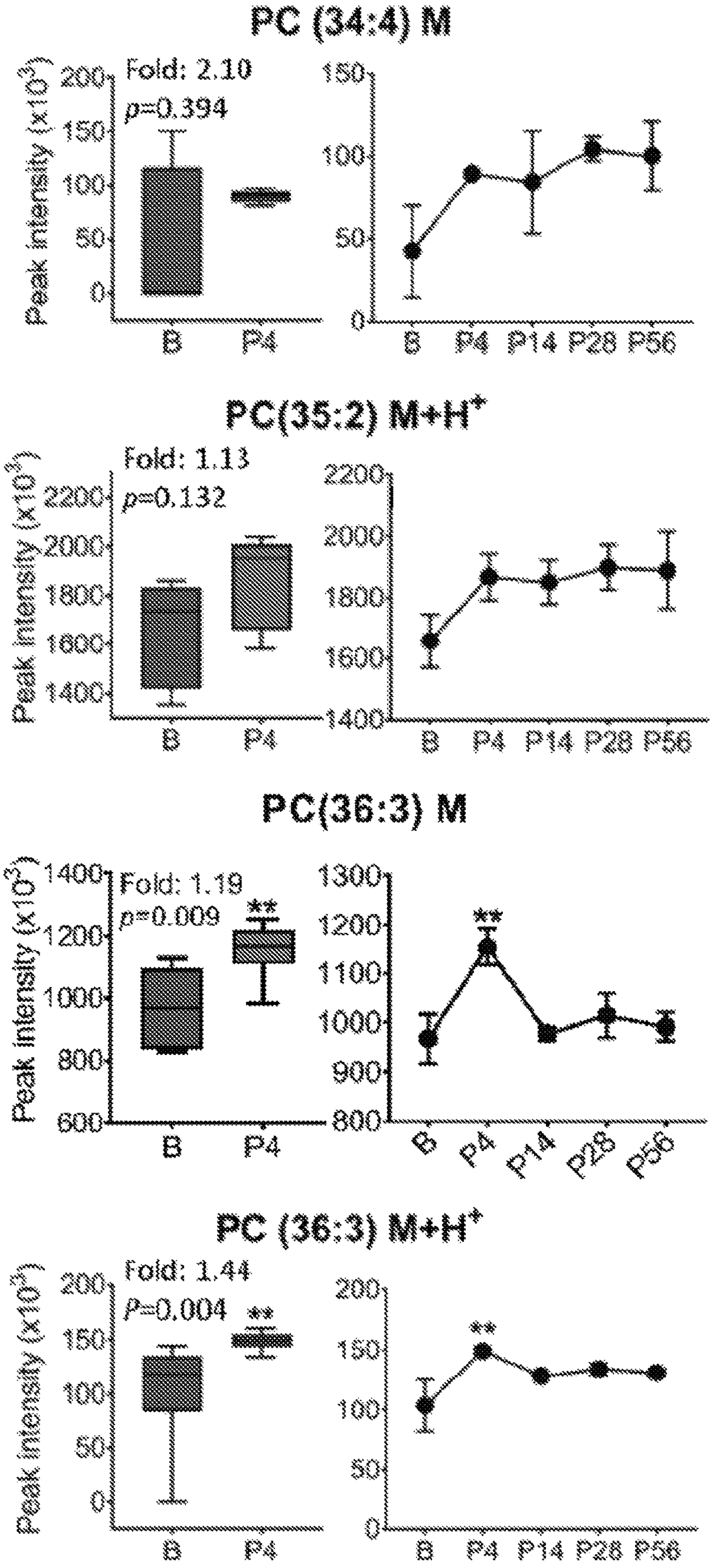
Figure 9D:
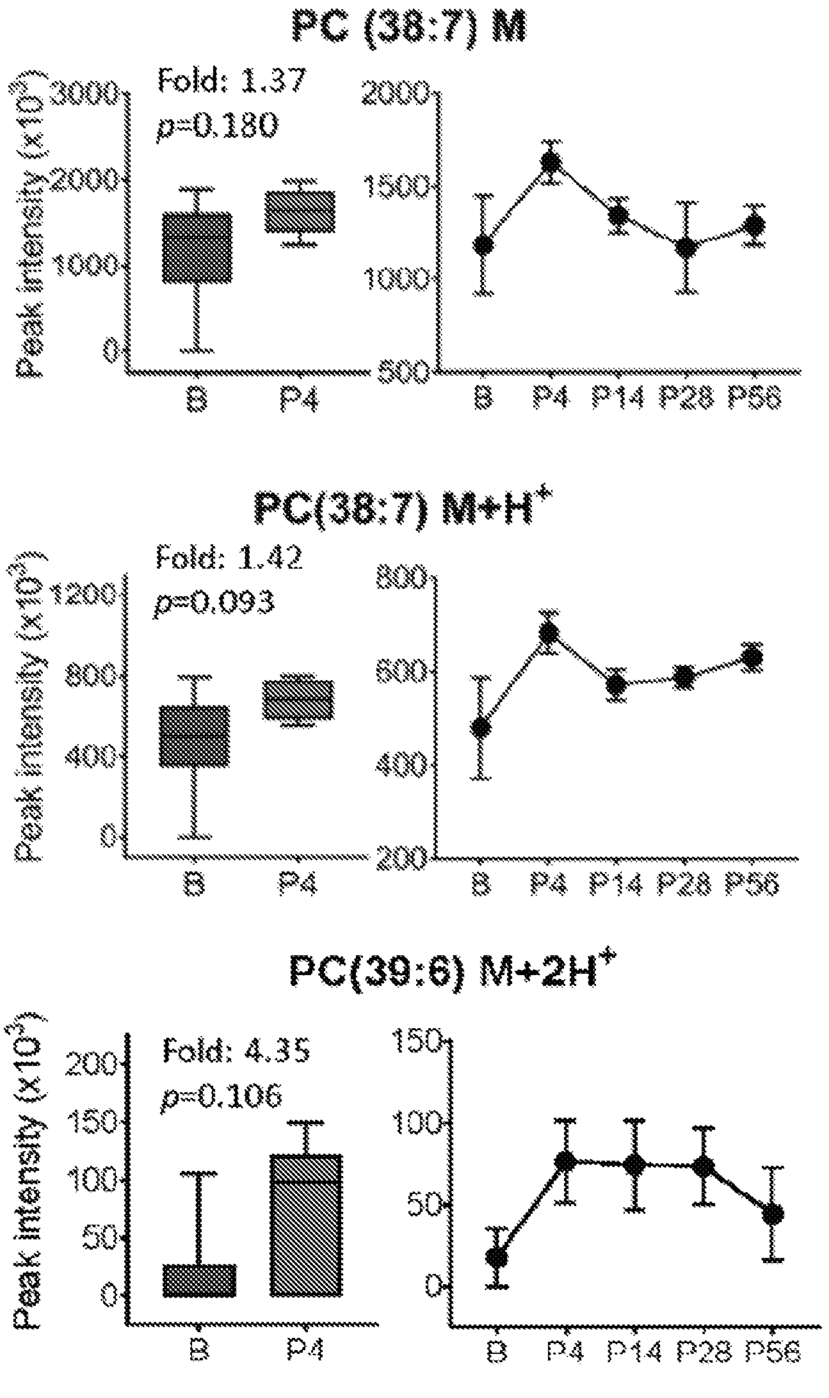
Figure 9E:
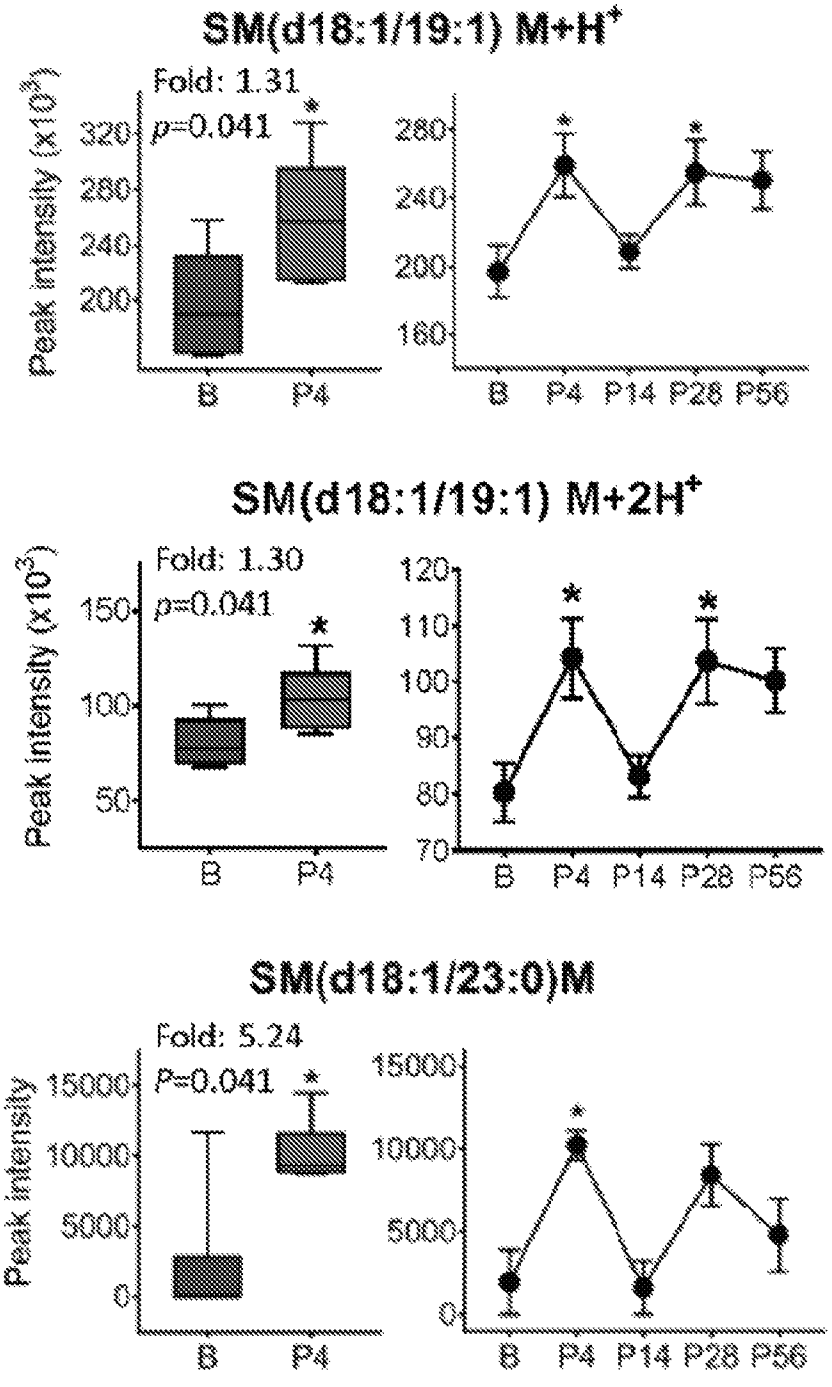
Figure 9F:
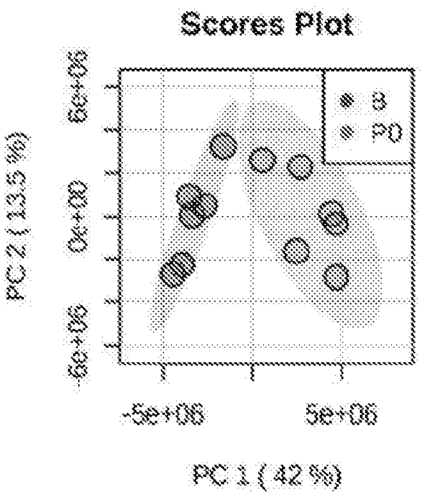
Figure 9G:
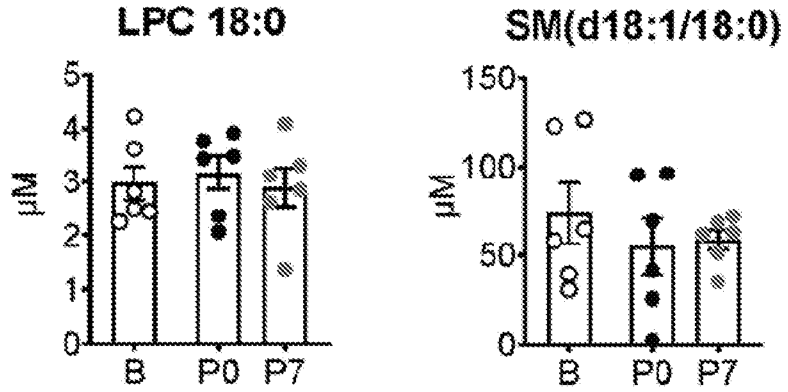

FIGS. 9A to 9G show the lipidomics analysis of RISS mice. FIG. 9A shows the score plot of PCA based on lipidomic profiling of serum from RISS mice at different times compared to the basal (B) group: acute (P4), subacute (P14), chronic (P28), and recovery (P56) (from left to right). Darker circles represent distribution of the basal group, and lighter circles represent RISS groups at each time. FIGS. 9B to 9E show the fold change analysis of the discriminative lipids (LPC in FIG. 9B, PC in FIGS. 9C and 9D, and SM in FIG. 9E) for P4 selected by OPLS-DA and their variation trends in peak intensity from P4 to P56 (n=6 per group). For each lipid, left graph shows the box-and-whisker plots of identified lipids at basal status and P4 (whiskers represent minimum and maximum values), and right graph shows the changes in peak intensity from P4 to P56 compared to basal status (Mann-Whitney test). FIG. 9F shows the score plot of PCA based on lipidomic analysis of serum from RISS mice at P0 compared to the basal group. FIG. 9G shows the quantitative profiling of LPC18:0 and SM(d18:1/18:0) at P0 (n=6 per group; ANOVA). Serum levels were measured by selective reaction monitoring triple quadrupole MS. PCA: principal component analysis. B: basal. LPC: lysophosphatidylcholine. PC: phosphatidylcholine. SM: sphingomyelin. * p<0.05, ** p<0.01, indicates statistically significant difference between basal status and the RISS mice at different times (Mann-Whitney test).

Figure 10A:
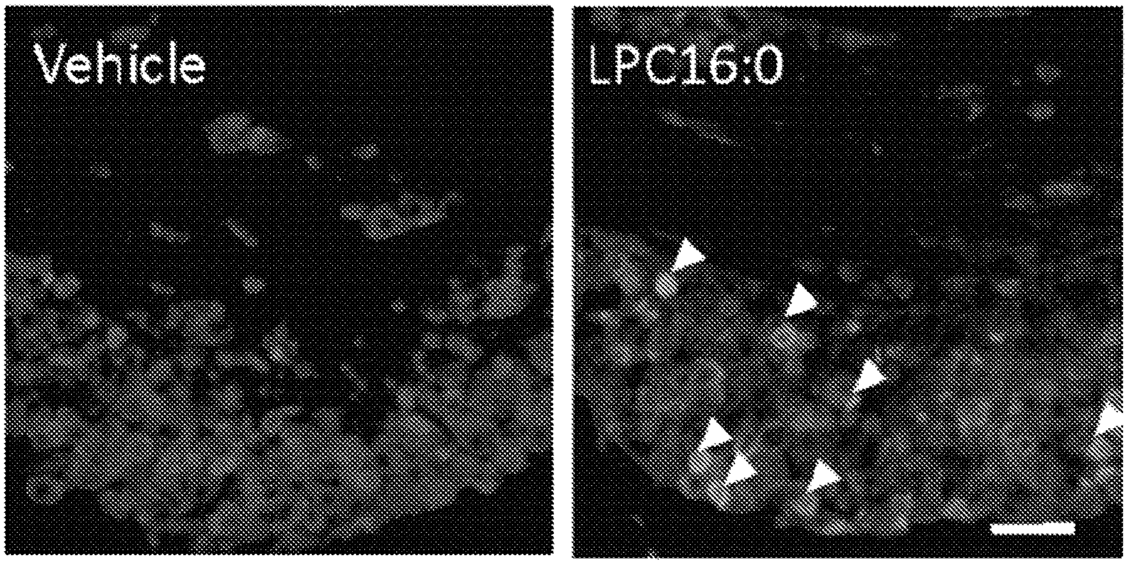
Figure 10B:
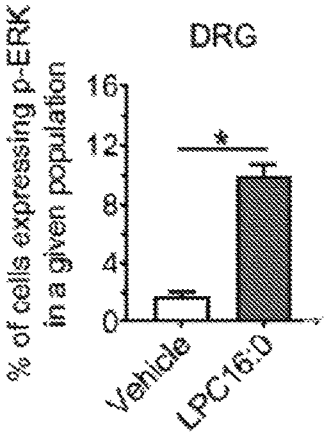
Figure 10C:
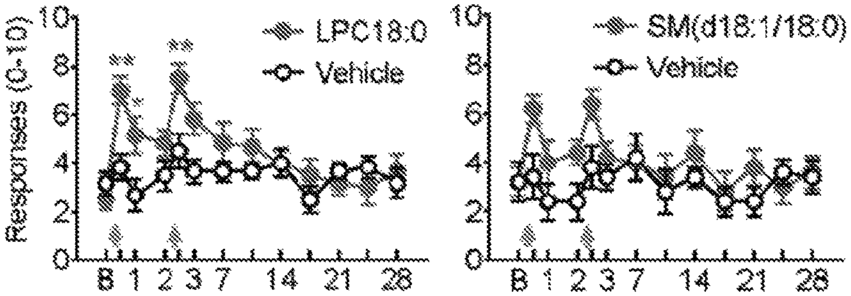
Figure 10D:
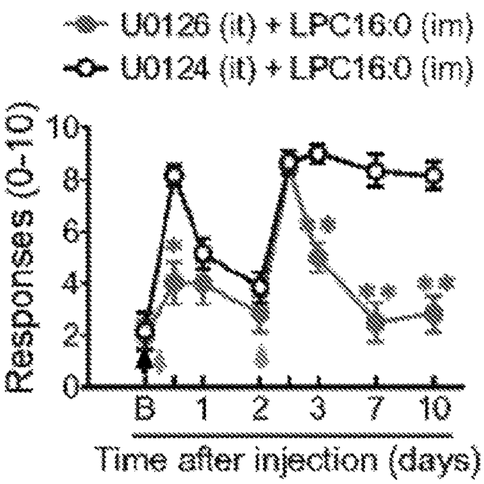
Figure 10E:
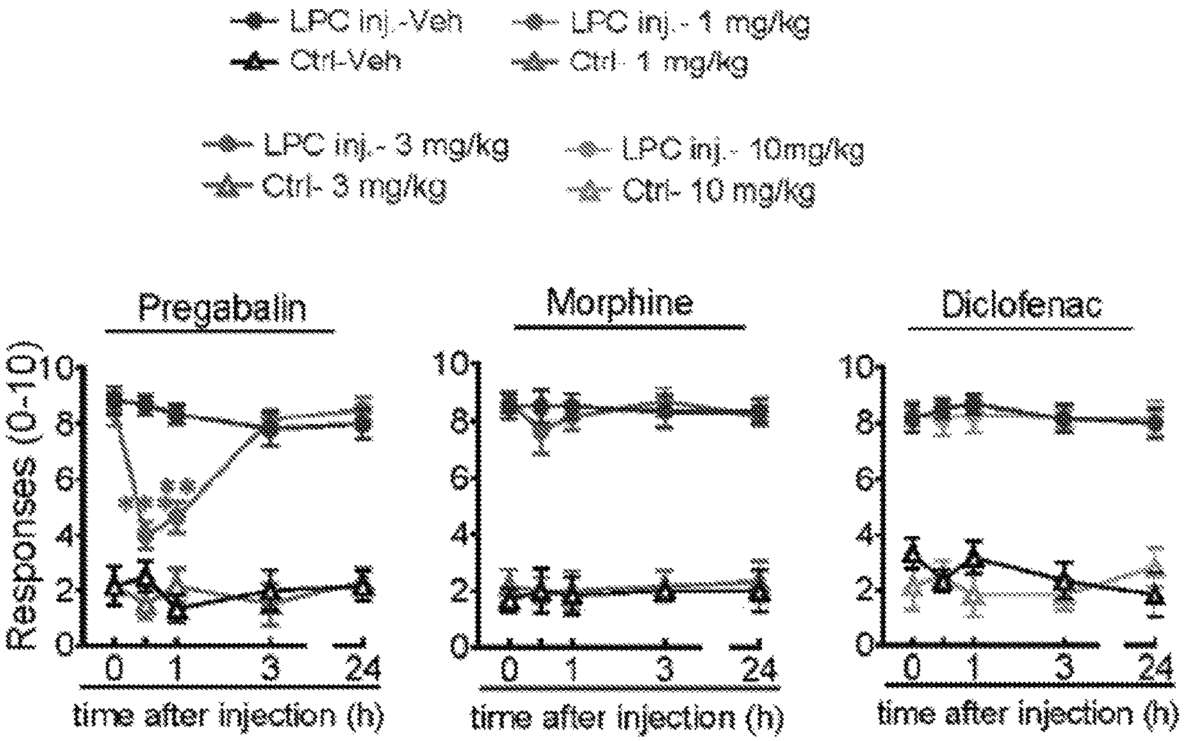
Figure 10F:
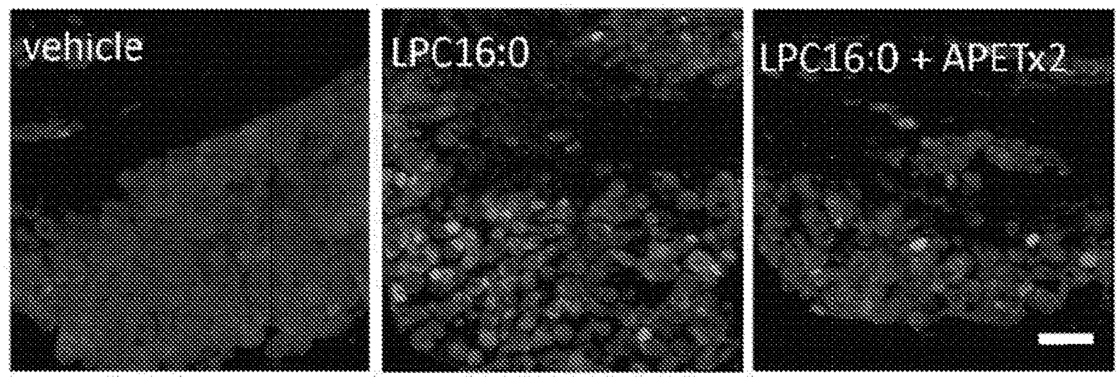
Figure 10G:
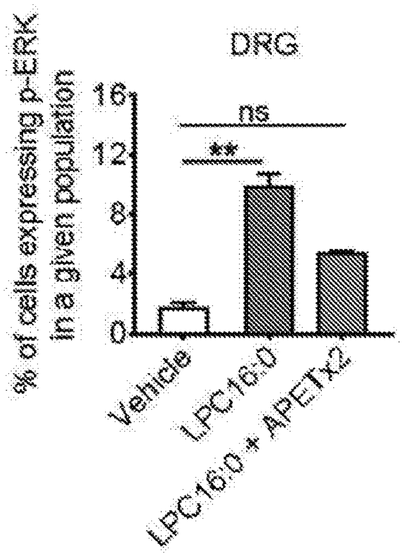
Figure 10H:
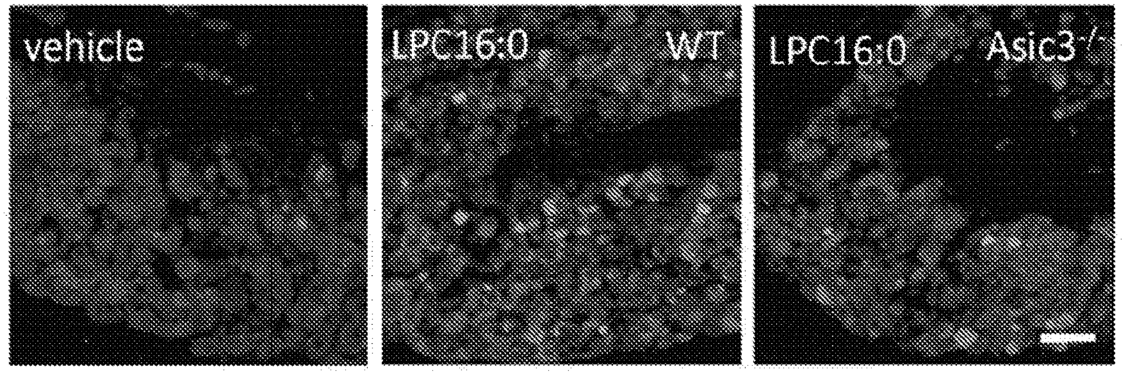
Figure 10I:
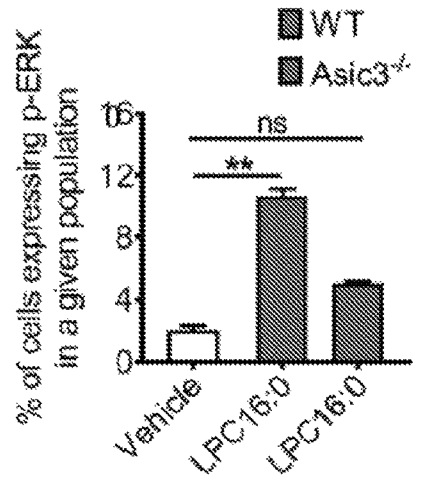
Figure 10J:
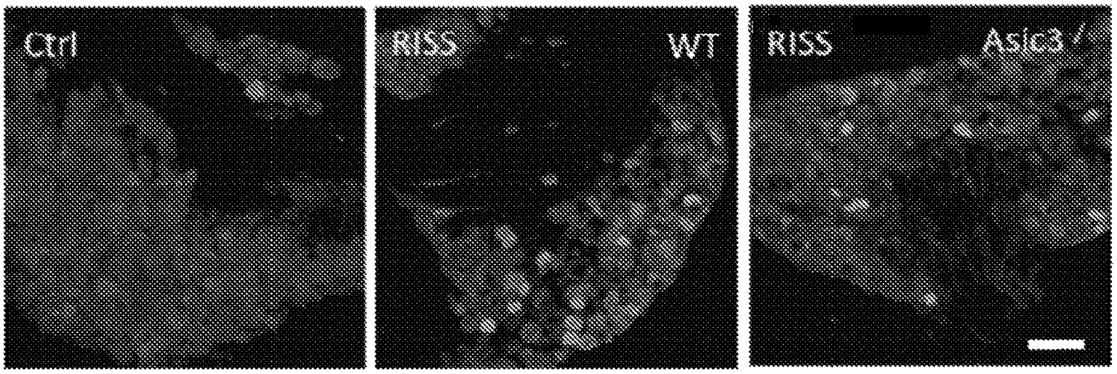
Figure 10K:
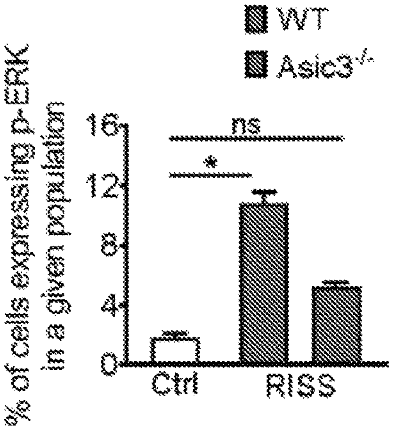
Figure 10L:
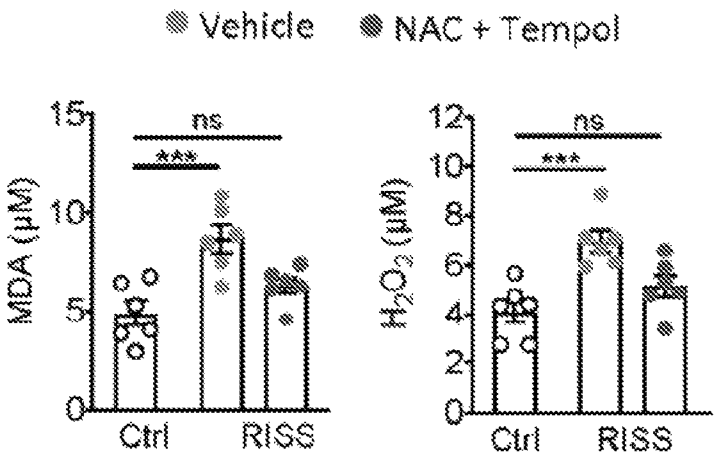
Figure 10M:
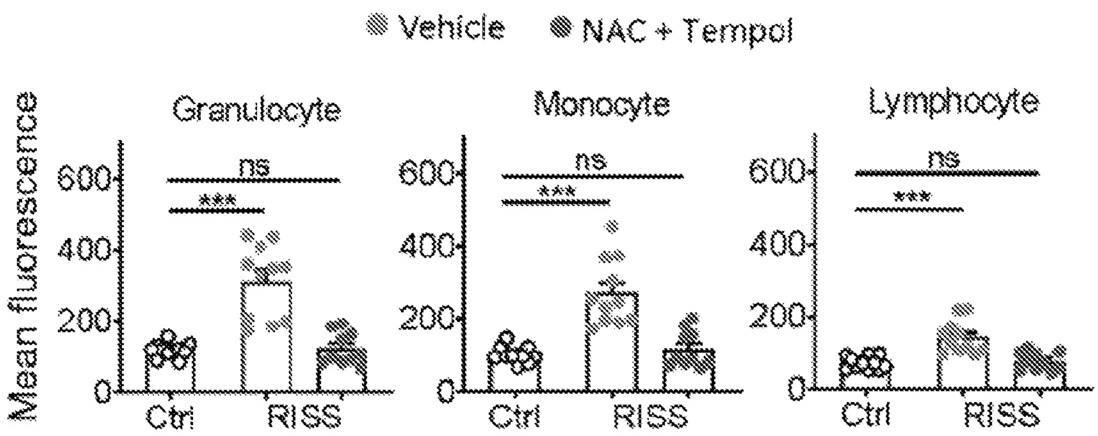

FIGS. 10A to 10M show that repeated LPC16:0 injection induces chronic hyperalgesia by an ASIC3-dependent mechanism. FIG. 10A shows the representative images of pERK expression of L4 dorsal root ganglia (DRG) neurons after injection of LPC16:0 injection (i.m.) and vehicle. Arrowheads indicate examples of positive pERK expression. Scale bar: 100 μm. FIG. 10B shows the quantification of pERK expression after LPC injection (n=3 mice per group; Mann-Whitney test). FIG. 10C shows the effect of repeated intramuscular LPC18:0 (left) and SM(d18:1/18:0) (right) injection on wild-type mice. Mice received two intramuscular injections (1 day apart) of neutral saline containing lipids (4.8 nmol) or vehicle. Mechanical hypersensitivity was assessed by the von Frey test. Arrows: lipid injection (LPC18:0 or SM(d18:1/18:0)). (n=6 per group; ANOVA). FIG. 10D shows the effect of ERK inhibitor (U0126) on the repeated LPC16:0 injection-induced chronic hyperalgesia as assessed by von Frey test. Intrathecal injection of U0126 (12.5 nmol) and its inactive analogue, U0124, was administered 30 minutes before first intramuscular LPC16:0 injection. Dark arrow show: U0126 or U0124 injection. Lighter arrows indicate LPC16:0 injection. (n=6 per group; ANOVA). FIG. 10E shows the analgesic effect of intraperitoneal administration of pregabalin, morphine, and diclofenac on repeated LPC16:0 injection model as assessed by von Frey test (n=6 per group; ANOVA). FIG. 10F shows the representative imaging of pERK expression of lumbar DRG neurons after intramuscular injection of vehicle, LPC16:0, and LPC16:0+APETx2 (ASIC3 inhibitor) at P0. Scale bar: 100 μm. FIG. 10G shows the quantification of pERK expression after injection of vehicle, LPC16:0 and LPC16:0+APETx2 (n=3 mice per group; Kruskal-Wallis test). FIG. 10H shows the representative imaging of pERK expression of L4 DRG neurons in WT and $Asic3^{-/-}$ mice at P0. Scale bar: 100 μm. FIG. 10I shows the quantitative analysis of pERK expression after LPC16:0 injection in WT and $Asic3^{-/-}$ mice (n=3 mice per group; Kruskal-Wallis test). FIG. 10J shows the representative imaging of pERK expression of lumbar DRG neurons after RISS in WT and Asic3$^{-/-}$ mice (at P0). Scale bar: 100 μm. FIG. 10K shows the quantitative analysis of pERK expression in WT and Asic3$^{-/-}$ mice (n=3 mice per group; Kruskal-Wallis test). FIG. 10L shows the effect of NAC (200 mg/kg bodyweight, i.p.) and Tempol (100 mg/kg bodyweight, i.p.) on serum oxidative stress in RISS mice at P0, as measured by serum MDA level (n=6) (left graph) and serum $H_2O_2$ content (n=6; both ANOVA) (right graph). FIG. 10M shows the effect of NAC and Tempol on intracellular oxidative levels of blood leukocytes in RISS mice (at P0). ROS levels were measured by emitted fluorescence intensity from immune cells after oxidation of intracellular DCFH by ROS (n=10 to 11 per group; ANOVA). LPC: lysophosphatidylcholine. LPC inj.: mice with repeated LPC16:0 injection. Ctrl: control. NAC: N-acetylcysteine. MDA: malondialdehyde. ROS: reactive oxygen species. Data are mean±SEM. * $p<0.05$,  $p<0.01$,  $p<0.001$, compared to vehicle (FIGS. 10B, 10C, 10E, 10G and 10I), U0124 treatment (FIG. 10D) or control (FIGS. 10K, 10L and 10M) (All 2-way ANOVA).

DETAILED DESCRIPTION OF THE EMBODIMENTS

The animal model provided in the present disclosure shows that psychological stressors can have a causative role in generating chronic hypersensitivity. The present disclosure also provides a pathophysiology of the stress-induced pain with evidence spanning molecular, pharmacological, behavioral and clinical levels in mouse stress models and patients with FM (FIG. 5F). That is, RISS inflicts excessive oxidative stress and lipid oxidization, thus resulting in ensuing production of lysophosphatidylcholine (LPC) 16:0 via platelet-activating factor acetylhydrolase (PAF-AH) catalyzation or spontaneous deacylation of ox-PCs. LPC16:0 accordingly evokes nociceptive responses and causes chronic hyperalgesia by activating the acid sensing ion channel 3 (ASIC3) in muscle tissue. By reducing LPC generation, PAF-AH inhibitor or antioxidants may thus be beneficial in the stress-related pain disorders, such as FM.

The present disclosure shows that peripheral nociceptive activation triggered by an oxidized lipid, LPC16:0, after stress exposure generates the stress-induced chronic non-inflammatory pain. With a clinical lipidomic approach, it is shown that patients with FM exhibited excess expression of LPC16:0, which was correlated with pain symptoms in those with increased oxidative stress and high disease severity.

The present disclosure shows that darapladib, a PAF-AH inhibitor, can effectively attenuate the RISS-induced chronic hyperalgesia. Since PAF-AH mediates both PAF degradation during inflammation and LPC synthesis during lipid oxidization, darapladib may have dual but opposite roles in the nociceptive process depending on the situation. Darapladib was less likely considered for analgesic purposes, given that PAF is a potent inflammatory mediator, and thus inhibiting its hydrolysis could aggravate nociceptive responses. However, under oxidative but noninflammatory conditions, such as RISS, the present disclosure shows that darapladib has a predominantly anti-nociceptive role by preventing LPC generation.

The present disclosure shows that repeated exposure to stress is essential for pain chronification. Similar to somatic noxious stimuli, psychological stimulation also has a hyperalgesic priming-like effect on pain development. The present disclosure shows that SISS triggers transient hypersensitivity, whereas repeated challenges like RISS induced long-lasting behavioral changes. Similar findings were also observed in the single and repeated LPC16:0 injection experiment. It is also found that repeated intramuscular but not intraplantar LPC injection caused chronic hyperalgesia, so that the priming-like effect mainly relies on the muscle afferents.

In the present disclosure, it is found that both RISS and LPC16:0-injected mice responded to pregabalin treatment but not to morphine or diclofenac.

In order to provide a clear and ready understanding of the present disclosure, certain terms are first defined. Additional definitions are set forth throughout the detailed description. Unless defined otherwise, all technical and scientific terms used herein have the same meanings as is commonly understood by one of skill in the art to which this disclosure belongs.

In the RISS model of the present disclosure, upregulation of numerous lipids other than LPC16:0 at P0 are also observed. Therefore, the pathogenic metabolite may not be limited to LPC16:0 but also possibly includes other undetermined lipids. Furthermore, other types of metabolites generated with ROS other than lipids may also induce allodynia. Likewise, in clinical lipidomic profiling, the potential pathogenic substances may not be limited to LPC16:0 but could include other lipids, given that various other lipids also showed significant incremental changes and fair correlation with clinical presentations, such as LPC18:1, LPC22:6 and Cer(d18:1/22:0).

As used herein, the articles "a" and "an" refer to one or more than one (i.e., at least one) of the grammatical object of the article. By way of example, "an element" means one element or more than one element.

As used herein, the term "about" or "approximately" refers to a degree of acceptable deviation that will be understood by a person of ordinary skill in the art, which may vary to some extent depending on the context in which it is used. In general, "about" or "approximately" may mean a numeric value having a range of ±10% around the cited value.

As used herein, the term "comprise" or "comprising" is generally used in the sense of include/including which means permitting the presence of one or more features, ingredients or components. The term "comprise" or "comprising" encompasses the term "consists" or "consisting of."

As used herein, the terms "subject," "individual" and "patient" refer to any mammalian subject for whom diagnosis, prognosis, treatment, or therapy is desired, particularly humans. Other subjects may include cattle, dogs, cats, guinea pigs, rabbits, rats, mice, horses, and so on.

As used herein, the term "pain" or "related pain disorder" refers to an unpleasant feeling often caused by intense or damaging stimuli, including different types and symptoms of pain. As used herein, the related pain disorder in a subject may not necessarily perceived by the subject as pain but can also include feelings of discomfort, such as muscular discomfort and limb soreness. For example, the muscular discomfort can be caused by restless leg syndrome (RLS). Up to one-third of patients with FM reported comorbid RLS symptoms, and limb soreness is a very common description of uncomfortable sensations in RLS, found in up to 40.4% of subjects with RLS.[65, 66, 67]

As used herein, the term "treating" or "treatment" refers to the application or administration of one or more active agents to a subject afflicted with a disorder, a symptom or condition of the disorder, or a progression of the disorder, with the purpose to cure, heal, relieve, alleviate, alter, remedy, ameliorate, improve, or affect the disorder, the symptom or condition of the disorder, the disabilities induced by the disorder, or the progression of the disorder.

As used herein, the term "preventing" or "prevention" refers to preventive or avoidance measures for a disease or symptoms or conditions of a disease, which include but are not limited to applying or administering one or more active agents to a subject who has not yet been diagnosed as a patient suffering from the disease or the symptoms or conditions of the disease but may be susceptible or prone to the disease. The purpose of the preventive measures is to avoid, prevent, or postpone the occurrence of the disease or the symptoms or conditions of the disease.

As used herein, the term "effective amount" refers to that amount of an active agent sufficient to achieve a desired therapeutic, prophylactic, and/or biological effect in a subject, such as reducing drug-induced side effects, or prohibiting, improving, alleviating, reducing or preventing one or more symptoms or conditions or progression of a disease. The actual effective amount may change depending on various reasons, such as administration route and frequency, body weight and species of the individual receiving said pharmaceutical, and purpose of administration. A person skilled in the art may determine the dosage in each case based on the disclosure herein, established methods, and their own experience. For example, an active agent as described herein is effective in providing pain relief or preventing hyperalgesia or reducing level or duration of pain.

As used herein, the terms "platelet-activating factor acetylhydrolase (PAF-AH)" and "lipoprotein-associated phospholipase A2 (Lp-PLA2)" are used interchangeably. The enzyme is responsible for the conversion of oxidized low density lipoprotein (LDL) to its lysophosphatidylcholine form. Specifically, it can hydrolyze oxidized phosphatidylcholine to give lysophosphatidylcholine and an oxidatively modified fatty acid. The amino acid sequence of the enzyme and corresponding nucleotide sequence are well known in the art, for example, as described in U.S. Pat. No. 5,981,252 (human PAF-AH, GenBank Accession No.: U20157, Ref. Seq. ID: NM-005084 and NP-005075), the contents of which are incorporated by reference.

The present disclosure is based on the innovative concepts that lipid oxidation and subsequent upregulation/accumulation of certain lysophosphatidylcholine (LPC) triggers nociceptive signaling to cause chronic hypersensitivity, and inhibition of PAF-AH significantly reduces the production of such LPC and blocks the development of pain.

Accordingly, the present disclosure relates to prevention or treatment of pain by means of inhibition of PAF-AH.

In an embodiment, inhibition of PAF-AH is performed by a PAF-AH inhibitor. Examples of a PAF-AH inhibitor can include nucleic acid molecules (e.g., an anti-sense nucleic acid molecule directed to a PAF-AH gene or a small interfering RNA (siRNA) directed toward a PAF-AH nucleic acid), polypeptides (e.g., antibodies), or a small molecule PAF-AH inhibitory compound.

As used herein, the term "small molecule" refers to organic or inorganic molecules either synthesized or found in nature, generally having a molecular weight less than 10,000 grams per mole, such as less than 5,000 grams per mole, less than 2,000 grams per mole, or less than 1,000 grams per mole. In some embodiments, a small molecule as described herein refers to a non-polymeric, e.g., non-protein or nucleic acid based chemical molecule. In some embodiments, a small molecule as described herein can have a molecular weight of about any of 500 to 10,000 Daltons, such as 500 to 5,000 Daltons.

Small molecules of PAF-AH inhibitory compounds are known and available in this art, for example, as described in PCT Patent Publication Application No. WO 01/60805A1 (corresponding to U.S. Pat. Nos. 6,649,619 and 7,153,861), U.S. Patent Publication Application Nos. 2012/0080497, 2008/0280829, 2008/0279846 and 2011/0306552, and U.S. Pat. No. 9,029,383, the contents of which are incorporated by reference. The compounds described herein can be prepared by published processes.

In some embodiments, PAF-AH inhibitory compounds as used herein can be those having Formula (I) below:

Formula (I)

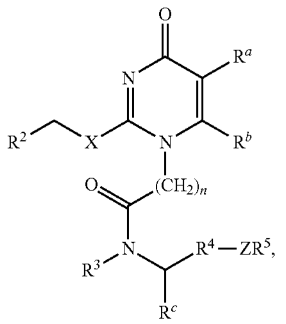

wherein

- $R^a$ and $R^b$ together with the pyrimidine ring carbon atoms to which they are attached form a fused 5-membered carbocyclic ring;
- each of $R^2$, $R^4$ and $R^5$, independently, is an aryl or heteroaryl group, unsubstituted or substituted by 1, 2, 3 or 4 substituents, which may be the same or different, selected from C(1-18)alkyl (e.g., C(1-6)alkyl), C(1-18) alkoxy (e.g., C(1-6)alkoxy), C(1-18)alkylthio (e.g., C(1-6)alkylthio), arylC(1-18)alkoxy (e.g., arylC(1-6) alkoxy), hydroxy, halogen, CN, $COR^6$, carboxy, $COOR^6$, $NR^6COR^7$, $CONR^8R^9$, $SO_2NR^8R^9$, $NR^6SO_2R^7$, $NR^8R^9$, mono to perfluoro-C(1-4)alkyl, mono to perfluoro-C(1-4)alkoxyaryl, and aryl(C1-4) alkyl;
- $R^e$ is hydrogen or C(1-3)alkyl;
- $R^3$ is hydrogen, C(1-6) alkyl which may be unsubstituted or substituted by 1, 2, 3 or 4 substituents selected from hydroxy, halogen, $OR^6$, $COR^6$, carboxy, $COOR^6$, $CONR^8R^9$, $NR^8R^9$, $NR^8COR^9$, mono or di-(hydroxyC (1-6)alkyl)amino and N-hydroxyC(1-6)alkyl-N—C(1-6)alkylamino;
- $R^6$ and $R^7$ are independently hydrogen or C(1-20)alkyl, for instance C(1-4)alkyl (e.g., methyl or ethyl);
- $R^8$ and $R^9$ which may be the same or different is each selected from hydrogen, C(1-2)alkyl (e.g., C(1-6)alkyl);
- n is an integer from 1 to 4, such as 1 or 3, e.g., 1;
- X is O or S;
- Y is $(CH_2)p(O)q$ in which p is 1, 2 or 3 and q is 0, or p is 2 or 3 and q is 1; and
- Z is O or a bond.

As described herein, the term "alkyl" includes all straight chain and branched isomers. Examples of alkyl include, but are not limited to, methyl, ethyl, n-propyl, iso-propyl, n-butyl, sec-butyl, iso-butyl, t-butyl, n-pentyl and n-hexyl.

As described herein, the term "halogen" or "halo" include fluorine, chlorine, bromine and iodine and fluoro, chloro, bromo and iodo, respectively. In some examples, the halogen atom is fluorine.

As described herein, the term "aryl" refers to, unless otherwise defined, a mono- or bicyclic aromatic ring system containing up to 10 carbon atoms in the ring system, for instance, phenyl or naphthyl.

As described herein, the term "heteroaryl" refers to a mono- or bicyclic heteroaromatic ring system comprising up to four, e.g., 1 or 2, heteroatoms each selected from oxygen, nitrogen and sulphur. Each ring may have from 4 to 7, e.g., 5 or 6, ring atoms. A bicyclic heteroaromatic ring system may include a carbocyclic ring.

In some embodiments, $R^a$ is methyl or ethyl and $R^b$ is hydrogen or methyl; or $R^a$ and $R^b$ together with the pyrimidine ring carbon atoms to which they are attached form a fused 5- or 6-membered carbocyclic ring. For example, $R^a$ and $R^b$ together with the pyrimidine ring carbon atoms to which they are attached form a fused 5-membered carbocyclic ring.

In some embodiments, each of $R^2$, $R^4$ and $R^5$, independently, is an aryl group, optionally substituted by 1, 2, 3 or 4 substituents which may be the same or different selected from C(1-6) alkyl, C(1-6) alkoxy, C(1-6) alkylthio, hydroxy, halogen, CN, mono to perfluoro-C(1-4)alkyl, mono to perfluoro-C(1-4)alkoxyaryl, and arylC(1-4)alkyl. In some embodiments, $R^2$ is phenyl, optionally substituted by halogen, e.g., from one to three fluorine atoms.

Some examples of $R^2$ include phenyl and naphthyl. In some examples, $R^2CH_2X$ is 4-fluorobenzylthio.

Some examples of $R^4$ include phenyl, pyridine and pyrimidine. In some examples, R4 is phenyl.

Some examples of $R^5$ include phenyl or thienyl, optionally substituted by halogen or trifluoromethyl, e.g., at the 4-position. In some examples, $R^5$ is phenyl substituted by trifluoromethyl, e.g., at the 4-position.

In some embodiments, $R^4$ and $R^5$ together form a 4-(phenyl)phenyl, 2-(phenyl) pyrimidinyl or 2-(phenyl)pyridinyl substituent in which the remote phenyl ring may be optionally substituted by halogen or trifluoromethyl, e.g., at the 4-position. In some embodiments, $R^4$ and $R^5$ together form a 4-(4-trifluoromethylphenyl)phenyl moiety.

In some examples of the compound of formula (I) according to this disclosure, the compound has the Formula (I)-1:

Formula (I)-1

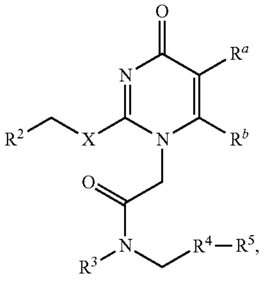

in which:

$R^a$, $R^b$, $R^2$, $R^3$, $R^4$, $R^5$, and X are as above-defined.

In some embodiments, $R^a$ and $R^b$ together with the pyrimidine ring carbon atoms to which they are attached form a fused 5-membered carbocyclic ring;

$R^2CH_2X$ is 4-fluorobenzylthio;

$R^3$ is C(1-3)alkyl substituted by $NR^8R^9$;

$R^4$ and $R^5$ form a 4-(4-trifluoromethylphenyl)phenyl moiety;

$R^8$ and $R^9$ which may be the same or different is each selected from hydrogen, or C(1-6)alkyl); and X is S.

Examples of the compounds of Formula I include but are not limited to N-[2-(diethylamino)ethyl]-2-{2-[(4-fluorobenzyl)sulfanyl]-4-oxo-4,5,6,7-tetrahydro-1H-cyclopenta[d]pyrimidin-1-yl}-N-{[4'-(trifluoromethyl)biphenyl-4-yl]methyl}acetamide,

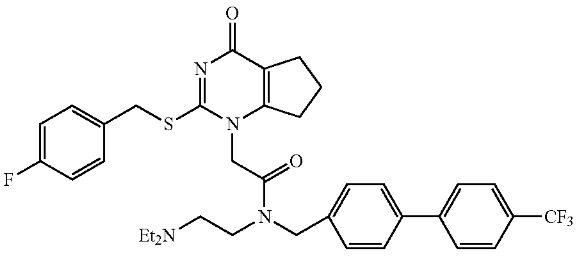

darapladib (known as for anti-atherogenic purposes); and 2-[2-[(2,3-difluorophenyl)methylsulfanyl]-4-oxoquinolin-1-yl]-N-[1-(2-methoxyethyl)piperidin-4-yl]-N-[[4-[4-(trifluoromethyl)phenyl]phenyl]methyl]acetamide

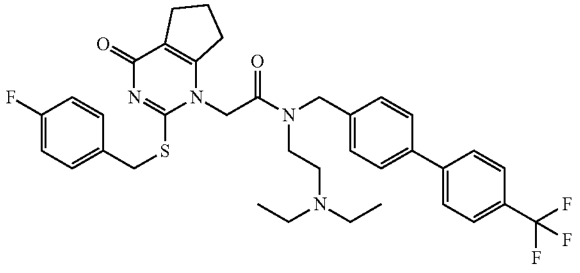 [SMILES: CCN(CC)CCN(Cc1ccc(-c2ccc(C(F)(F)F)cc2)cc1)C(=O)Cn1c(SCc2ccc(F)cc2)nc(=O)c2c1CCC2]

rilapladib (analogues of darapladib).

In another aspect, the present disclosure is based on the innovative concepts that lipid oxidation and subsequent upregulation/accumulation of certain lysophosphatidylcholine (LPC) triggers nociceptive signaling to cause chronic hypersensitivity, and antioxidants or ROS scavengers significantly reduce the production of such LPC and block the development of pain.

Accordingly, the present disclosure relates to prevention or treatment of pain by means of antioxidants or ROS scavengers.

As used herein, antioxidants or ROS scavengers are agents that inhibit the formation of oxidation products. Such an agent may be, e.g., tyrosinase inhibitors and/or o-quinone scavengers and/or $Cu^{++}$ chelators and/or antioxidants, and/or tetrahydroquinolines. For example, contemplated antioxidants or ROS scavengers may include o-quinone scavengers such as, but not limited to, N-acetyl cysteine, glutathione, ascorbic acid, Na-ascorbate, and/or L-cysteine. For example, a contemplated formulation for prevention or treatment of pain may include ascorbic acid and a cysteine, L-cysteine or N-acetyl cysteine. In some embodiments, formulations for prevention or treatment of pain may include an agent chosen from one or more of tyrosinase inhibitors such as captopril, methimazole, quercetin, arbutin, aloesin, N-acetylglucoseamine, retinoic acid, β-tocopheryl ferulate, MAP (Mg ascorbyl phosphate), substrate analogues (e.g., sodium benzoate, L-phenylalanine), $Cu^{++}$ chelators (for example, Na 2-EDTA, Na 2-EDTA-Ca), dimercaptosuccinic acid (DMSA; succimer), DPA (D-penicillamine), trientine-HCl, dimercaprol, clioquinol, sodium thiosulfate, triethylenetetramine (TETA), tetraethylenepentamine (TEPA), curcumin, neocuproine, tannin, and/or cuprizone. Other contemplated anti-oxidants that may be used include sulfite salts, e.g., sodium hydrogen sulfite or sodium metabisulfite, di-tert-butyl methyl phenols, tert-butyl-methoxyphenols, polyphenols, tocopherols and/or ubiquinones, including but not limited to caffeic acid.

Contemplated antioxidants that can be included in disclosed compositions may be selected from, e.g., thiols such as aurothioglucose, dihydrolipoic acid, propylthiouracil, thioredoxin, glutathione, cysteine, cystine, cystamine, and thiodipropionic acid; sulphoxitnines such as buthionine-sulphoximines, homo-cysteine-sulphoximine, buthionine-sulphones, and penta-, hexa- and hepta-thionine-sulphoximine; metal chelators such as $\alpha$-hydroxy-fatty acids, palmitic acid, phytic acid, lactoferrin, citric acid, lactic acid, malic acid, humic acid, bile acid, bile extracts, bilirubin, biliverdin, ethylenediaminetetraacetic acid (EDTA), ethylene glycol tetraacetic acid (EGTA), and diethylenetriaminepentaacetic acid (DTPA); sodium metabisulfite; vitamins such as vitamin E, vitamin C, ascorbyl palmitate, Mg ascorbyl phosphate, and ascorbyl acetate; phenols such as butythydroxytoluene, butylhydroxyanisole, ubiquinol, nordihydroguaiaretic acid, and trihydroxybutyrophenone; benzoates such as coniferyl benzoate; uric acid; mannose; propyl gallate; selenium such as selenium-methionine; stilbenes such as stilbene oxide and trans-stilbene oxide; and combinations thereof.

The compounds described herein may be in a variety of forms, including the compounds themselves, as well as their pharmaceutically acceptable salts, solvates, and hydrates, etc.

As used herein, the term "pharmaceutically acceptable salt" includes acid addition salts. "Pharmaceutically acceptable acid addition salts" refer to those salts which retain the biological effectiveness and properties of the free bases. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, citric acid, maleic acid, malonic acid, oxalic acid, succinic acid, tartaric acid, by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

In certain embodiments, the compound is in the form of a hydrate or solvate. As used herein, the term "hydrate" refers to a compound non-covalently associated with one or more molecules of water. Likewise, the term "solvate" refers to a compound non-covalently associated with one or more molecules of an organic solvent.

According to the present disclosure, the compounds as described herein may be used as an active ingredient for preventing or treating pain. In use, a therapeutically effective amount of the active ingredient may be formulated with a pharmaceutically acceptable carrier into a pharmaceutical composition of an appropriate form for the purpose of delivery and absorption.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present disclosure can provide the effect of rapid, continued, or delayed release of the active ingredient after administration to the patient. The form of said composition may be tablets, pills, powder, lozenges, packets, troches, elixirs, suspensions, lotions, solutions, syrups, soft and hard gelatin capsules, suppositories, sterilized injection fluid, and packaged powder, for example.

The composition of the present disclosure may be delivered via any physiologically acceptable route, such as oral, parenteral (such as intramuscular, intravenous, subcutaneous, and intraperitoneal), transdermal, suppository, and intranasal methods. Regarding parenteral administration, it may be used in the form of a sterile water solution, which may comprise other substances, such as salts or glucose sufficient to make the solution isotonic to blood. The water solution may be appropriately buffered (e.g., with a pH value of 3 to 9) as needed. Preparation of an appropriate parenteral composition under sterile conditions may be accomplished with standard pharmacological techniques well known to a person skilled in the art, and no extra creative labor is required.

According to the present disclosure, the compounds as described herein can be used as a PAF-AH inhibitor for preventing or treating pain or pain disorders. Therefore, the present disclosure provides a method for preventing or treating pain by administering the compounds as described herein or a composition comprising the same to a subject in need thereof. For example, the PAF-AH inhibitor compound as described herein is administered in an amount effective in (i) inhibiting the enzymatic activity of PAF-AH, (ii) reducing the generation of lysophosphatidylcholines (LPCs), e.g., LPC16:0, and/or (iii) reducing hyperalgesia, e.g., chronic, long-lasting hyperalgesia, in the subject in need thereof.

In some embodiments, the method of the present disclosure is effective in preventing or treating stress-related pain.

In some embodiments, the method of the present disclosure is effective in preventing or treating chronic pain, e.g., chronic non-inflammatory pain.

FM is one typical example of the pain disorder to be treated as described herein. Other examples include primary headache (migraine or tension type headache). Additional examples include the pain associated with an irritable bowel syndrome, a bladder pain syndrome and a temporomandibular disorder.

In another aspect, the present disclosure provides a method for producing a non-human animal model for pain. In another aspect, the non-human animal model provided by the present disclosure is used for generation and management of pain. Also provided is a non-human animal model for pain thus prepared.

In some embodiments, the method comprises applying repeated sound stimuli to a non-human animal, thereby resulting in the development of pain behavior in the animal. For example, the repeated sound stimuli comprises a set of continuous pure tones with randomly varied frequencies (e.g., 5-19 kHz), duration (e.g., 5-10 seconds) and amplitudes (e.g., 0-100 dB), lasting for a given period of time without interval (e.g., about 30 mins), wherein the set of continuous pure tones is presented repeatedly (multiple times per day, e.g., presented every 3 hours for 6 times overnight, for at least three separate days, the interval between two adjacent days being not more than one day, e.g., on days 1, 3 and 4).

In other embodiments, the method comprises administering LPC16:0 to a non-human animal, thereby resulting in the development of pain behavior in the animal. For example, the LPC16:0 is administered by repeated muscular injection.

In some embodiments, the resultant non-human animal model exhibits pain behavior including but not limited to acute or chronic pain, hyperalgesia (mechanical, thermal and/or muscle) anxiety-like behavior and/or fatigue-like behavior. In some embodiments, the pain behavior is long lasting for at least 2, 3, 4 or 5 weeks, for example.

In some embodiments, the animal model is a mammal such as a mouse, a rat, a rabbit, a pig, a cow, a dog, and a monkey.

According to the present disclosure, the animal model can be used for screening for a candidate analgesic agent for preventing or treating pain.

Therefore, the present disclosure further provides a method as a platform for screening for a candidate analgesic agent based on the animal model as described herein.

In an embodiment, the method comprises the steps of (i) administering a test agent to the animal model, and (ii) measuring whether at least one of the pain behavior is reduced or alleviated, wherein reduction or alleviation of at least one of the pain behavior in the animal model via administration of the test agent indicates that the test agent is a candidate analgesic agent useful for preventing or treating pain.

Without further elaboration, it is believed that those skilled in the art will be able to apply the disclosure to its fullest extent based on the above description. The following examples are, therefore, intended to be illustrative, and are not intended to limit the applicable scope of the disclosure in any way. All documents cited herein are incorporated herein by reference.

EXAMPLES

Psychosocial stress precipitates not only psychiatric illness but also various pain disorders, like FM. However, whether and how psychological stressors engage in pain generation remains undetermined. Using sound stimulus as psychological stressors, it was demonstrated that exposure to repeated and intermittent sound stress (RISS) triggered chronic non-inflammatory hyperalgesia in mice without overt tissue injury. It was found that excessive oxidative stress inflicted by RISS caused lipid oxidization and subsequent upregulation of lysophosphatidylcholine (LPC) 16:0, which thus triggered nociceptive signaling to cause chronic hypersensitivity. Pharmacological or genetic inhibition of acid-sensing ion channel 3 impeded the development of LPC16:0-induced chronic hyperalgesia, suggesting the involvement of ASIC3 in the development of stress-induced pain. Furthermore, darapladib, a drug designed for anti-atherogenic purposes, and antioxidants effectively alleviate the RISS-induced pain or hyperalgesia by inhibiting LPC16:0 synthesis. Clinical evidence showed that excessive LPC16:0 exists in FM cases, and LPC16:0 expression was correlated with pain symptoms in patients with high oxidative stress and disease severity. This disclosure provides an organic basis for how perceived stress translates into the processing of chronic non-inflammatory pain, thereby indicating new therapeutic approach for FM.

Materials and Methods

Mice

All animal procedures were performed in accordance with protocols approved by the IACUC of the Institute of Biomedical Science, Academia Sinica (Protocol #16-11-1000). Adult (8 to 12-week-old) female C57BL/6JNarl mice were used. All procedures were approved by the Institutional Animal Care and Use Committee of Academia Sinica and followed the Guide for the Use of Laboratory Animals (National Academy Press, Washington, DC)[41]. Asic$^{-/-}$ mice were generated and genotyped as previously described[42]. This disclosure aimed to minimize the number of animals used and their suffering without compromising the quality of the experiments.

RISS Model

Figure 1A:
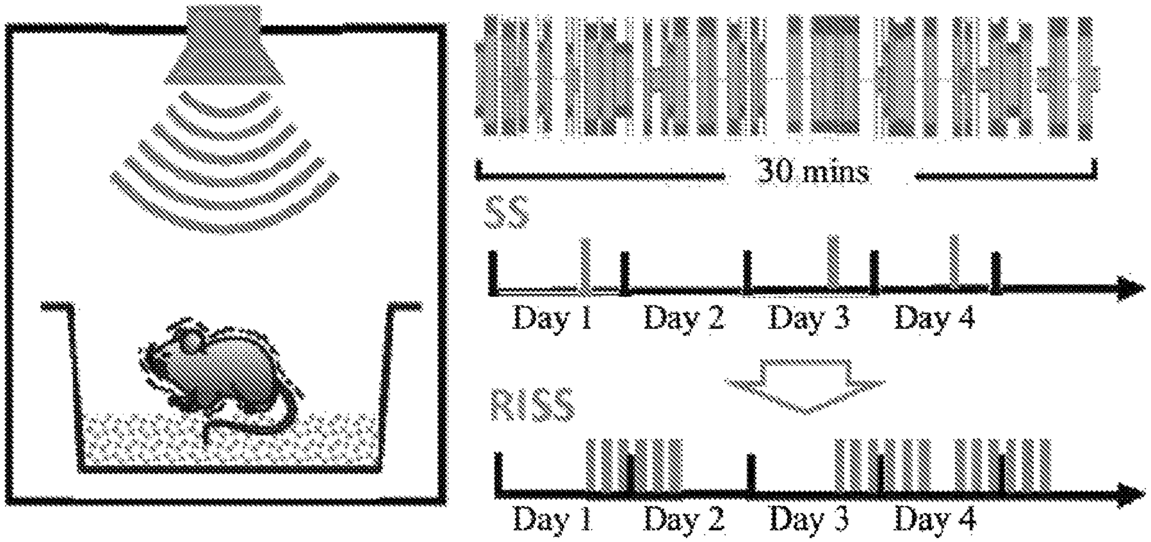
FIGS. 1A to 1G show that repeated and intermittent sound stress (RISS) induces fibromyalgia-like pain behaviors in mice.

Sound stressors were applied as described[14, 43] with modification. Mice were placed (3 per cage) in a 20×30×15 cm bedding cage, which was kept 25 cm below a speaker, inside a 40×50×35 cm sound-insulated box. A speaker emitted pure tones at 5 frequencies (5, 11, 13, 15 and 19 kHz) with random amplitudes varied over time for each frequency (0, 20, 60, 90, and 100 dB sound). Each tone stimulus lasted for 5 or 10 sec in random order, and mice were stimulated continuously without interval. The sound stressors continued for 30 min as a set. In the original SS (sound stress) protocol, a set of 30-min stimuli was given once a day on days 1, 3, and 4 (FIG. 1A)[14]. The RISS model intensified the stress protocol by increasing the stimulus frequency: a set of sound stimulus was repeated every 3 hours for 6 times overnight (from 16:00 to 10:00), followed by resting silence for 6 hours (from 10:00 to 16:00). The procedure was repeated on days 1, 3, and 4 as for the SS protocol. The control groups were placed in similar chambers for 4 days without stress exposure. Both groups of mice had access to food and water freely during the stress period. After the stimulus procedure, mice were returned to their original home cages in the animal care facility. In both the SS and RISS protocols, the day after completing the stress stimuli is called P0; the post-stress day 1, P1; and so on. In the experimental design of the 29 single-day stimuli of intermittent SS (SISS), the day after SISS is called P'0; the post-stress day 1, P'1; and so on.

Repeated LPC16:0 Injection Model

The chronic pain model was based on the repeated acid injection model protocol by Sluka et al.[44], and LPC16:0 was used for pain induction to replace acidic saline injection. Mice received in the left gastrocnemius muscle two intramuscular injections (1 day apart) of 10 μL neutral saline solution (pH 7.4; buffered with HEPES) containing vehicle (0.96% ethanol) or LPC16:0 (4.8 nmol; Avanti Polar Lipids Inc)[30]. In the experiment of pharmacological inhibition of ASIC3, APETx2 (50 pmole; Alomone, Israel), a selective ASIC3 antagonist, was co-injected with LPC16:0.

Behavioral Assays

All sensory testing was performed in the same procedure room. Animals were acclimated to the environment (room, cage, and experimental tools) before testing. The experimenter stayed with the animals during habituation to reduce the risk of analgesia related to experimenter-induced stress. The experimenter was blind to the treatment types and genotypes in all behavioral studies.

Von Frey Filaments (Assessment of Mechanical Hyperalgesia)

Animals were placed on an elevated mesh platform, and a 0.2-mN von Frey filament was applied to the plantar surface of both hind paws. A positive response was defined as lifting, shaking, guarding, or licking paws when the stimulus was applied. For each paw, the filament was applied 5 times at 30-sec intervals.

Hargreaves Test (Assessment of Thermal Hyperalgesia)[45]

Mice were placed individually in Acrylic cubicles mounted on a glass surface maintained at 30° C. The test was performed after acclimatization. The thermal stimulus of the radiant heat was then applied to the plantar surface of each hind paw. Each mouse was tested in three sequential trials with an interval of 2-3 min. The assay cutoff was set at 30 sec to prevent tissue damage. Paw withdrawal latencies were calculated as the mean of three measures.

Muscle Withdrawal Threshold Test (Assessment of Muscular Hyperalgesia)

Muscle withdrawal thresholds were evaluated as described[46]. A hand-made cone-shaped tweezer (2.3 mm in diameter) was placed on a pressure-measurement device (38500—P.A.M. Pressure Application Measurement, Ugo Basile). Mice were trained to acclimate in an experimenter's glove with hind-limbs passively extended. This force-sensitive tweezer was applied to the belly of the bilateral gastrocnemius muscles. Mice underwent an average of three trials per animal.

Grip Force Test (Assessment of Fatigue-Like Behaviors)[47]

A metal mesh (4×8 cm) was attached to force-sensitive device (MK-380CM/R, Muromachi) for forelimb grip. Mice were familiarized with the apparatus by performing the grip force task 1 week before regular data collection. Each mouse was placed around the mesh to acclimate to the environment for at least 15 min before testing. After adequate grasping on the mesh, mice were pulled by the tail to measure grip force of the forelimb. Grip force was calculated from an average of 5 trials per animal.

Open Field and Elevated Plus Maze Test

In the open field test, spontaneous locomotor and exploring activity were measured in the open arena (48×48 cm). After habituation for 1 hour in the home cage, each male mouse was released into a corner of the arena and allowed to explore for 20 min. In the elevated plus maze test, mice were placed in the maze consisting of two open arms with 1-cm ledges and two enclosed arms with 15-cm walls during a 5-min period. The maze was elevated to a height of 50 cm above the floor during the task. The recorded moving trace and time spent in the defined regions of each mouse were analyzed by using the TopScan system (Clever System, Reston, VA).[31]

Drug Injections

Analgesic drugs: Pregabalin (0.3, 1, 3 or 10 mg/kg bodyweight, i.p.; Toronto Research Chemicals), morphine (0.3, 1, 3 or 10 mg/kg bodyweight, i.p.), diclofenac (1, 3 or 10 mg/kg bodyweight, i.p.; Sigma-Aldrich) or vehicle (0.9% saline) was administered, and the effect of each drug was evaluated by testing 6 mice. Sensory testing was carried out at 30 min and 1, 3 and 24 hours after injection of vehicle or drugs, with the experimenter blinded to the dose of test drugs. Because the RISS-induced hyperalgesia decreased gradually over time, the experiments of drug responses should be conducted as early as possible after stimulation is completed to ensure that the impact of behavioral attenuating changes interfered least with the pharmacological assessment. In addition, given the transient effects of analgesics (less than few hours), the mice were repeatedly used to comply with the 3Rs principle. The 3Rs stand for Replace, Reduce, Refine and represent a responsible approach to animal testing. The goal is to replace animal experiments whenever possible. In addition, the aim is to keep the number of animal experiments as low as possible and to only use the necessary number of animals. Lastly, it is vital to ensure that the distress inflicted upon the animals is as low as possible. Therefore, all the pharmacological studies were conducted on post-RISS day 1 and day 4 (3 days apart, within 1 week after RISS). Mice of post-stress day 1 and day 4 were assigned randomly but equally to each tested dosage for counterbalance. During testing, the experimenter was blind to the individual treatment assignments.

Mitogen-activated protein kinase 1/2 inhibitors: Intrathecal administration of ERK inhibitor U0126 (12.5 nmol; Sigma-Aldrich) and its inactive analogue U0124 were performed 30 minutes before the first LPC16:0 injection. Intrathecal injection was conducted through transcutaneous injection with a 30-gauge needle at the L5-6 dorsal spinal process under anesthesia of isoflurane (1.5%).

Antioxidants: Systemic administration of NAC (200 mg/kg bodyweight, i.p.; Sigma-Aldrich) with Tempol (100 mg/kg bodyweight, i.p.; Sigma-Aldrich) or vehicle (phosphate buffered saline; PBS) was given 30 min before and after each RISS procedure at days 1, 3 and 4 (FIG. 3M)[48-50]. A total of 6 doses of drug were given during the RISS protocol. Sensory testing was performed 1 hour after the last drug injection at P0 and at P4 and P7.

Figure 3A:
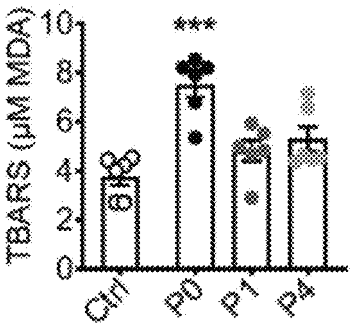
FIGS. 3A to 3O show that LPC16:0 resulting from lipid oxidization inflicts RISS-induced chronic hyperalgesia via activating ASIC3.
Figure 3B:
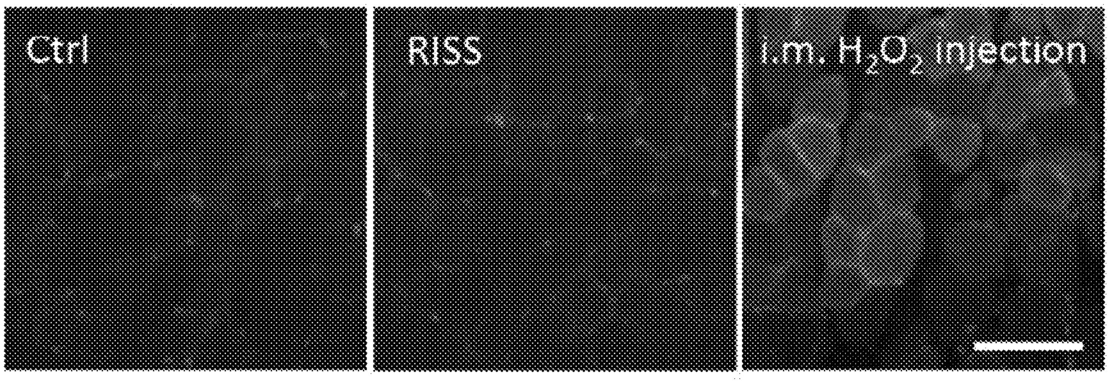
FIG. 3B shows the representative imaging of ROS expression in gastrocnemius cross-sections at P0 in control and RISS groups, and positive controls with intramuscular $H_2O_2$ injection into gastrocnemius muscles. Tissue ROS levels were measured by CM-$H_2$DCFDA staining. Scale bar: 80 μm.
Figure 3C:
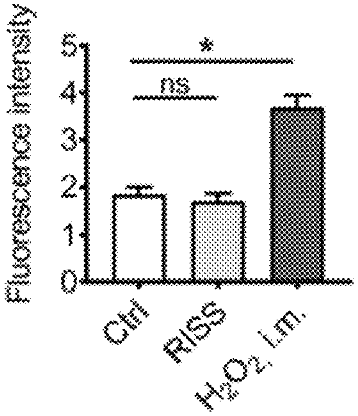
FIG. 3C shows the quantification of ROS expression in gastrocnemius muscles of control, RISS mice and positive controls with intramuscular $H_2O_2$ injection (n=3 mice per group). (Kruskal-Wallis test).

PAF-AH inhibitors. Darapladib (Cayman, Ann Arbor, MI) was solubilized in DMSO: PBS containing 1% methyl-β-cyclodextrin (1:99) and given once daily by i.p. injection at 10 mg/kg body weight. Mice were randomly assigned to receive vehicle or darapladib for 5 consecutive days during RISS (FIG. 3M). Sensory testing was carried out 1 hour after the last drug injection at P0 and at P4 and P7, with the experimenter blinded to the experimental groups.

ROS Determination

ROS levels in muscle tissue. Mice were euthanized with urethane (1.3 mg/g, i.p.; Sigma-Aldrich), then sacrificed immediately after the RISS procedure. All efforts were made to minimize stress before tissue sampling. Quadriceps samples were frozen in optimal cutting temperature (OCT) compound in liquid nitrogen-cooled isopentane. Six to eight sections of muscle tissue per mice were obtained from 3 mice in each experimental group. Frozen cross-sections were obtained, then washed with ice-cold PBS for 5 min. The muscle sections were further incubated with 300 nM CM-$H_2$DCFDA (C6827; Invitrogen) in PBS at 37° C. for 30 min and washed again with ice-cold PBS to stop the reaction. Positive controls were intramuscular injection of $H_2O_2$ containing PBS (100 mM, 20 μL) into the gastrocnemius muscle. Images were acquired under a Carl Zeiss fluorescence microscope. Fluorescence intensity of at least four fields per section was quantified by using Fuji (ImageJ, NIH) software.

ROS levels in immune cells. Blood was collected in EDTA tubes from the stressed mice at P0 immediately after the RISS procedure and control group via cardiac puncture. All efforts were made to minimize stress before blood collection. Blood samples (50 μL from each mouse) were added in 3 mL lysis buffer (BD Bioscience) for erythrolysis. Samples were placed in dark for 10 min and under centrifugation thereafter (447×g; 5 min; 24° C.). After the supernatant was removed, 2 mL cell wash solution (5% bovine serum albumin in PBS) was added to the sediments and gently vortexed. A second centrifugation and sequent removal of supernatant were carried out under the same condition. An amount of 0.3 mL HBSS buffer and 1.67 μL CM-$H_2$DCFDA (50 μM, C6827; Invitrogen) was added to the sediment. The samples were again gently vortexed, then incubated in the dark for 15 min at 37° C. After the incubation was completed, the samples were immediately placed on ice for 5 min to stop the reaction. Flow cytometry was used to separate the types of leukocytes and measure intracellular ROS levels (FACS-Scan, Becton-Dickinson, Immunofluorometry Systems). Granulocytes, monocytes, and lymphocytes were differentiated by their size (forward light scatter) and relative granularity (side light scatter; excited with a 488-nm argon laser beam). Oxidation of the CM-$H_2$DCFDA in immune cell resulted in increased mean fluorescence intensity, so intracellular ROS levels in each cell were evaluated by measuring the emitted fluorescence.

Lipid peroxidation and hydrogen peroxide ($H_2O_2$) determination. Blood samples were collected in the control and RISS mice by cardiac puncture. All efforts were made to minimize stress during blood collection. Serum lipid peroxidation levels were determined by thiobarbituric acid reactive substance (TBARS) assay with a commercial kit (Cayman, Ann Arbor, MI). TBARS were expressed in terms of malondialdehyde levels. Serum $H_2O_2$ concentrations were measured with OxiSelect ADHP/Resorufin fluorescence assay (Cell Biolabs, STA-344).

Histological and Immunofluorescence Analysis

Hematoxylin and eosin staining. Animals were anesthetized with urethane (1.3 mg/kg, i.p.), and then sacrificed. Gastrocnemius muscle samples were frozen in OCT compound in liquid nitrogen-cooled isopentane. Frozen tissue was prepared as 7 μm cross sections and immersed with Meyer's hematoxylin followed by 0.5% Eosin Y disodium in 70% alcohol according to standard protocols. Digital microscopy recordings were used with magnification ×200. Muscle specimens from three mice per group were investigated.

Hematological and serum biochemical analysis. Blood samples from control and RISS mice were collected in EDTA tubes by cardiac puncture. Serum was extracted after centrifugation (15,000 g, 15 min, at 4° C.), and preserved at −80° C. until analysis. Hematological and biochemical analyses were conducted commercially with Fuji DRI-CHEM 4000i. Serum TNF-α levels were determined by commercial kit (ELISA Kit, Cayman).

Serum stress hormone measurement. Blood samples were collected in the control and RISS mice by cardiac puncture. All mice were euthanized by using urethane (1.3 mg/kg, i.p.) between 8:00-10:00, and all efforts were made to minimize stress before blood collection. Samples were centrifuged (15,000 g, 15 min, at 4° C.), and then serum was extracted and preserved at −80° C. until analysis. Corticosterone and epinephrine levels were determined by ELISA kits (Corticosterone ELISA Kit, Cayman, and 2-CAT Research ELISA, LDN). Hormone levels were determined at baseline and P0, and at P7, P14, P21 and P28 after RISS.

Intramuscular pH measurement. Intra-musculofascial pH was measured with pH electrode (Hanna Instruments) placed within the belly of adductor magnus muscle belly under anesthesia of isoflurane (1.5%) in RISS mice at P0.

Immunofluorescence staining. Animals were euthanized with urethane (1.3 mg/kg, i.p.) and perfused with 4% paraformaldehyde (PFA) at P0. L4 dorsal root ganglia (DRG) were extracted and immediately post-fixed in 4% PFA for 60 min, and then replaced with 30% sucrose overnight. DRG were embedded in OCT compound and sectioned (12 μm) with a Leica cryostat. Six to eight sections per mice (3 to 4 sections from each side DRG) were obtained from 3 mice in each experimental group. After three washes with TRIS-buffered saline (TBS), slices were blocked with a TBS solution containing 5% bovine serum albumin and 0.1% Triton X-100 for 2 hours at room temperature, and then incubated with primary antibodies at 4° C. overnight [rabbit anti-ATF-3 at 1:1000, Santa Cruz Biotechnology; rabbit anti-phospho-p44/42 Map Kinase (Thr202/Ty204) antibody (pERK) at 1:500, Cell Signaling; goat anti-calcitonin gene-related peptide (CGRP) at 1:500, Bio-Rad; guinea pig anti-substance P at 1:500, Neuromics; mouse anti-Neurofilament 200 kDa Antibody, clone N52, at 1:500, Millipore]. Slices were rinsed three times with TBS, and then incubated at room temperature for 60 min with DyLight 594-conjugated IB4 (at 1:200, Vector Laboratories) or corresponding AlexaFluor-conjugated secondary antibodies [at 1:200, Alexa 488-conjugated donkey anti-rabbit IgG, Alexa 594-conjugated donkey anti-goat IgG, Alexa 594-conjugated goat anti-guinea pig IgG, and Alexa 594-conjugated goat anti-mouse IgG, Invitrogen]. Tissue sections were then washed three times with TBS and mounted with Hoechst 33342. Images were acquired and quantified under a Carl Zeiss fluorescence microscope with a 10× objective lens. All images from the same experiment were acquired with the same settings, including fluorescence intensity, acquisition time, and image resolution. The immunoreactivity of pERK and the overlap between pERK and neuron markers (SP, CGRP, IB4 or N52) were assessed using Fiji (ImageJ, NIH) software, with the experimenter blinded to treatment and/or genotype. Background levels were obtained from sections incubated without primary antibody. To determine the percentage of positive neurons in DRGs, the number of labeled neurons (≥3 times of background staining) was divided by the total number of neurons. For colocalization analysis, every positive cell identified in coimmunostaining study with pERK and neuron markers within a tissue section was labeled with a number, and those cells exhibiting positive immunoreactivity for two antibodies were considered double-positive.

Retrograde tracing with fluoro-gold (FG). To determine whether expression of pERK differed in afferent neurons of different tissue types, populations of DRG neurons projecting to cutaneous and muscle tissues were retrogradely labeled in vivo by using a tracer[54, 55]. Fluoro-Gold (10 μL, 2% in 0.9% saline) was injected into 1) the plantar skin of both hind paws subcutaneously to identify cutaneous afferent neurons, and 2) bilateral gastrocnemius muscles to identify muscular afferent neurons. Injections involved a number 30 needle over 5 min at every injection site for full dissipation through the targeted tissues. In every injection experiment, the needle was carefully held in place to avoid erroneous staining of the adjacent tissues. After removing the needle from the muscle, the injection site was washed with saline and dried carefully to minimize the spread of FG to adjacent skin. Application of RISS was then performed 1 week after the completion of FG injection. Immunoactivity of pERK in neurons of L4 DRG was counted and further related to the subtypes of FG-labeled neurons. Immunoreactive cell counting and the overlap between pERK and FG were analyzed using Fiji (ImageJ, NIH) software as described above.

Lipidomics

Untargeted lipidomic analysis. Sample preparation and processing. Serum samples from control mice as baseline and RISS mice at P4 (acute phase), P14 (subacute phase), P28 (late phase) and P56 (recovery phase) were extracted and analyzed. An aliquot of 100 μL serum from each mouse was extracted in a 1000-μL mixture of methanol and chloroform (1:2) with homogenizer (Geno/Grinder 2010 Spex SamplePrep; Metuchen, NJ, US). After centrifugation (4° C., 15000 g; 5 min), 600 μL lower layer fluid was collected. The serum extracts were then pooled and evaporated by nitrogen gas, and later reconstituted with 120 μL of 100% methanol. After centrifugation (15000 g; 5 min), the supernatant was then filtrated with a 0.22-μm filter (Minisart RC-4; Sartorius, Germany). Lipid profiling of serum sample involved high-performance liquid chromatography coupled with quadrupole time-of-flight mass spectrometry (HPLC-QTOF-MS). An Agilent 1290 UHPLC system with an Agilent ZORBAX Eclipse Plus C18 column (2.1×100 mm, 1.8 μm; Agilent Technologies, Santa Clara, CA, USA) was coupled with a Bruker maXis quadrupole TOF mass system (Bruker Daltonics, Bremen, Germany) for mass detection. MS data were then analyzed by using the molecular feature extraction algorithm of the Agilent MassHunter Workstation software (Agilent Technologies, Santa Clara, CA, USA). The HPLC-QTOF-MS data from each experiment were processed by using True Ion Pick (TIPick) software for peak detection, alignment, and normalization as described[56]. The metabolites were identified by using the in-house library with m/z, retention time, and ion abundance.

Triple quadrupole mass spectrometry (QqQ MS) for absolute quantitative analysis of target lipids. Targeted analysis of LPC16:0, LPC18:0 and SM(d18:1/18:0) was measured by using an Agilent-1200 liquid chromatography system coupled to an Agilent-6410 QqQ MS with an ESI interface. In brief, lipids were chromatographically separated on a CSHTM 1.7 μm, 1.0 mm×10 cm C18 column (Waters) with temperature of the column set at 55° C. The flow rate was set to 0.1 mL/min over 20 min, and the mobile phase A consisted of 10 mM $NH_4HCO_2$ in ACN/$H_2O$ (60/40) and 0.1% formic acid (0.1% v/v) and mobile phase B of 10 mM $NH_4HCO_2$ in IPA/ACN (90/10) and 0.1% formic acid (0.1% v/v). The parameters of mass detection were $N_2$ flow rate, 10 L/min; gas temperature, 350° C.; nebulizer gas pressure, 50 psi; capillary voltage 4000 V in positive mode; fragmentor, 135 V with collision energy 15 eV. Mass Hunter software was used for data acquisition. Quantitation involved using multiple reaction monitoring (MRM) for the m/z transitions as follows: 496.6 to 104.0 and 496.6 to 86.1 for LPC16:0; 524.4 to 104.1 and 524.4 to 86.1 for LPC18:0; 731.6 to 185.1 for SM (d18:1/18:0).

Lipidomic profiling for relative quantitative analysis. Lipids were identified by comparing the LC/MS profiles of the metabolites of interest to that of a standard compound analyzed with identical conditions, and their relative abundance among samples was further evaluated. In brief, lipids were separated on an Acquity HPLC separation module (Waters Corp., MA, USA) incorporating a CSH 1.7 μm, 1.0 mm×10 cm C18 column (Waters) under gradient conditions at a flow rate of 0.1 mL/min over 20 min at 55° C. The mobile phase A consisted of 10 mM $NH_4HCO_2$ in ACN/$H_2O$ (60/40) and 0.1% formic acid (0.1% v/v) and mobile phase B of 10 mM $NH_4HCO_2$ in IPA/ACN (90/10) and 0.1% formic acid (0.1% v/v) for molecule protonation. Mass spectrometry was performed with a Xevo G2 qTof (quadrupole time-of-flight mass spectrometer, Waters) instrument equipped with an electrospray ionization probe (ESI, Waters) interface, with 3 kV capillary voltage and operated in the data-independent collection mode ($MS^E$). Parallel ion fragmentation was programmed to switch between low (4 eV) and high (35 to 55 eV) energies in the collision cell, and data were collected from 200 to 1600 m/z with leucin (Sigma Aldrich, m/z 556.2771) as the separate data channel lock mass calibrant. Lipid standards purchased from Avanti Polar Lipids Inc. were used to confirm the LC/MS graph results, including LPC16:0 (retention time=1.55, m/z=496.3427), LPC18:0 (retention time=2.07, m/z=524.3737), and SM (d18:1/18:0) (retention time=8.06, m/z=731.6062). Collected data were processed with Progenesis QI (Waters) for lipid identification and relative quantitative analysis.

Statistics

Animal and clinical study. Data are presented as mean±SEM and were analyzed by using Prism v7 (GraphPad Software, La Jolla, CA, USA). A two-tailed t test was used to determine significance between two groups, and F-tests for equality of variance were used for all t tests to compare variances. One- or two-way ANOVA followed by the appropriate multiple-comparison tests was used for comparing more than two groups as appropriate. $P<0.05$ was considered statistically significant.

Clinical study. Sample size calculations were performed using the statistical program G* Power (version 3.1.9.2), with a 0.05 significance level ($\alpha=0.05$) and a power of 80% ($\beta=0.20$). One- or two-way ANOVA followed by the appropriate multiple-comparison tests was used for comparing more than two groups as appropriate. Spearman rank correlation analysis was used to assess the relevance between two parameters. $P<0.05$ was considered statistically significant.

Lipidomics study. The changes in peak intensity between groups were compared by fold-change analysis. Statistical differences between control and RISS groups in untargeted lipidomics were assessed by the Mann-Whitney U test with SPSS v20. $P<0.05$ was considered statistically significant. The unsupervised principal component analysis (PCA) was used to determine the natural grouping of samples. To identify differentially expressing lipids for RISS, the supervised orthogonal partial least squares discriminant analysis (OPLS-DA) model with the control and P4 groups was constructed. A significance plot was then created to identify highly discriminative compounds for the P4 group based on their contribution to the variation and correlation within the data set. Both PCA and OPLS-DA analyses involved using MetaboAnalyst 3.0.

Clinical Study

The clinical prospective research was carried out in accordance with the Declaration of Helsinki and was approved by the institutional review board of Kaohsiung Medical University Hospital [KMUHIRB-(I)-20170012]. Adult patients with chronic widespread pain in the outpatient department of the hospital were consecutively enrolled over 1 year from 2018 July to 2019 June in the neurological clinic at KMUH. Participants were interviewed and evaluated by an experienced neurologists (CHH), and those fulfilling the 2010 American College of Rheumatology criteria for FM were recruited. Age- and sex-matched individuals without chronic pain and mood disorders were also prospectively recruited as healthy controls (HC). Clinical information was acquired by personal interview and questionnaire, and blood samples were collected for biochemistry and lipidomic analysis. To evaluate the clinical presentation and metabolomic phenotypes without pharmacotherapeutic interference, only patients with newly diagnosed primary FM and without current antidepressant and anti-epileptic treatment were recruited for further analysis. All participants were well informed and provided written consent. All patients with a FM diagnosis were followed up for at least 6 months by outpatient services to ensure that no other etiology was identified.

Clinical information. The demographic and clinical data of patients and controls were obtained from questionnaires and interview by the same specialist throughout the study. All the participants had routine laboratory examination to exclude disorders that would otherwise explain the pain, including erythrocyte sedimentation rate, antinuclear antibody, rheumatoid factor, thyroid hormone, thyroid-stimulating hormone, alanine and aspartate aminotransferase, creatinine kinase, cortisol and electrolytes. Exclusion criteria for both groups included the presence of systemic rheumatological or immune disorders (such as systemic lupus erythematosus or inflammatory myositis), systemic use of corticosteroids, current pregnancy, chronic diseases under poor control (such as diabetes mellitus, hypertension) and malignancies.

The severity and diffuseness of pain symptoms were assessed with verbal rating scale for pain (VRS; 0-10) and widespread pain index (WPI) based on the American College of Rheumatology criteria for FM. The Perceived Stress Scale (PSS-10) was used to evaluate the perception of stress in individuals. To determine the disease impact and severity of FM in study subjects, the Revised Fibromyalgia Impact Questionnaire (FIQR) was employed for evaluation of life function, overall impact and symptom intensity in patients with FM.

Blood collection and analysis. Venous blood was taken from patients and controls at the first clinic visit before pharmacotherapeutic intervention and then collected in EDTA tubes. Blood was then centrifuged at 3000 rpm for 15 min at 4° C. to obtain plasma. Plasma samples were stored at −80° C. until analysis. Serum lipid peroxidation levels were determined by TBARS assay with a commercial kit (Cayman, Ann Arbor, MI).

Figure 1B:
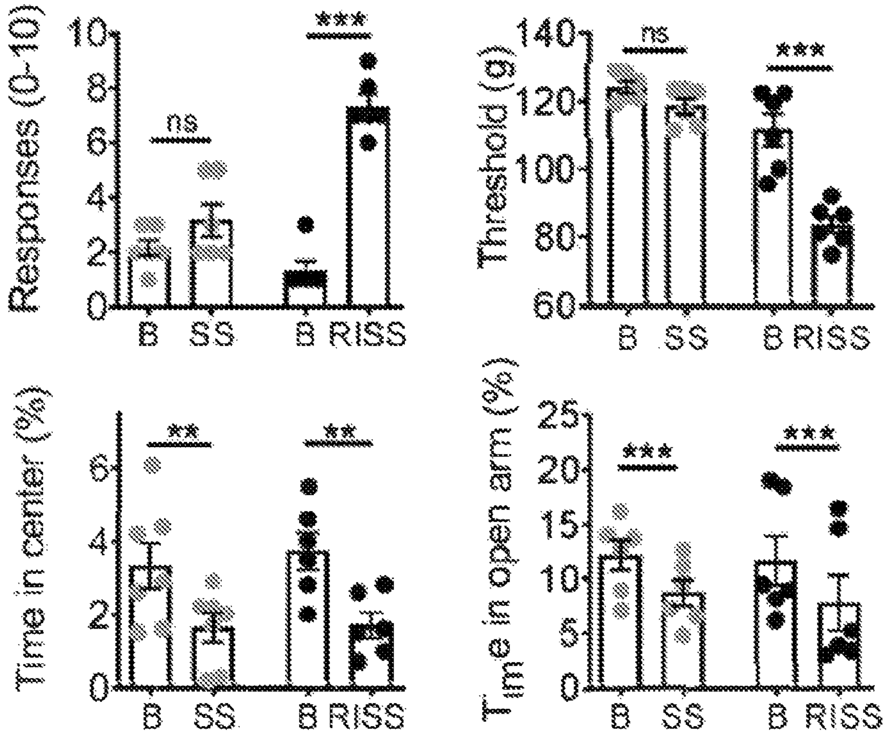
Figure 1C:
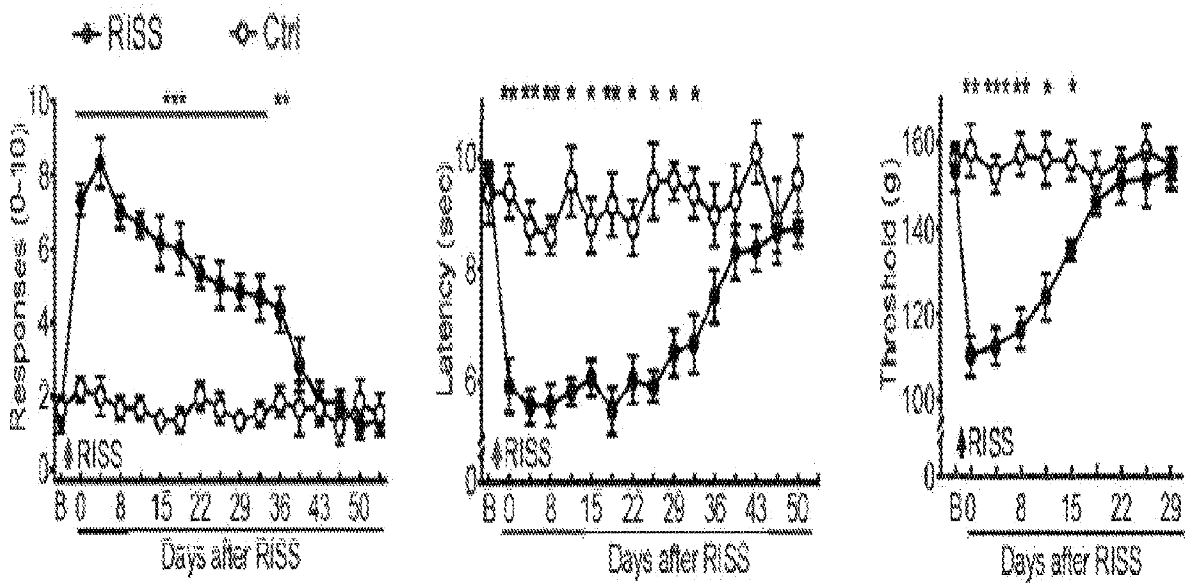
Figure 1D:
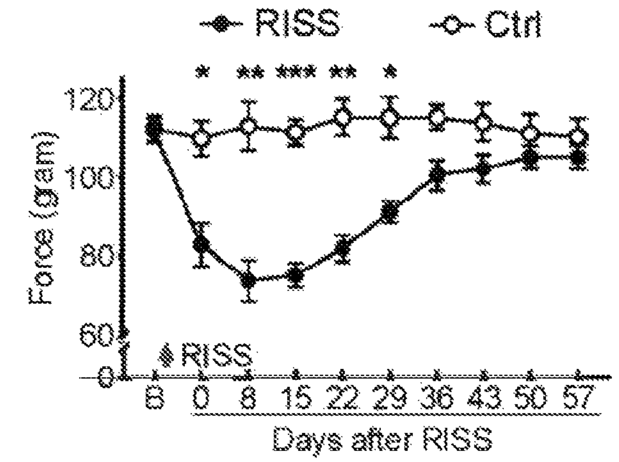
Figure 1E:
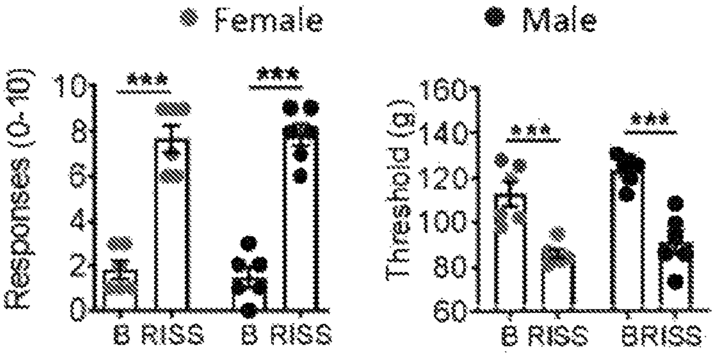
Figure 1F:
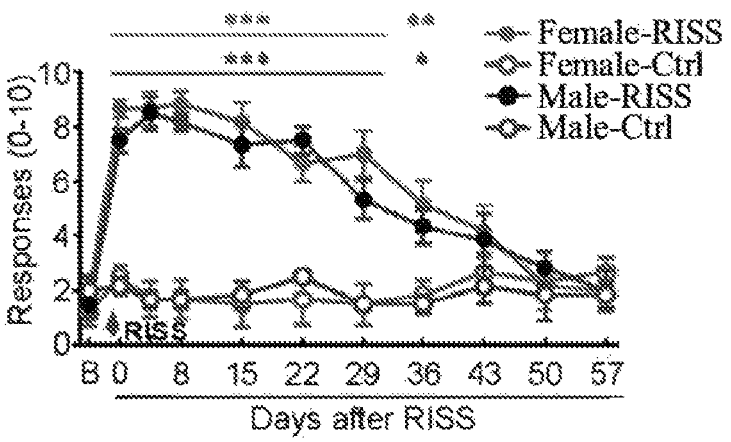

Example 1: Exposure to RISS Induces Fibromyalgia-Like Pain Behaviors in Mice In basic research of pain, repeated and intermittent challenge of stimuli are crucial for pain generation and perpetuation[11, 16-18]. Therefore, the existing SS setting was modified by increasing stimulus intensity repeatedly and intermittently from once daily to once every 3 hours for 6 times daily, carried out according to the scheme shown in FIG. 1A, and then evaluated behavioral responses. Surprisingly, the modified repeated and intermittent SS (RISS) model induced anxiety-like behaviors and also triggered evident hypersensitivity as compared with the existing model (FIG. 1B). Follow-up studies after RISS showed significant mechanical and thermal hyperalgesia lasting for more than 4 weeks, and muscle hyperalgesia for 2 weeks (FIG. C). As well, comorbid fatigue-like behaviors were observed after RISS (FIG. 1D). Mice of both sexes developed hyperalgesic behaviors after RISS without evident sexual dimorphism (FIGS. 1E and F).

Figure 1G:
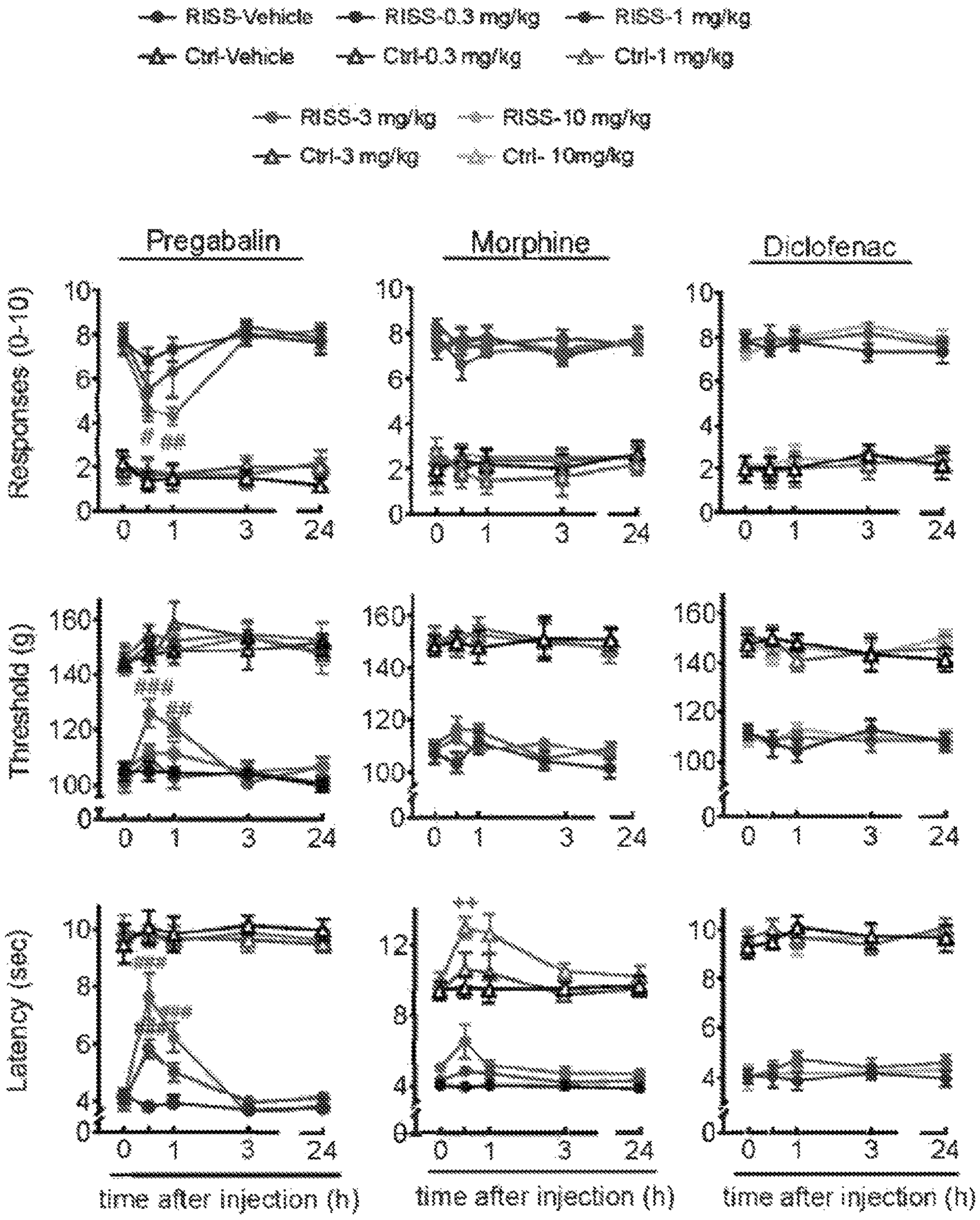

To test the predictive validity of the RISS model, analgesics (pregabalin, morphine and diclofenac) were systemically administered, and the pharmacotherapeutic effects were tested (FIG. 1G). Intraperitoneal (i.p.) injection of pregabalin dose-dependently reversed hyperalgesia, but morphine and diclofenac had no significant analgesic effects. Plasma corticosterone and epinephrine were measured to determine the RISS effects on the neuroendocrine system. Levels of both hormones were significantly increased after RISS versus controls (FIG. 6A). Hematological and serum biochemistry studies showed nonspecific findings in RISS mice as compared with controls (Table 1 below).

TABLE 1

Hematological and serum biochemical data in control and RISS mice at post-RISS day 0 (n = 5 per group)

| Parameter | Control | RISS | Units |
|---|---|---|---|
| WBC count | 6.5 ± 1.1 | 7.4 ± 0.5 | K/uL |
| Neutrophils | 13.0 ± 4.2 | 13.1 ± 1.8 | % |
| Lymphocytes | 84.5 ± 4.3 | 83.7 ± 1.8 | % |
| Monocytes | 0.4 ± 0.0 | 0.5 ± 0.1 | % |
| Eosinophils | 2.1 ± 0.3 | 2.7 ± 0.3 | % |
| Basophils | 0.0 ± 0.0 | 0.00 ± 0.00 | % |
| RBC count | 10.2 ± 0.2 | 9.9 ± 0.1 | M/uL |
| Hemoglobin | 15.0 ± 0.2 | 14.5 ± 0.1 | g/dL |
| Hematocrit | 50.8 ± 0.9 | 48.1 ± 0.3 | % |
| Mean cell volume | 49.9 ± 0.2 | 48.8 ± 0.4 | fL |
| Mean corpuscular hemoglobin | 14.8 ± 0.0 | 14.7 ± 0.1 | pg |
| Mean cell hemoglobin | 29.6 ± 0.1 | 30.0 ± 0.1 | g/dL |
| Red cell distribution width | 23.5 ± 0.3 | 23.9 ± 0.4 | % |
| Platelet count | 895.2 ± 63.8 | 1084.2 ± 43.6 | K/uL |
| LDH | 257.8 ± 12.2 | 249.2 ± 20.8 | U/L |
| AST | 20.8 ± 1.1 | 20.2 ± 1.0 | U/L |
| ALT | 39.2 ± 1.1 | 36.2 ± 1.3 | U/L |
| CPK | 156.6 ± 11.7 | 164.0 ± 29.3 | U/L |
| BUN | 28.0 ± 1.9 | 21.1 ± 0.5 | mg/dL |
| Cr | 0.1 ± 0.0 | 0.1 ± 0.0 | mg/dL |
| CKMB | 106.0 ± 10.5 | 83.8 ± 11.7 | U/L |

Samples were obtained from cardiac puncture and commercially analyzed (Fuji DRI-CHEM 4000i).
Data are expressed as the mean ± SEM.

Example 2: RISS Induces Activation of Primary Afferent Neurons

To investigate the histopathology of RISS-treated mice, hematoxylin and eosin staining of muscle tissues was used. Gastrocnemius muscle sections in RISS mice showed intact myofascial structure and vascular channels with no evidence of tissue injury or inflammation (FIG. 6B). Also, serum levels of tumor necrosis factor-alpha (TNF-α), an inflammatory cytokine, showed no significant difference between groups (FIG. 6C). The intramuscular pH values did not differ between RISS mice and controls (FIG. 6D). Given that histopathological studies demonstrated no local tissue damage, immunohistochemical analysis of L4 dorsal root ganglia (DRG) was further used to probe nociceptive processing. As a surrogate marker of nerve injury, activating transcription factor 3 (ATF-3) was first examined, but the immunoreactivity remained negative (FIGS. 6E and 6F).

Figure 2A:
FIGS. 2A to 2G show upregulated expression of phosphorylated extracellular signal-regulated kinase (pERK) after RISS in lumbar dorsal root ganglia (DRG) of mice at post-RISS day 0.
Figure 2B:
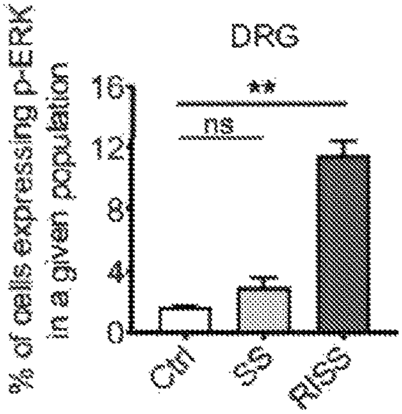
Figure 2C:
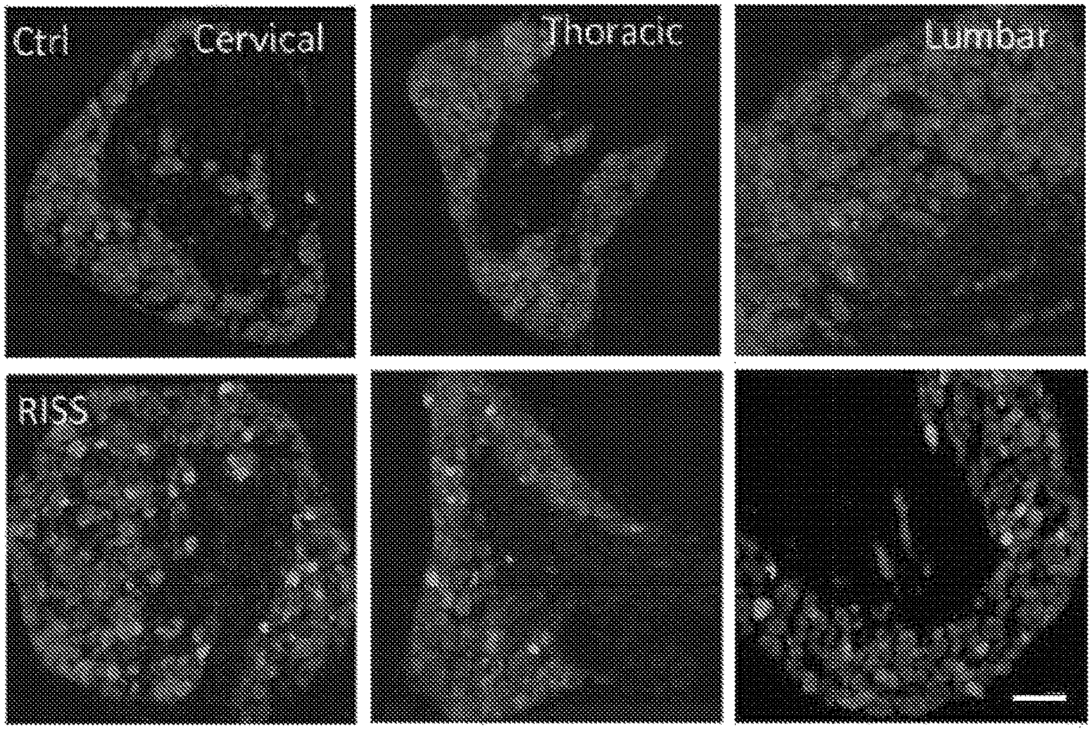
Figure 2D:
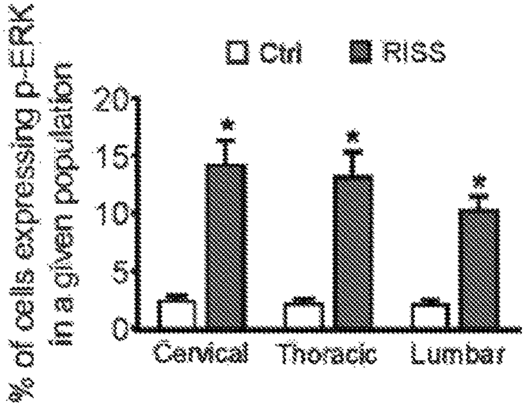

Phosphorylated extracellular signal-regulated kinase (pERK) as a marker of neuronal activation was further examined to determine whether the hypersensitivity responses originated from the peripheral nociceptive input (FIG. 2A). pERK expression was significantly higher in the RISS than control group, with no difference between the SS and control groups (FIG. 2B). To evaluate the distribution range of the activated signals, pERK expression in DRG neurons from different spinal segments, including cervical, thoracic and lumbar regions was further examined (FIGS. 2C and 2D). As compared with controls, all sampled RISS DRG neurons showed increased pERK expression, which suggests the widespread distribution of signaling activation after RISS.

Figure 2E:
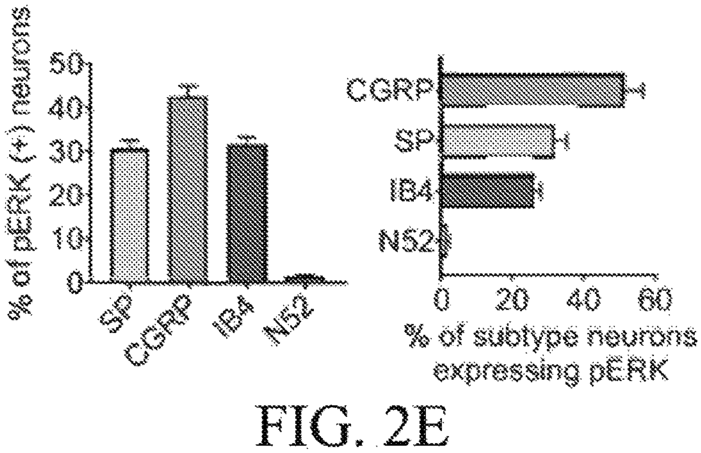
Figure 2F:
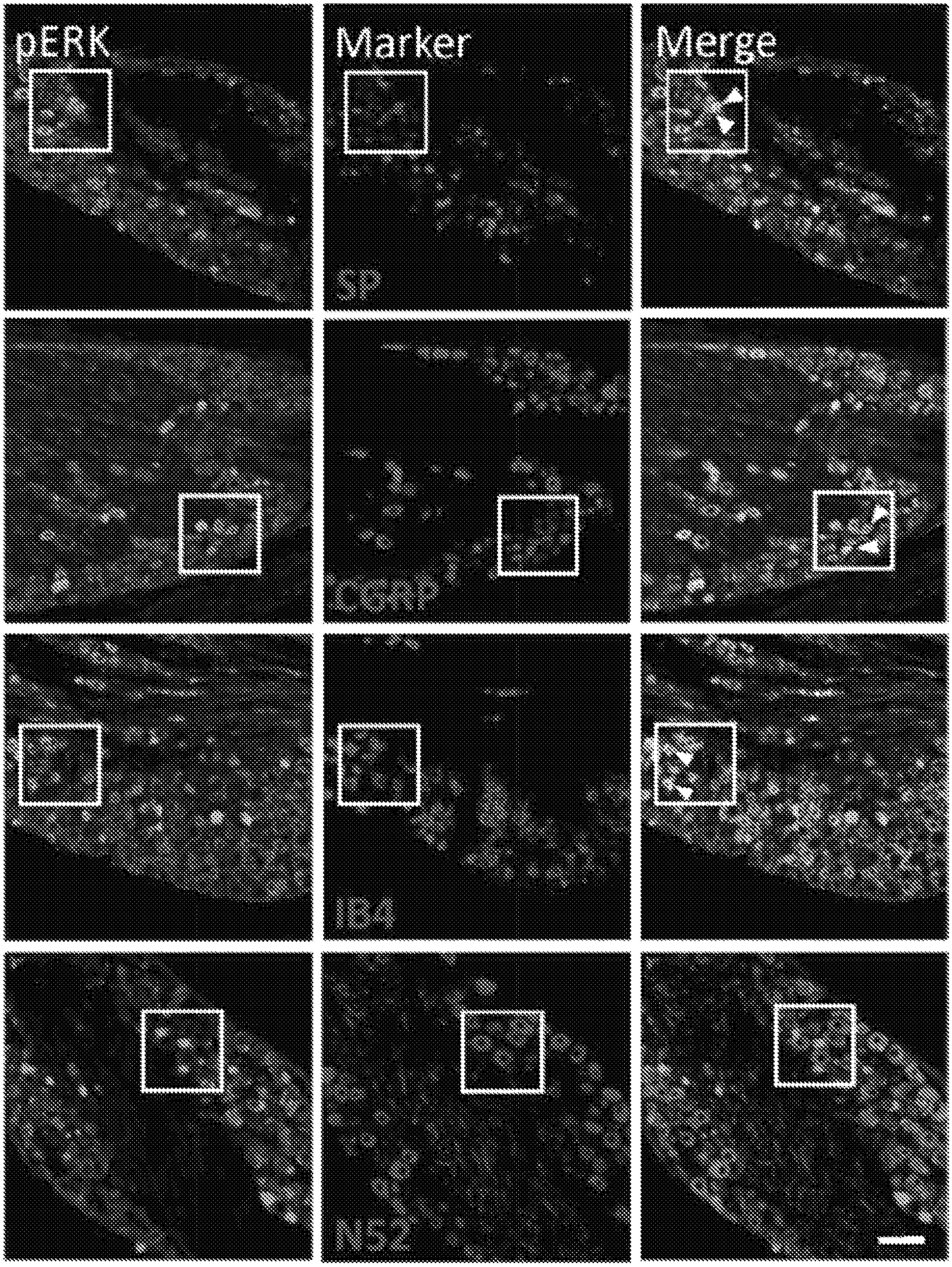
Figure 2G:
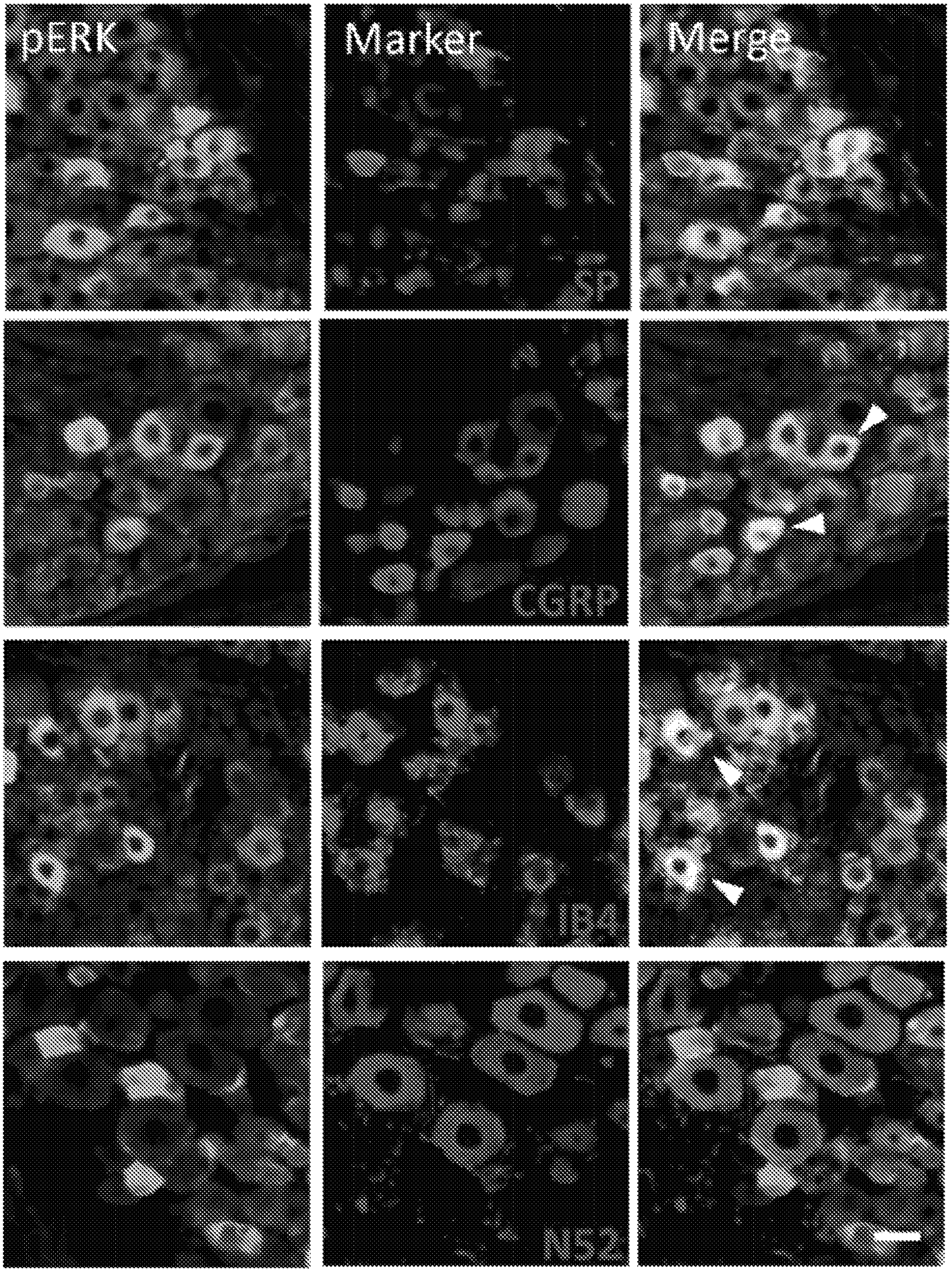

To further map the signaling distribution in sensory neuron subtypes, various neuronal markers were co-stained with pERK (FIGS. 2E, 2F and 2G). Of the pERK-positive DRG neurons, 42.6%, 30.6%, and 31.5% colocalized with calcitonin gene-related protein (CGRP), substance P (SP) (both markers of peptidergic nociceptive neurons), and isolectin B4 (IB4; a marker for nonpeptidergic neurons), respectively. Conversely, 51.4%, 32.1% and 26.2% of CGRP-, SP-, and IB4-positive neurons, respectively, immunostained for pERK. In comparison, few pERK-positive neurons (1.37%) co-stained with N52 (a marker for myelinated neurons), and only a small amount of N52 positive neurons (2.0%) colocalized with pERK. The unique distribution patterns of pERK suggested that the nociceptive activation by RISS mainly involved small unmyelinated C-fibers but not large myelinated A-fiber neurons.

To determine whether the RISS-induced pERK expression was specific to afferent neurons of different anatomic distributions, populations of DRG neurons projecting to muscle and paw skin were retrogradely labeled with fluorogold (FG) (FIGS. 7A and 7B). The immunoreactivity of pERK after RISS was analyzed and it was related to the subtype classifications of the FG-labeled neurons. Colocalization analysis showed comparable pERK expression in afferent neurons of muscle (35.7%) and paw skin (32.8%) ($p=0.564$), so the RISS-induced nociceptive activation was not exclusive to muscular tissue but was possibly systemic. To test whether RISS would induce neuron activation in the spinal cord that may contribute to central sensitization, immunoreactivities of pERK (FIGS. 7C and 7D) and c-fos (FIGS. 7E and 7F) in that spinal cord of RISS mice were examined, and both showed significantly increased expression as compared with controls.

Example 3: RISS Incurs Endogenous Oxidative Stress and Results in Lipid Oxidization Both human and animal studies indicated that exposure to psychological distress is closely related to increasing oxidative stress[1, 21-23]. Patients with FM are under higher oxidative status than healthy controls, as indicated by significantly higher plasma lipid peroxidation assessed by malondialdehyde (MDA) level[24, 25]. To assess the RISS effect on oxidative status, the same method was used to assay lipid oxidization in RISS mice (FIG. 3A). After RISS exposure, MDA level was significantly higher in stressed than control mice, which suggests that RISS results in excessive oxidative stress and ROS-dependent lipid damage.

To investigate the potential source of the oxidative stress, fluorescent indicators (CM-$H_2$DCFDA) was used to detect the presence of ROS in peripheral tissue. Given that FM is characterized by a myalgia pattern, it was first hypothesized that oxidative stress originates in skeletal muscles and participates in pain generation. Unexpectedly, muscular tissues from the RISS mice showed comparable levels of fluorescence intensity as their controls, which suggests no ROS accumulation in the muscle tissues (FIGS. 3B and 3C).

Figure 3D:
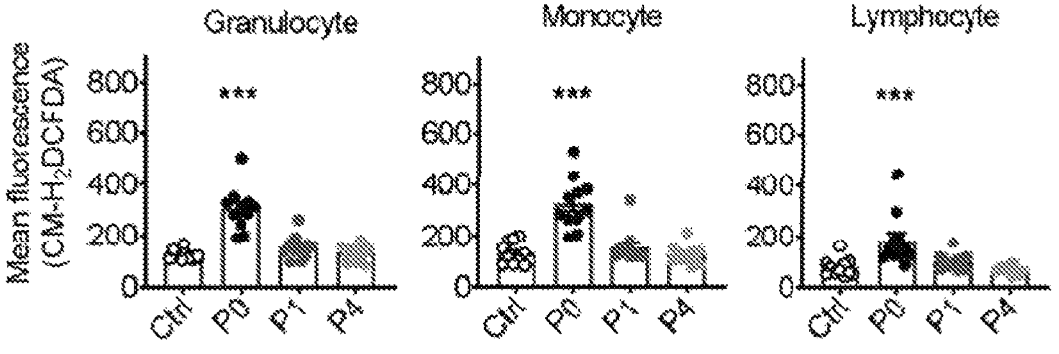
FIG. 3D shows the time course of the RISS effects on blood leukocyte oxidative status (n=11 per group; ANOVA). Intracellular ROS levels were measured by fluorescence intensity with CM-$H_2$DCFDA staining using flow cytometry.
Figure 3E:
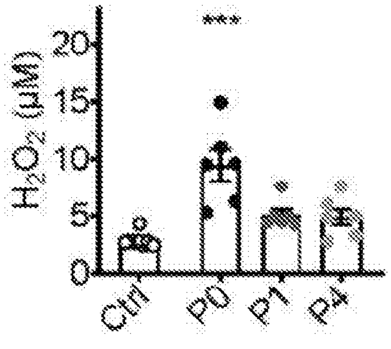
FIG. 3E shows the time course of the RISS effects on serum $H_2O_2$ level (n=6 per group; ANOVA).

Leukocytes function to generate ROS for phagocytic purposes, so ROS indicators were further used to examine ROS levels in blood leukocytes by flow cytometry (FIG. 3D). Immediately after RISS, ROS levels increased significantly in all leukocyte populations, and soon decreased to baseline in 24 hours. In addition to excessive oxidative stress within leukocytes, RISS also resulted in increasing serum level of hydrogen peroxide ($H_2O_2$) (FIG. 3E).

Figure 3F:
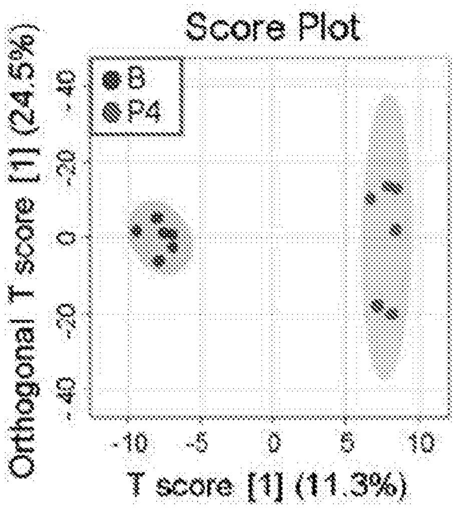
FIG. 3F shows the score plot of orthogonal partial least squares discriminant analysis (OPLS-DA) distinguishing basal (B) and RISS (P4) groups based on serum lipidomic profiling ($R^2Y=0.71$, $Q^2=0.166$) (n=6 per group).
Figure 3G:
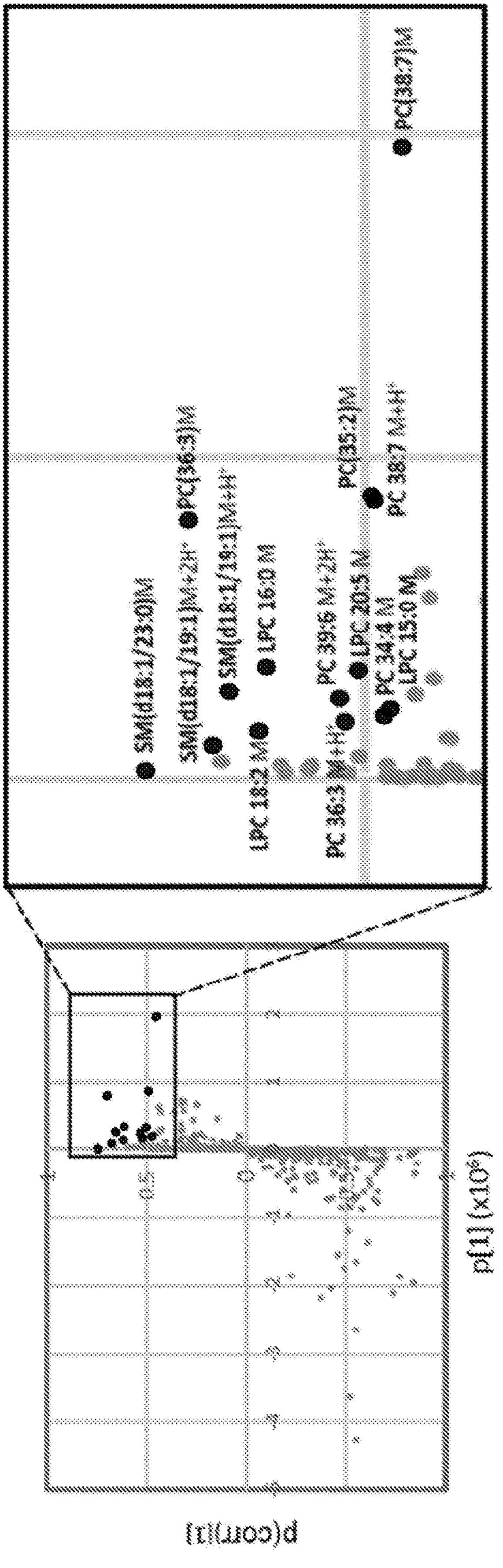
FIG. 3G shows the S-plot of OPLS-DA and the differentiating metabolites identified for P4 (marked as darker circles).

To identify the differentially expressing lipids at an acute phase of RISS (P4), the supervised orthogonal partial least squares discriminant analysis (OPLS-DA) model with control and P4 groups was used. The OPLS-DA score plot showed a clear partition in peak clusters between the basal and P4 groups (FIG. 3F). The $R^2Y$ and $Q^2$ of the resulting model were 0.166 and 0.71, respectively. The S-plot was conducted to identify discriminative metabolites that contribute to differentiate RISS from control treatment (FIG. 3G).

In pain research, repeated exposure to stimulus seems critical in pain chronification[11, 16, 17]. To probe the repetitive effect of stress on pain development, mice were given single-day stimuli of intermittent SS (SISS) rather than repeated stimuli of RISS (FIG. 8A). As compared with RISS, SISS caused only transient pain responses instead of chronic changes (FIG. 8B). Like RISS, SISS induced transient augmentation of oxidative stress (FIGS. 8C to 8E). The results suggested that both modes of stimuli induced excessive oxidative stress and acute hypersensitivity, but only repeated stimuli resulted in hypersensitivity chronification.

Example 4: Lipidomics Implicates Upregulation of LPC16:0 after RISS

Excessive oxidative stress causes direct damage to lipids[26, 27]. Clinical metabolomics identified upregulated products of lipid oxidization in FM patients, suggesting that these oxidized lipids might participate in algogenesis[28]. However, the roles of these dysregulated lipids in pain development remain inconclusive. To explore the mechanism of the RISS model, untargeted mass spectrometry-based metabolomic study with serum of RISS mice was used. It was first hypothesized that certain dysregulated metabolites exist during the pain period and result in long-term nociceptive activation. To identify potential algesic substances, time-series lipidomic analysis at different times was used in accordance with the temporal course of pain behavioral changes: acute (P4), subacute (P14), chronic (P28), and recovery (P56) stages. Serum lipidomic analysis based on UPLC-QTOF-MS was used to investigate the nociceptive mechanism of RISS-induced pain at different time, including basal status (B), acute (P4), subacute (P14), chronic (P28), and recovery (P56) stages.

To visualize the sample distribution of the multiple variate patterns, principle component analysis (PCA) was performed. Two principal components (PC1 and PC2) were calculated to build the unsupervised scatter plot. At the times of P4, P14, P28 and P56, PC1 and PC2 together explained 52.4%, 46.5%, 41.8%, and 43.2% of the total variance, respectively. No outlier or intrinsic distribution was identified by the score plot, and thus all samples were recruited for further analysis (FIG. 9A). Changes in peak intensity of all variables between the RISS and basal groups were compared by fold-change analysis, and lipids with significantly increasing levels at each time were screened out, as shown in Table 2 below.

TABLE 2

Upregulated lipids and their fold changes in peak intensity at different times after RISS

| Lipid ID | Ion (m/z) | Adduct | Fold change (day post RISS/control) P4 | P14 | P28 | P56 |
|---|---|---|---|---|---|---|
| LPC 16:0 | 496.3399 | M | 1.37* | 1.11 | 1.20 | 1.05 |
| LPC 18:2 | 520.3399 | M | 1.35** | 1.07 | 1.13 | 1.01 |
| SM (d18:1/19:1) | 744.6066 | $M + H^+$ | 1.31* | 1.06 | 1.29* | 1.27 |
| SM (d18:1/19:1) | 745.6066 | $M + 2H^+$ | 1.30* | 1.03 | 1.29* | 1.25 |
| SM (d18:1/23:0) | 801.6852 | M | 5.24* | 0.83 | 4.31 | 2.46 |
| PC 36:3 | 784.5853 | M | 1.19** | 1.01 | 1.05 | 1.02 |
| Cer (d18:1/22:0) | 622.6141 | M | 0.98 | 1.14* | 0.79 | 1.00 |
| Cer (d18:1/23:0) | 636.6297 | M | 1.02 | 1.18* | 0.79 | 1.06 |
| Cer (d18:1/24:0) | 650.6454 | M | 1.03 | 1.27** | 0.85 | 1.07 |
| LPC 15:0 | 482.3242 | M | 1.14 | 0.95 | 1.39* | 1.38** |
| SM (d18:1/24:1) | 813.6849 | M | 0.97 | 1.32 | 1.56** | 1.53** |
| PC 35:4 | 768.5539 | M | 1.11 | 0.90 | 1.40* | 0.81 |
| LPC 17:0 | 511.3555 | $M + H^+$ | 1.08 | 1.06 | 1.03 | 1.14* |
| LPC 19:0 | 538.3868 | M | 1.15 | 1.19 | 1.21 | 1.24* |
| PC 34:1 | 760.5853 | M | 0.89 | 0.99 | 1.03 | 1.05* |
| PC 36:4 | 782.5696 | M | 1.08 | 1.07 | 1.12 | 1.22** |
| PC 36:5 | 781.5539 | $M + H^+$ | 1.17 | 1.13 | 1.17 | 1.31** |

Serum lipids were analyzed at post-RISS day 4 (P4), day 14 (P14), day 28 (P28), and day 56 (P56). Fold changes were calculated by dividing the mean of the peak intensity of each metabolite from RISS (P4, 14, 28 and 56) and basal groups (n = 6 in each group). RISS and basal groups were compared by Mann-Whitney test.
*$p < 0.05$,
**$p < 0.01$.
LPC: lysophosphatidylcholine. SM: sphingomyelin. PC: phosphatidylcholine. Cer: ceramide.

The identified lipids were mainly LPCs, phosphatidylcholines (PCs), sphingomyelin (SM) and ceramides. Their changing trends of intensity over time were further related to the course of behavioral changes. Although specific lipids showed differential intensity at each stage, none of the dysregulated metabolites retained the intensity throughout the pain period from P4 to P28.

Given no metabolite with enduring intensity, it was further hypothesized that dysregulated metabolites for algogenesis are elicited transiently during RISS and then decomposed over time. Accordingly, the targeted metabolites should be at highest levels at the acute stage (P4) and thus more detectable than afterward. To identify the potential targets, orthogonal partial least squares discriminant analysis (OPLS-DA) with the basal and P4 groups was used to classify the metabolic phenotypes, and an S-plot was created to determine the discriminative lipids for P4 (FIGS. 3F and 3G). Among the 14 metabolites selected by OPLS-DA, 6 showed a significant increase in peak intensity based on fold-change analyses (Table 1). In addition to considering their discriminative abilities, the variation patterns of lipids from P4 to P56 were considered; the lipids with variation trends of timely emergence after RISS and gradual attenuation over time were preferentially recruited for advanced investigation. In summary, lipids with the following conditions were identified as targeted metabolites: (1) high discriminative values for P4 by S-plot; (2) significant incremental changes by fold-change analysis; and (3) accordant variation in trends of intensity with the pain behavioral changes.

Among the detected lipids, LPC16:0, LPC18:2, and PC36:3 were eligible candidates, with upregulation by 1.37-, 1.35-, and 1.19-fold basal status, respectively (FIGS. 9B to 9E). From the temporal frame of pain behaviors, dysregulated metabolites for nociceptive activation should be detectable as early as at P0. Therefore, the lipidomic profiling to the hyper-acute phase (P0) was further pushed forward to assess the timely performance of the candidates. The PCA score plot was used again to visualize the sample distribution. Two principal components were calculated to build the unsupervised scatter plot and together explained 55.5% of the total variance. A clear partition in peak clusters was already observed between the basal and P0 groups in the unsupervised scatter plot. No outlier was identified by the score plot, and thus all samples were recruited for analysis (FIG. 9F).

Lipids with significant upregulation at P0 were screened out (as shown in Table 3) and referred to the candidates from P4.

TABLE 3

Upregulated lipids and their fold changes in peak intensity at P0 after repeated and intermittent sound stress (RISS)

| Lipid ID | Ion (m/z) | Adduct | Fold change (post RISS/control |
|---|---|---|---|
| LPC 16:0 | 496.3399 | M | 1.47** |
| LPC 18:0 | 525.3712 | $M + H^+$ | 1.47* |
| LPC 18:3 | 518.3242 | M | 1.11** |
| LPC 20:2 | 548.3713 | M | 1.19* |
| LPC 20:5 | 542.3242 | M | 1.31** |
| SM (d18:1/18:0) | 731.607 | M | 2.12** |
| SM (d18:1/20:0) | 759.6383 | M | 1.86** |
| SM (d18:1/20:1) | 757.6223 | M | 1.76** |
| SM (d18:1/21:0) | 773.6539 | M | 1.67** |
| SM (d18:1/22:0) | 788.6696 | $M + H^+$ | 1.59** |
| SM (d18:1/22:1) | 785.6536 | M | 1.52** |
| SM (d18:1/23:0) | 802.6852 | $M + H^+$ | 1.40* |
| SM (d18:1/24:0) | 816.7009 | $M + H^+$ | 1.23* |
| Cer (d18:1/22:0) | 622.6141 | M | 1.35** |
| Cer (d18:1/23:0) | 636.6297 | M | 1.19** |
| PC 34:1 | 761.5853 | $M + H^+$ | 1.06** |
| PC 36:4 | 782.5696 | M | 1.17** |
| PC 36:5 | 780.5539 | M | 6.79** |
| PC 38:2 | 814.6324 | M | 1.13** |

TABLE 3-continued

Upregulated lipids and their fold changes in peak intensity at P0 after repeated and intermittent sound stress (RISS)

| Lipid ID | Ion (m/z) | Adduct | Fold change (post RISS/control |
|---|---|---|---|
| PC 39:6 | 820.5852 | M | 1.34* |
| PC 40:4 | 838.6322 | M | 1.50** |
| PI 38:4 | 905.6001 | M + $NH_4^+$ | 1.18** |

Serum samples were collected immediately after RISS procedure (P0, hyper-acute stage) for lipidomic analysis. Fold changes were calculated by dividing the mean of peak intensity of each metabolite from P0 and basal groups (n = 6, each group). RISS and basal groups were compared by Mann-Whitney U test.

*p < 0.05,

**p < 0.01.

LPC: lysophosphatidylcholine. SM: sphingomyelin. PC: phosphatidylcholine. PI: phosphatidylinositol.

Figure 3H:
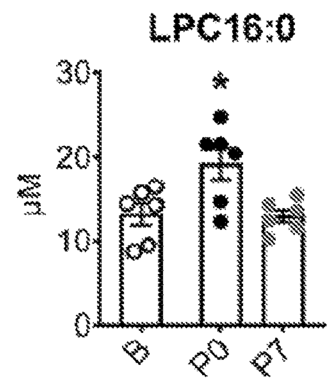
FIG. 3H shows the quantitative analysis of LPC16:0 by selective reaction monitoring triple quadrupole mass spectrometry (n=6 per group; ANOVA).

Among the three candidates, only LPC 16:0 showed accordantly incremental change (1.47-fold; p=0.002) and thus was recruited for further quantitative analysis. Because all the upregulated metabolites at P0 are potential pain initiators, the metabolites with significant increase in level with available calibration standards, including LPC18:0 and SM(d18:1/18:0), were also recruited for quantitative profiling. Quantitative analysis revealed a significant upregulation of LPC16:0 (1.45-fold; p=0.019) but not LPC18:0 (1.07-fold; p=0.877) or SM(d18:1/18:0) (0.75-fold; p=0.543) (FIGS. 3H and 9G).

Example 5: Repeated LPC16:0 Injection Induces Chronic Hyperalgesia by Activating ASIC3

Figure 3I:
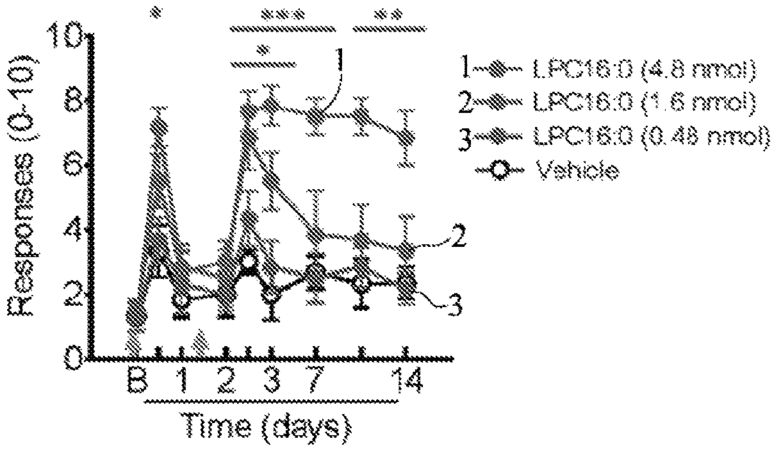
FIG. 3I shows the dose-dependent effects of repeated LPC16:0 injection on wild-type (WT) mice. Mice received two intramuscular injections (1 day apart) of neutral saline containing LPC16:0 (4.8 nmol, 1.6 nmol, and 0.48 nmol) or vehicle. Mechanical hypersensitivity was assessed by the von Frey test. Arrows: LPC16:0 injection (n=6 per group; 2-way ANOVA).
Figure 3J:
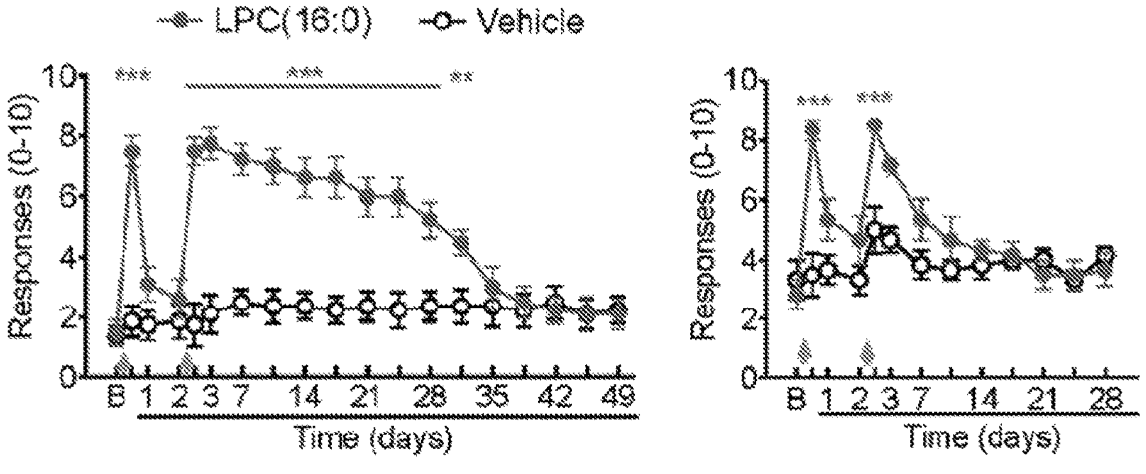
FIG. 3J shows repeated i.m. LPC16:0 injection induced chronic mechanical hyperalgesia as assessed by von Frey test (n=8) (left graph), while repeated intraplantar LPC16:0 injection only induced transient hyperalgesia rather than chronic behavioral changes (n=6) (right graph) (Both ANOVA). In each case, WT mice received two injections of neutral saline containing LPC16:0 (4.8 nmole) or vehicle (arrows).

LPCs participate in pain signaling and function as precursory nociceptive substances[29, 30]. To determine whether LPC16:0 contributes to pain development, LPC16:0 was injected into the left hindlimb of WT mice via the intramuscular or intraplantar route, followed by evaluation of mechanical hypersensitivity. Intramuscular injection of LPC16:0 dose-dependently evoked hyperalgesic responses (FIG. 3I). Single intramuscular LPC injection induced transient bilateral hyperalgesia, and repeated intramuscular injection 2 days apart induced long-lasting hyperalgesic changes (FIG. 3J). By comparison, vehicle-treated mice showed no mechanical hypersensitivity. Immunostaining analysis showed increased pERK expression after LPC injection as compared with vehicle treatment (FIGS. 10A and 10B). Of note, intramuscular administration of LPC16:0 not only evoked nociceptive activation but also triggered a hyperalgesic priming-like effect as observed in repeated intramuscular acid injection pain models. Although both routes of LPC16:0 injection evoked acute hypersensitivity, only repeated intramuscular injection led to long-lasting hyperalgesic changes (FIG. 3J). Unlike LPC16:0 injection, with LPC18:0 or SM(d18:1/18:0) injection, the priming-like effects and long-lasting hyperalgesia were not observed (FIG. 10C).

ERK is known as an important contributor to central sensitization. To determine whether ERK activity participates in the hyperalgesic priming-like effects in RISS mice, intrathecal administration of U0126, a mitogen-activated ERK inhibitor, or its inactive analogue U0124 was used 30 minutes before the first LPC16:0 injection. U0126 prevented the LPC16:0-induced acute hyperalgesia, and also impeded the development of chronic hyperalgesia induced by the second LPC16:0 injection (FIG. 10D). Moreover, the analgesic effects of pregabalin, morphine and diclofenac were tested to evaluate the face validity of the repeated LPC16:0 injection model. The injected mice responded to pregabalin treatment but not morphine or diclofenac, which suggested that the LPC16:0 injection model shared similar pharmacotherapeutic features with the RISS model (FIG. 10E).

Figure 3K:
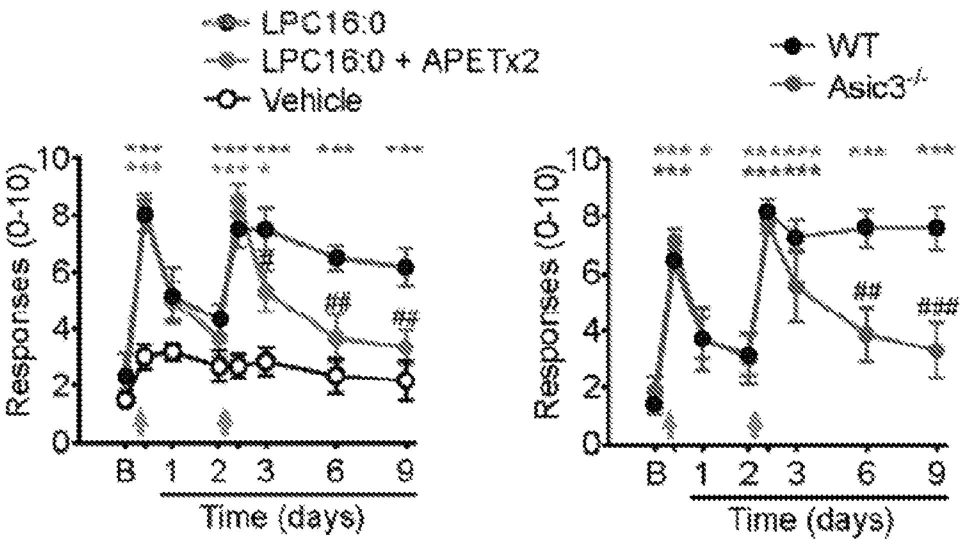
FIG. 3K shows the effects of pharmacological and genetic inhibition of ASIC3 on the chronification of mechanical hyperalgesia induced by repeated LPC16:0 injection. Left: effects of the ASIC3 inhibitor APETx2 on LPC16:0-induced chronic hyperalgesia as assessed by von Frey test (n=6). Right: effect of repeated LPC16:0 injection (i.m.) on development of chronic hyperalgesia in WT and Asic3$^{-/-}$ mice (n=7) (Both ANOVA).
Figure 3L:
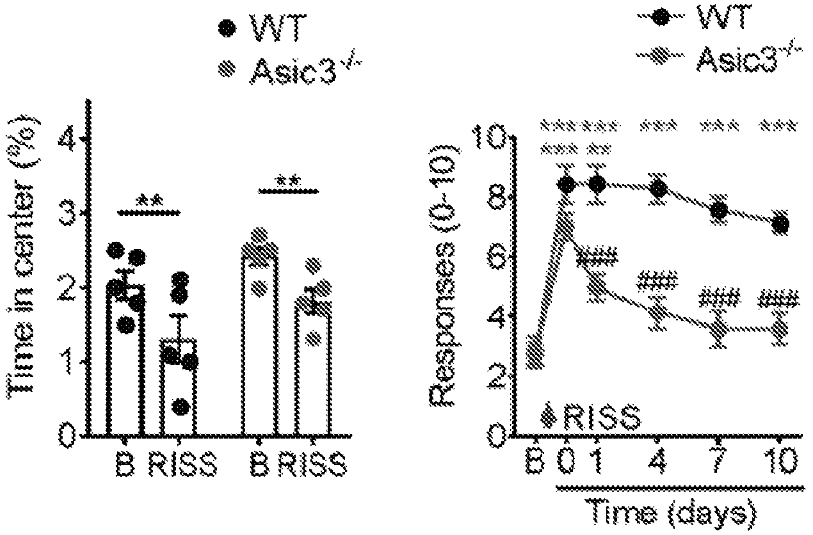
FIG. 3L shows the effect of RISS on anxiety-like and pain behavioral changes in WT and Asic3−/− mice. Left: anxiety-like behaviors measured by open field test at P0 (n=5). Right: mechanical hyperalgesia measured by von Frey test (n=7) (Both ANOVA).
Figure 3M:
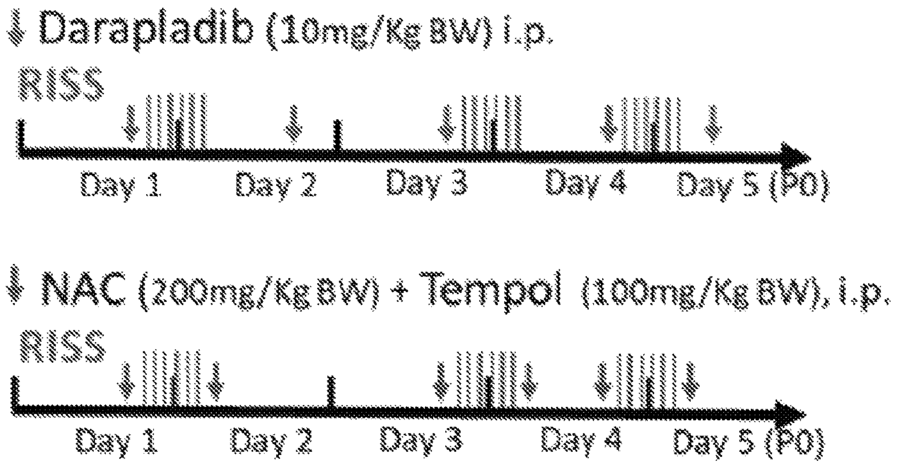
FIG. 3M shows the schematic presentation of drug administration of darapladib, and NAC+Tempol.

In the neurobiological research of chronic widespread pain, ASIC3 has been considered a research target. In addition to protons, other endogenous substances such as arachidonic acid and lactate have been reported as modulators of ASIC3. Of note, certain LPCs, such as LPC16:0 and 18:1, are able to directly activate ASIC3 channels in the absence of extracellular pH variations. To determine the contribution of ASIC3 to the RISS-induced chronic hyperalgesia, APETx2 (a selective ASIC3 antagonist) was co-injected with LPC16:0 intramuscularly, and then behavioral responses were evaluated (FIG. 3K, left). As compared with vehicle treatment, transient hyperalgesia was observed with LPC or LPC-APETx2 co-injection. However, chronic hypersensitivity was significantly reduced in APETx2-treated mice. Also, repeated intramuscular injection of LPC16:0 was given in WT and $Asic3^{-/-}$ mice, followed by evaluation of mechanical hyperalgesia. Similarly, both WT and $Asic3^{-/-}$ mice showed transient hypersensitivity after a single LPC16:0 injection, but the chronic hyperalgesic changes in WT animals were significantly reduced in $Asic3^{-/-}$ mice after repeated LPC injections (FIG. 3K, right). In addition, LPC16:0 injection-induced pERK expression was reduced after pharmacological and genetic inhibition of ASIC3 (FIGS. 10F to 10I). WT and $Asic3^{-/-}$ mice were further exposed to RISS, followed by evaluation of behavioral responses (FIG. 3L). Both groups showed anxiety-like behaviors and transient hypersensitivity after RISS, but the chronic hyperalgesic changes in WT mice were significantly attenuated in $Asic3^{-/-}$ mice. Likewise, the ratio of pERK-positive DRG neurons induced by RISS was significantly decreased in $Asic3^{-/-}$ mice (FIGS. 10J and 10K).

In addition to catalytic synthesis by phospholipase $A_2$ during inflammatory reaction, LPCs can be produced as direct consequences of lipid oxidization under non-inflammatory conditions, via hydrolysis of oxidized PCs (ox-PCs) by platelet-activating factor acetylhydrolase (PAF-AH) or spontaneous deacylation of ox-PCs by ROS attack.

Figure 3N:
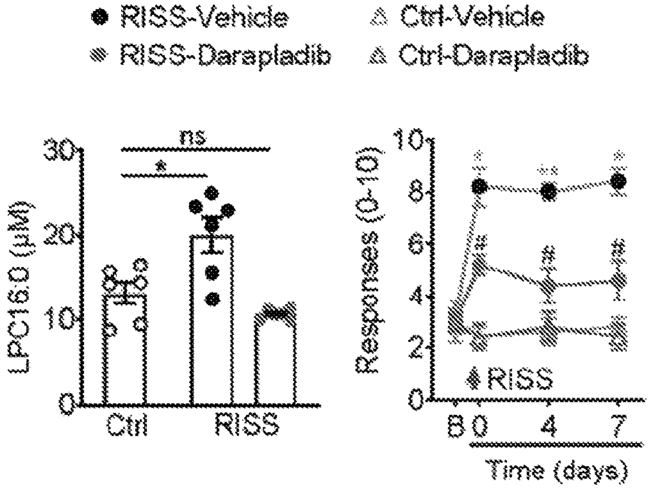
FIG. 3N shows the effect of darapladib (10 mg/kg bodyweight, i.p.) on serum level of LPC16:0 measured by selective reaction monitoring triple quadrupole mass spectrometry at P0 (n=6) (left graph), and the effect of darapladib on the RISS-induced chronic hyperalgesia as assessed by von Frey test (n=5) (right graph) (Both ANOVA).

To investigate whether PAF-AH participates in the LPC generation of the RISS model, darapladib (a selective PAF-AH inhibitor) was given once daily (10 mg/kg; i.p.) throughout the RISS procedure (FIG. 3M), followed by evaluation of LPC16:0 levels and pain behaviors. As compared with vehicle, darapladib significantly reduced LPC16:0 production after RISS and prevented the development of chronic hypersensitivity (FIG. 3N).

ROS also elicited LPC generation by spontaneous deacylation of ox-PCs under physiological conditions (37° C. and pH 7.4). In this noncatalytic pathway, using ROS scavengers to reduce the production of ox-PCs may be feasible for blocking LPC generation. To investigate the potential analgesic effect of ROS scavengers, antioxidants (N-acetylcysteine, 200 mg/kg; Tempol, 100 mg/kg; i.p.) were systemically administered throughout the RISS procedure (FIG. 3M).

Figure 3O:
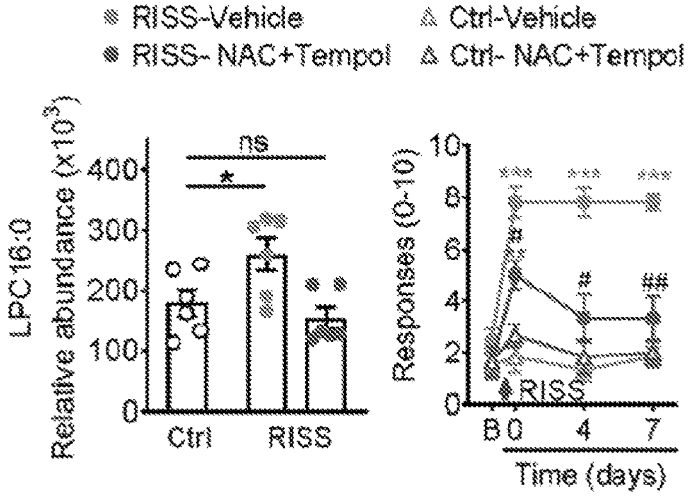

As shown in FIGS. 10L and 10M, antioxidants significantly reduced the oxidative stress of the serum (evaluated by MDA and $H_2O_2$ levels) and leukocytes in RISS mice. Antioxidants also effectively reduced serum LPC16:0 levels and rescued the development of chronic hyperalgesia (FIG. 3O). In vehicle-treated RISS mice, neither the LPC16:0 amount nor hypersensitivity development was affected.

Example 6: Increased LPC16:0 Expression in FM Patients Correlated with Pain Symptoms The mouse model revealed how LPC16:0 triggered long-lasting bilateral hyperalgesia after stress exposure. Patients with FM manifest chronic widespread pain with daily stressors as known triggers, and may also have excessive expression of these nociceptive oxidized lipids. To test this prediction, 31 FM patients and 30 age- and sex-matched healthy controls (HC) were examined, patient demographics and clinical evaluation were shown below in Table 4.

TABLE 4

A comparison of demographic data and clinical manifestation between patients with fibromyalgia (FM) and healthy controls (HC)

| Variable | Patients (n = 31) | Controls (n = 30) | p-value |
|---|---|---|---|
| Age | 46.39 ± 11.87 | 49.93 ± 14.47 | 0.299 |
| F/M | 28/3 | 27/3 | 0.966 |
| Verbal rating scale | 7.03 ± 2.39 | 0.70 ± 1.21 | <0.001* |
| Widespread pain index | 9.03 ± 4.50 | 0.57 ± 0.90 | <0.001* |
| | Symptom severity scale | | |
| Cognitive function | 1.48 ± 0.93 | 0.77 ± 0.68 | 0.001* |
| Fatigue | 2.00 ± 0.68 | 0.87 ± 0.43 | <0.001* |
| Waking up tired | 2.16 ± 0.82 | 0.70 ± 0.60 | <0.001* |
| Headache | 0.87 ± 0.34 | 0.43 ± 0.50 | <0.001* |
| GI symptoms | 0.55 ± 0.51 | 0.13 ± 0.35 | <0.001* |
| Depression | 0.65 ± 0.49 | 0.13 ± 0.35 | <0.001* |
| Sum | 7.71 ± 2.12 | 2.93 ± 1.76 | <0.001* |
| PSS-10 | 11.77 ± 4.37 | 21.52 ± 8.27 | <0.001* |
| | FIQR | | |
| Domain 1 | 27.35 ± 22.63 | 1.10 ± 2.40 | <0.001* |
| Domain 2 | 12.16 ± 6.19 | 0.27 ± 1.05 | <0.001* |
| Domain 3 | 63.06 ± 14.53 | 12.67 ± 10.14 | <0.001* |
| Score | 52.28 ± 17.66 | 6.97 ± 5.94 | <0.001* |

FIQR: the Revised Fibromyalgia Impact Questionnaire. PSS-10: Perceived Stress Scale. Values are mean ± standard deviation. Student's t test.
*statistical significance.

Figure 4A:
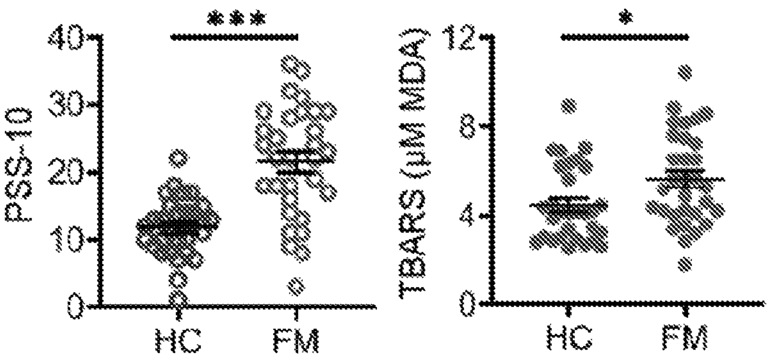
FIGS. 4A to 4F show that patients with fibromyalgia (FM) have higher perceived stress, increased oxidative stress and discriminative LPC expression in plasma.
Figure 4B:
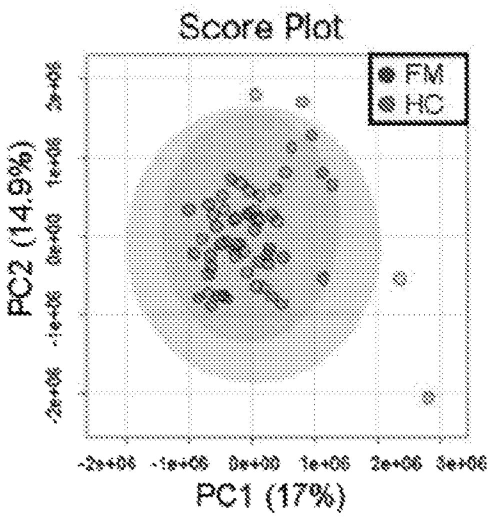

Patients with FM perceived higher psychological stress as assessed by the Perceived Stress Scale (PSS-10) and were under higher oxidative stress as assessed by MDA level than controls (FIG. 4A). A lipidomic analysis was used to compare the lipidomic expression between groups. Changes in peak intensity for all variables between patients and controls were compared by fold-change analysis, and lipids with significantly increased levels in the disease group were screened out (FIG. 4B, and Table 5). The identified lipids were mainly various LPCs as well as PCs and Cer.

TABLE 5

The fold changes in intensity of lipids increased significantly in patients with fibromyalgia as compared with healthy controls

| Lipid ID | Ion (m/z) | Adduct | Fold change FM/HC | p value |
|---|---|---|---|---|
| LPC 16:0 | 496.34 | M | 1.71 | 0.010 |
| LPC 16:1 | 494.32 | M | 1.13 | 0.036 |
| LPC 18:1 | 523.36 | $M + H^+$ | 2.22 | 0.000 |
| LPC 18:3 | 518.32 | M | 1.47 | 0.001 |
| LPC 20:1 | 550.39 | M | 1.60 | 0.000 |
| LPC 20:2 | 548.37 | M | 1.63 | 0.000 |
| LPC 20:4 | 544.34 | M | 1.84 | 0.005 |
| LPC 22:6 | 569.34 | $M+ H^+$ | 1.64 | 0.001 |
| Cer (d18:1/22:0) | 622.61 | M | 2.72 | 0.007 |
| PC 36:0 | 790.63 | M | 1.88 | 0.001 |
| PC 38:1 | 816.65 | M | 2.94 | 0.003 |

Fold changes were calculated by dividing the mean of peak intensity of each metabolite from fibromyalgia and healthy control groups (n = 31 and 30, respectively). Comparison was made using Mann-Whitney U test. FM: fibromyalgia. HC: healthy controls. LPC: lysophosphatidylcholine. Cer: ceramide. PC: phosphatidylcholine.

Figure 4C:
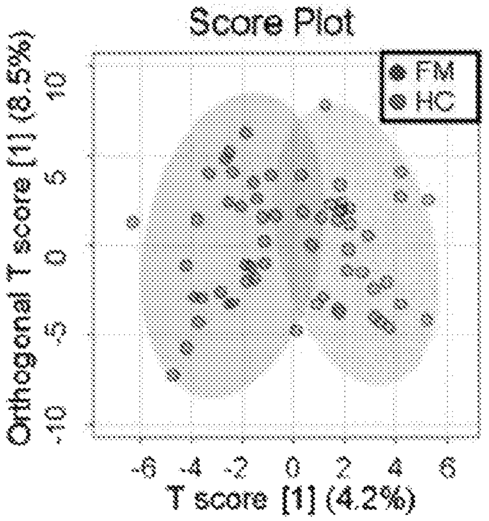
Figure 4D:
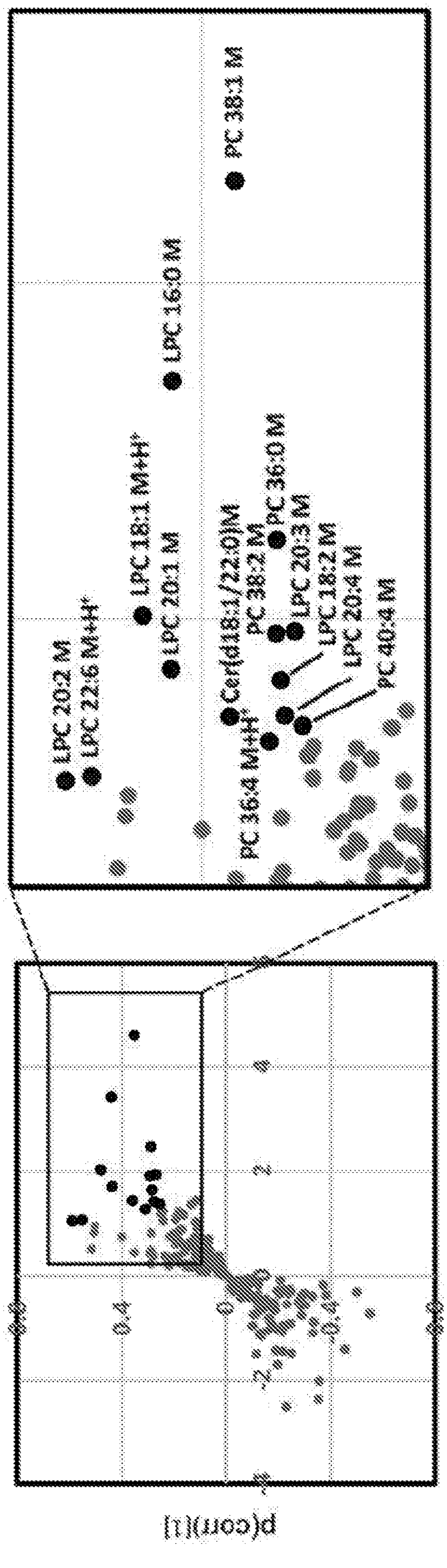
Figure 4E:
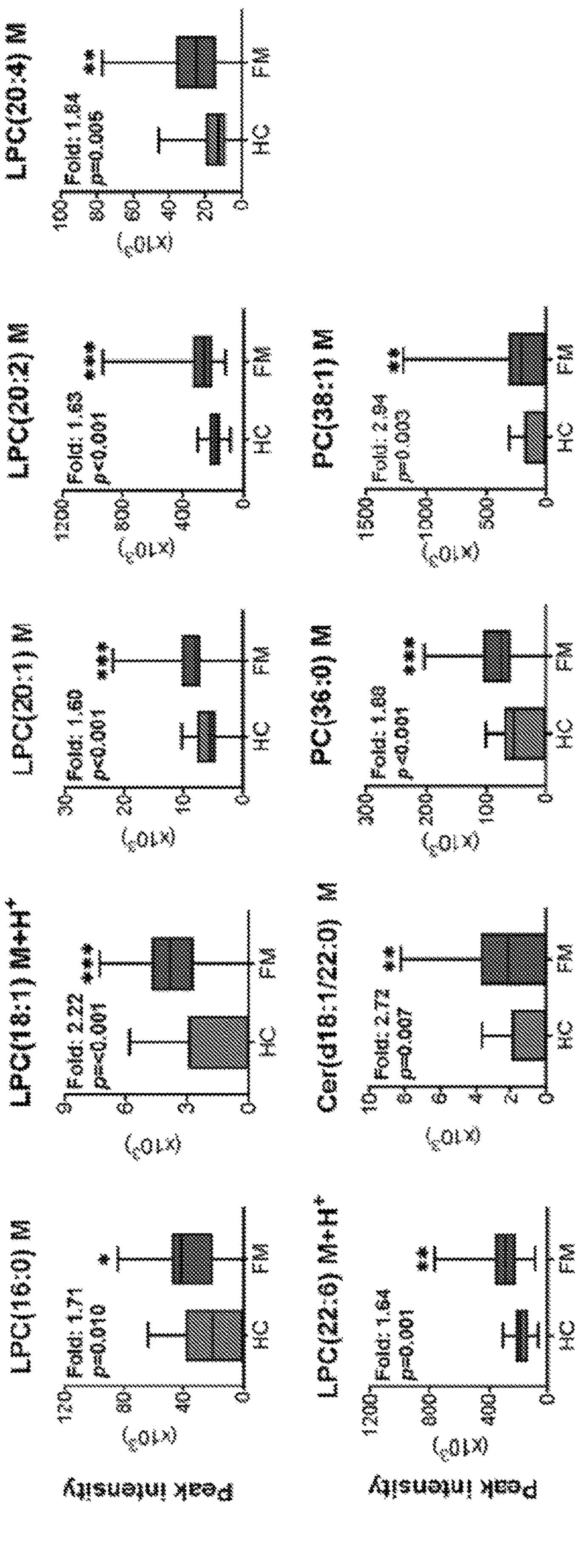
Figure 4F:
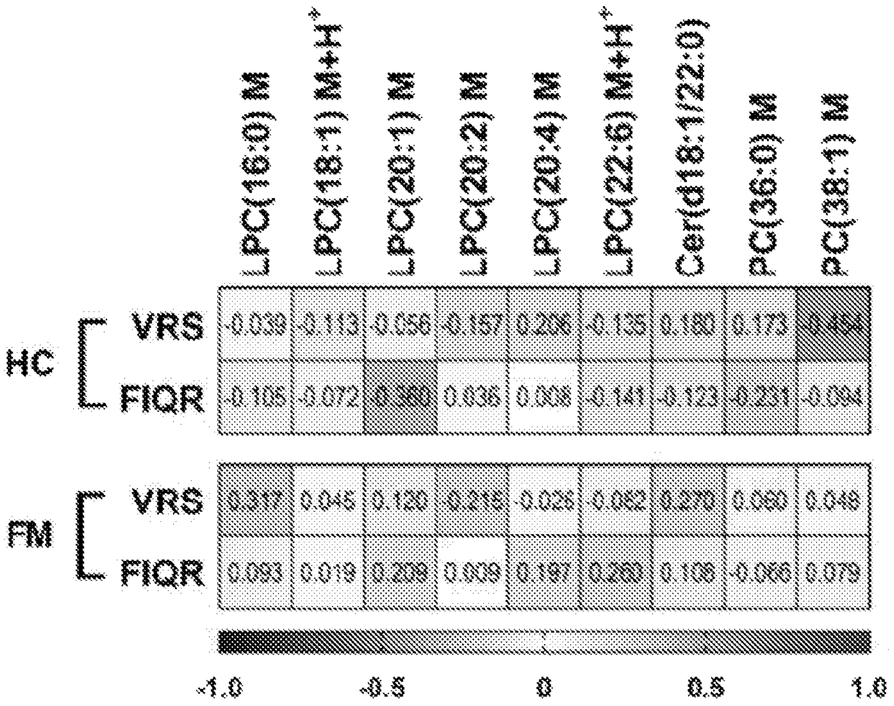

OPLS-DA was next used to identify the most discriminative metabolites for disease (FIGS. 4C and 4D). Among the 14 identified targets, 9 showed a significant increase in peak intensity based on fold-change analyses (FIG. 4E). It was evaluated whether the metabolite phenotypes were associated with clinical manifestations and found pain scores from verbal rating scale (VRS) and disease severity assessed by the Revised Fibromyalgia Impact Questionnaire (FIQR) correlated with the peak intensity expression of the identified lipids (FIG. 4F). No distinct positive correlation was found between lipid expression and symptoms in HCs, but modest correlation between LPC16:0 and pain intensity in patients with FM.

Figure 5A:
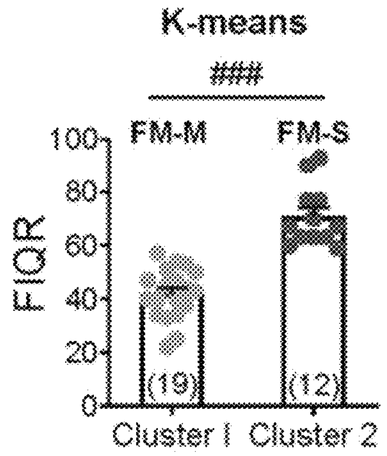
FIGS. 5A to 5F show that expression of LPC16:0 and other lipids are correlated with FM symptoms in patients with increased oxidative stress and high disease severity.

To investigate whether a metabolomic phenotypic difference exists within patients with different disease severity, K-means cluster analysis was used to further divide the cohort into two subgroups based on disease severity assessed by the FIQR (FIG. 5A). The resulting FM subgroups did not differ in sex or age, as shown in Table 6.

TABLE 6

Subgroup of patients with fibromyalgia based on the symptom severity of FIQR scores (K-means method)

| Variable | Cluster 1 | Cluster 2 | p-value |
|---|---|---|---|
| Description | FM-M | FM-S | |
| N | 19 | 12 | |
| Age | 43.5 ± 12.2 | 50.9 ± 10.2 | 0.152 |
| F/M | 18/1 | 10/2 | 0.296 |
| Verbal rating scale | 5.89 ± 2.00 | 7.67 ± 2.35 | 0.032* |
| Widespread pain index | 7.42 ± 3.70 | 11.58 ± 4.60 | 0.010* |
| PSS-10 | 20.68 ± 8.60 | 22.83 ± 7.90 | 0.490 |
| | FIQR | | |
| Domain 1 | 14.89 ± 16.46 | 47.08 ± 16.16 | <0.001* |
| Domain 2 | 8.21 ± 4.40 | 17.58 ± 2.94 | <0.001* |
| Domain 3 | 55.68 ± 8.64 | 74.75 ± 14.52 | <0.001* |
| Score | 41.49 ± 8.90 | 70.65 ± 11.46 | <0.001* |

FM-M: fibromyalgia with mild symptoms. FM-S: fibromyalgia with severe symptoms. FIQR: the Revised Fibromyalgia Impact Questionnaire. Values are mean ± standard deviation. Mann-Whitney U test. *statistical significance.

Figure 5B:
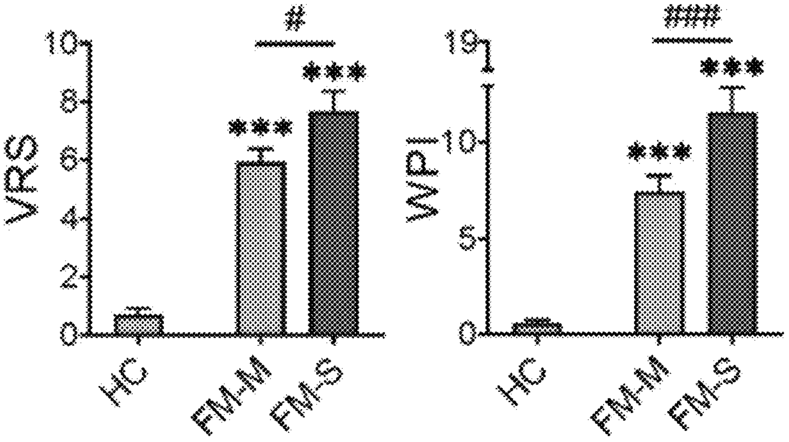
Figure 5C:
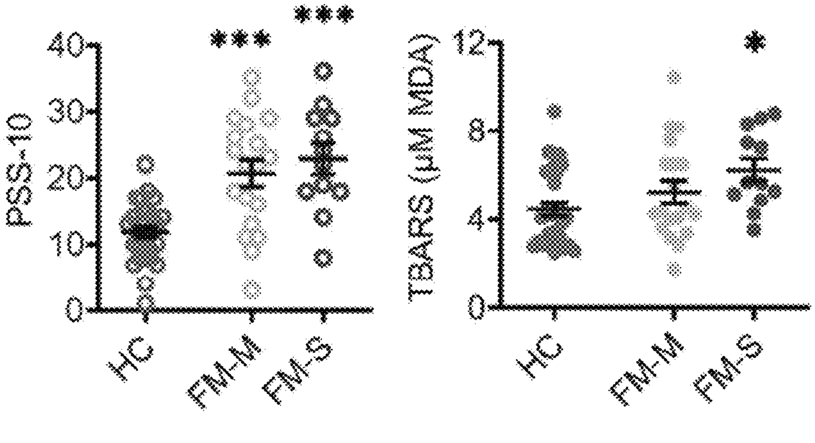
Figure 5D:
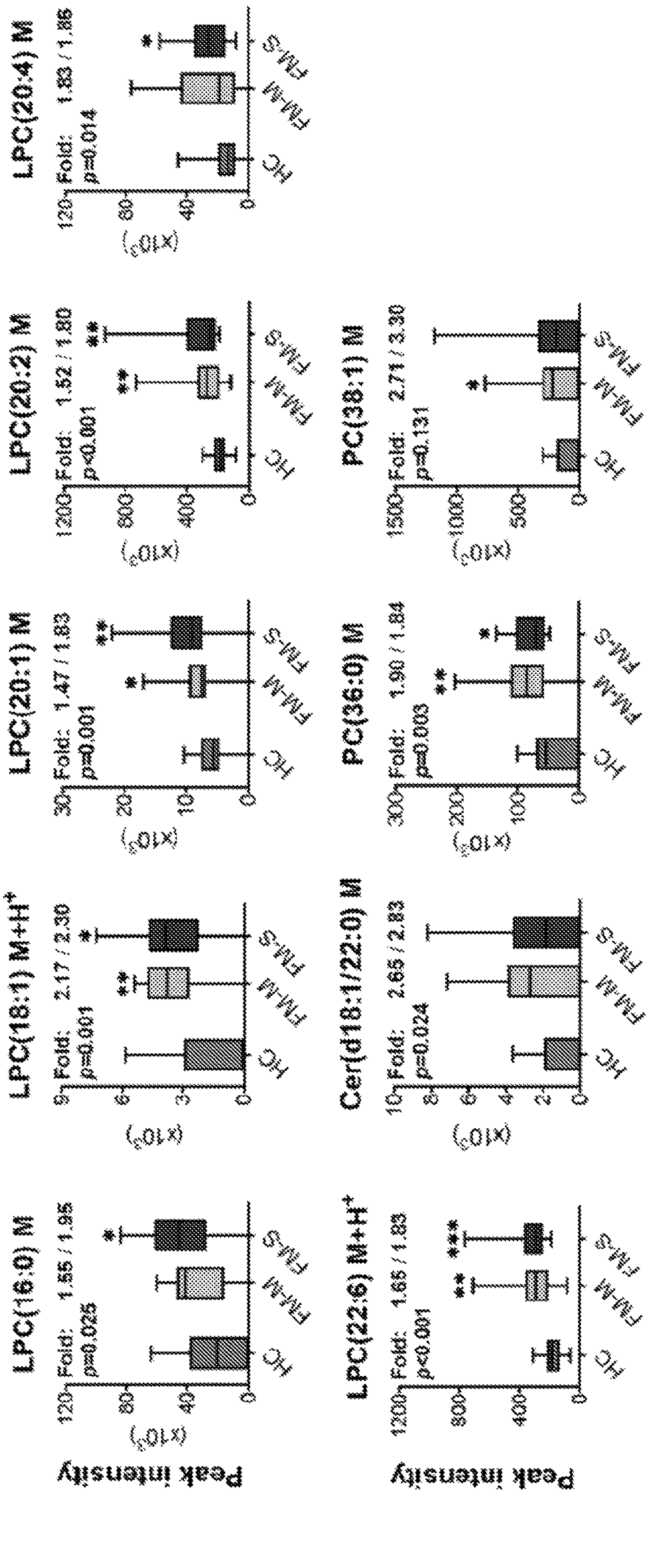

Overall FIQR scores were significantly higher in Cluster 2 than Cluster 1 (70.65±11.46 vs. 41.49±8.90), as were scores on all the FIQR domains (daily functions, overall impact, and symptom intensity). Moreover, Cluster 2 manifested significantly higher pain intensity and wider pain distribution than Cluster 1 (FIG. 5B). Hence, Cluster 2 was classified as the group with severe symptoms (FM-S), and cluster 1 with mild symptoms (FM-M). Of note, the FM-S group had significantly higher oxidative stress levels than HCs, with no significant difference observed between the FM-M and HC groups (FIG. 5C). Lipidomic expression of the identified lipids was next compared between subgroups (FIG. 5D). In accordance with the biological gradation of disease severity, the HC, FM-M and FM-S groups showed an increasing trend of peak intensity expression of all identified metabolites except PC36:0.

Figure 5E:
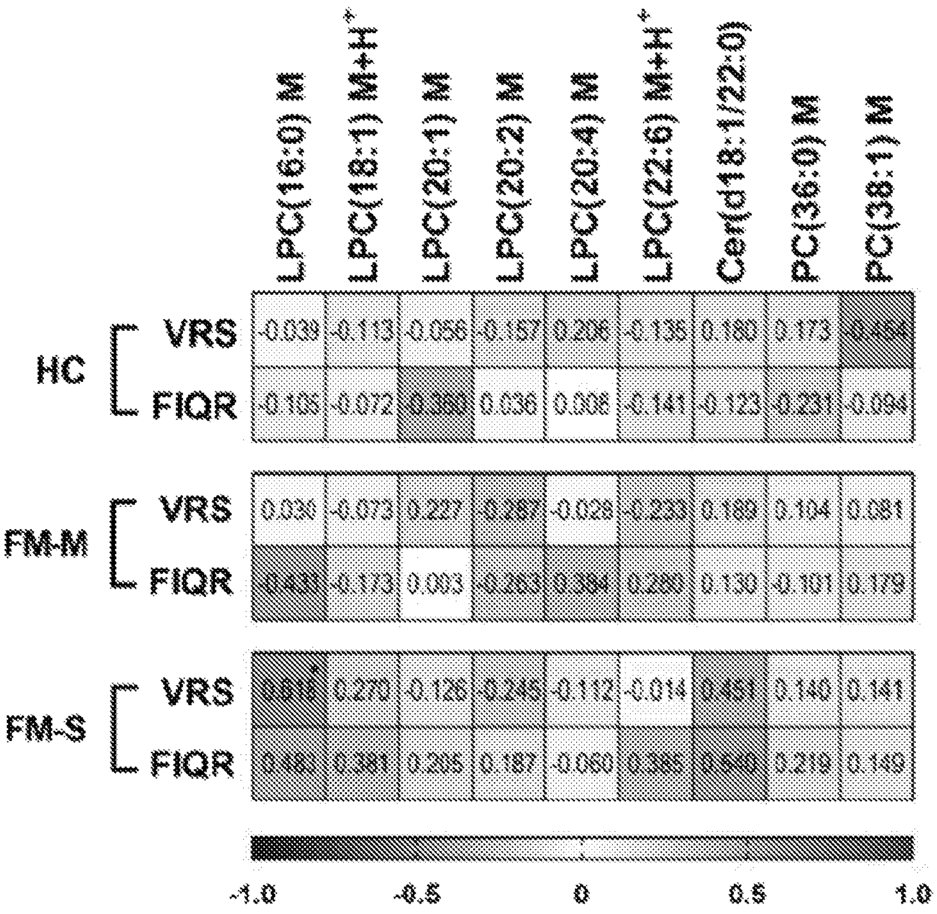
Figure 5F:
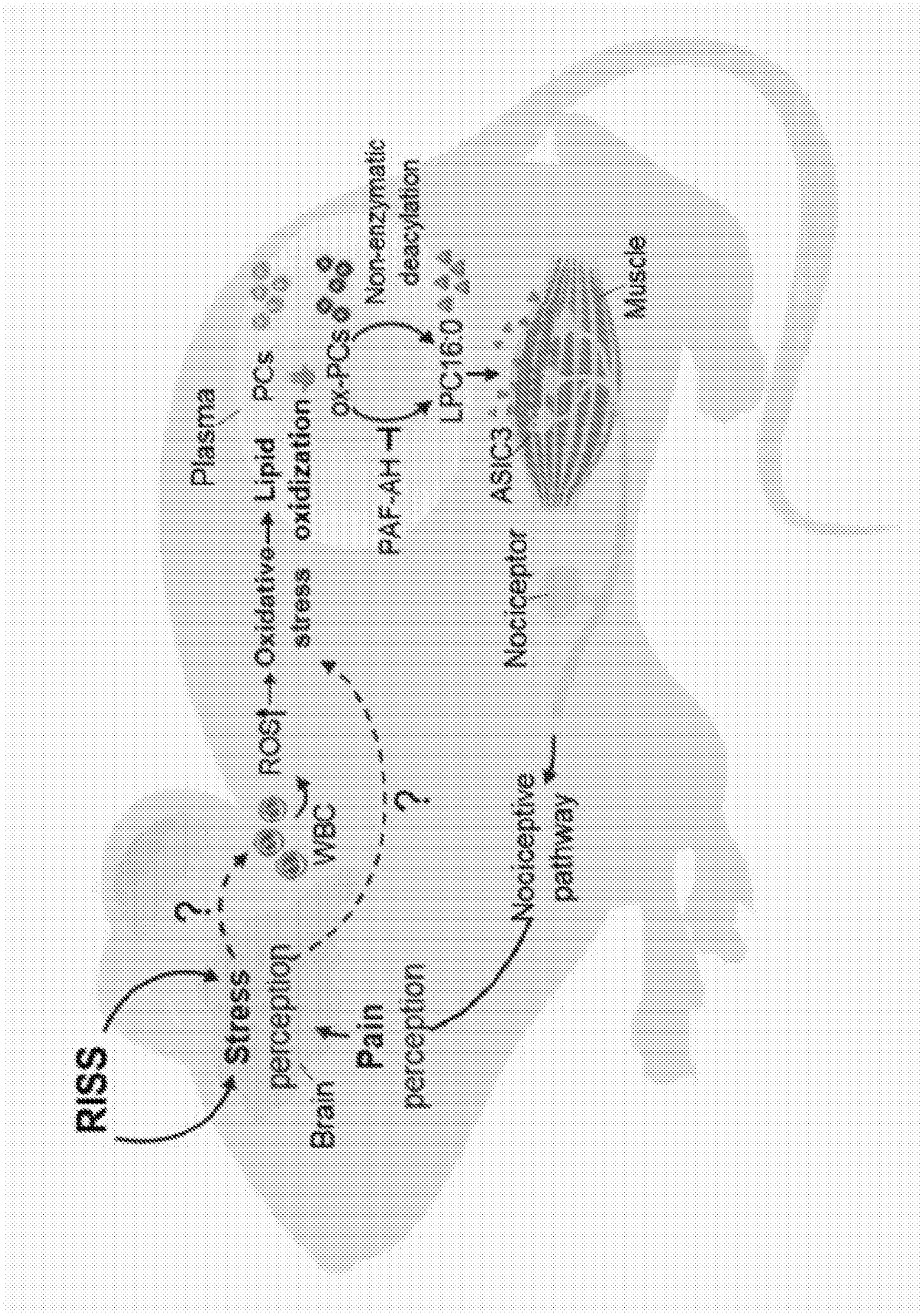

To evaluate whether the metabolite expression was associated with symptom severity and to compare the presentation of groups, the correlations between symptom measures (VRS and FIQR scores) and expression of peak intensity were assessed (FIG. 5E). In the FM-M group, LPC20:4 expression was positively correlated with FIQR score, with no correlation of other metabolites with clinical parameters. By comparison, the expression of several metabolites in the FM-S group showed fair correlation with clinical symptoms. FM-S patients with higher expression of LPC16:0, LPC18:1, LPC22:6, and Cer(d18:1/22:0) showed higher disease severity as indicated by FIQR score. Also, those with higher expression of LPC16:0 and Cer(d18:1/22:0) had higher VRS score. Moreover, the expression of LPC16:0 in FM-S patients was significantly correlated with VRS scores, which suggests that LPC16:0 might participate in the pain phenotype modulation (FIG. 5E). Taken together, excessive expression of LPCs can be detected by clinical lipidomics and is correlated with pain severity in FM patients with increased oxidative stress and symptom severity, as predicted by the mouse model. In this sense, the products of lipid oxidization, especially LPC16:0, might be a pathological signature and a therapeutic target for FM.

REFERENCES

1. Hassett, A. L. & Clauw, D. J. Does psychological stress cause chronic pain? *Psychiatr. Clin. North Am.* 34, 579-594, doi:10.1016/j.psc.2011.05.004 (2011).
2. Clauw, D. J. Fibromyalgia: an overview. *Am. J. Med.* 122, S3-S13, doi:10.1016/j.amjmed.2009.09.006 (2009).
3. Kivimaki, M. et al. Work stress and incidence of newly diagnosed fibromyalgia: prospective cohort study. *J. Psychosom. Res.* 57, 417-422, doi:10.1016/j.jpsychores.2003.10.013 (2004).
4. McBeth, J., Morris, S., Benjamin, S., Silman, A. J. & Macfarlane, G. J. Associations between adverse events in childhood and chronic widespread pain in adulthood: are they explained by differential recall? *J. Rheumatol.* 28, 2305-2309 (2001).
5. Aaron, L. A. et al. Perceived physical and emotional trauma as precipitating events in fibromyalgia. Associations with health care seeking and disability status but not pain severity. *Arthritis Rheum.* 40, 453-460 (1997).
6. Arnold, L. M. et al. Comorbidity of fibromyalgia and psychiatric disorders. *J. Clin. Psychiatry* 67, 1219-1225 (2006).
7. Sluka, K. A. & Clauw, D. J. Neurobiology of fibromyalgia and chronic widespread pain. *Neuroscience* 338, 114-129, doi:10.1016/j.neuroscience.2016.06.006 (2016).
8. Yunus, M. B. Central sensitivity syndromes: a new paradigm and group nosology for fibromyalgia and overlapping conditions, and the related issue of disease versus illness. *Semin. Arthritis Rheum.* 37, 339-352, doi:10.1016/j.semarthrit.2007.09.003 (2008).
9. Staud, R. & Smitherman, M. L. Peripheral and central sensitization in fibromyalgia: pathogenetic role. *Curr. Pain. Headache Rep.* 6, 259-266 (2002).
10. Simms, R. W. et al. Lack of association between fibromyalgia syndrome and abnormalities in muscle energy metabolism. *Arthritis Rheum.* 37, 794-800 (1994).
11. Taguchi, T. et al. Peripheral and spinal mechanisms of nociception in a rat reserpine-induced pain model. *Pain* 156, 415-427, doi:10.1097/01.j.pain.0000460334.49525.5e (2015).
12. Serra, J. et al. Hyperexcitable C nociceptors in fibromyalgia. *Ann. Neurol.* 75, 196-208, doi:10.1002/ana.24065 (2014).
13. DeSantana, J. M., da Cruz, K. M. & Sluka, K. A. Animal models of fibromyalgia. *Arthritis Res. Ther.* 15, 222, doi:10.1186/ar4402 (2013).
14. Khasar, S. G., Dina, O. A., Green, P. G. & Levine, J. D. Sound stress-induced long-term enhancement of mechanical hyperalgesia in rats is maintained by sympathoadrenal catecholamines. *J. Pain* 10, 1073-1077, doi:10.1016/j.jpain.2009.04.005 (2009).
15. Campos, A. C., Fogaca, M. V., Aguiar, D. C. & Guimaraes, F. S. Animal models of anxiety disorders and stress. *Rev. Bras. Psiquiatr.* 35 Suppl. 2, S101-111, doi:10.1590/1516-4446-2013-1139 (2013).
16. Reichling, D. B. & Levine, J. D. Critical role of nociceptor plasticity in chronic pain. *Trends Neurosci.* 32, 611-618, doi:10.1016/j.tins.2009.07.007 (2009).
17. Sluka, K. A. et al. Chronic hyperalgesia induced by repeated acid injections in muscle is abolished by the loss of ASIC3, but not ASIC1. *Pain* 106, 229-239 (2003).
18. Nishiyori, M. et al. Permanent relief from intermittent cold stress-induced fibromyalgia-like abnormal pain by repeated intrathecal administration of antidepressants. *Mol. Pain* 7, 69, doi:10.1186/1744-8069-7-69 (2011).
19. Tsujino, H. et al. Activating transcription factor 3 (ATF3) induction by axotomy in sensory and motoneurons: A novel neuronal marker of nerve injury. *Mol. Cell Neurosci.* 15, 170-182, doi:10.1006/mcne.1999.0814 (2000).
20. Dai, Y. et al. Phosphorylation of extracellular signal-regulated kinase in primary afferent neurons by noxious stimuli and its involvement in peripheral sensitization. *J. Neurosci.* 22, 7737-7745 (2002).
21. Epel, E. S. et al. Accelerated telomere shortening in response to life stress. *Proc. Natl. Acad. Sci. U.S.A.* 101, 17312-17315, doi:10.1073/pnas.0407162101 (2004).
22. Hagan, K. A., Wu, T., Rimm, E. B., Eliassen, A. H. & Okereke, O. I. Phobic Anxiety and Plasma Levels of Global Oxidative Stress in Women. *Eur. J. Psychiatry* 29, 7-20, doi:10.4321/S0213-61632015000100001 (2015).
23. Irie, M., Asami, S., Ikeda, M. & Kasai, H. Depressive state relates to female oxidative DNA damage via neutrophil activation. *Biochem. Biophys. Res. Commun.* 311, 1014-1018 (2003).
24. Bagis, S. et al. Free radicals and antioxidants in primary fibromyalgia: an oxidative stress disorder? *Rheumatol. Int.* 25, 188-190, doi:10.1007/s00296-003-0427-8 (2005).
25. Cordero, M. D. et al. Clinical symptoms in fibromyalgia are better associated to lipid peroxidation levels in blood mononuclear cells rather than in plasma. *PLoS One* 6, e26915, doi:10.1371/journal.pone.0026915 (2011).
26. Ayala, A., Munoz, M. F. & Arguelles, S. Lipid peroxidation: production, metabolism, and signaling mechanisms of malondialdehyde and 4-hydroxy-2-nonenal. *Oxid. Med. Cell Longev.* 2014, 360438, doi:10.1155/2014/360438 (2014).
27. Schieber, M. & Chandel, N. S. ROS function in redox signaling and oxidative stress. *Curr. Biol.* 24, R453-462, doi:10.1016/j.cub.2014.03.034 (2014).
28. Caboni, P. et al. Metabolomics analysis and modeling suggest a lysophosphocholines-PAF receptor interaction in fibromyalgia. *PLoS One* 9, e107626, doi:10.1371/journal.pone.0107626 (2014).
29. Inoue, M. et al. Lysophosphatidylcholine induces neuropathic pain through an action of autotaxin to generate lysophosphatidic acid. *Neuroscience* 152, 296-298, doi:10.1016/j.neuroscience.2007.12.041 (2008).
30. Marra, S., Ferru-Clement, R., Breuil, V., Delaunay, A. & Christin, M. Non-acidic activation of pain-related Acid-Sensing Ion Channel 3 by lipids. *EMBO* 35, 414-428, doi:10.15252/embj.201592335 (2016).
31. Inmmke, D. C. & McCleskey, E. W. Lactate enhances the acid-sensing $Na^+$ channel on ischemia-sensing neurons. *Nat. Neurosci.* 4, 869-870, doi:10.1038/nn0901-869 (2001).
32. Choi, J. et al. Lysophosphatidylcholine is generated by spontaneous deacylation of oxidized phospholipids. *Chem. Res. Toxicol.* 24, 111-118, doi:10.1021/tx100305b (2011).

33. Karabina, S. A. & Ninio, E. Plasma PAF-acetylhydrolase: an unfulfilled promise?*Biochim. Biophys. Acta* 1761, 1351-1358, doi:10.1016/j.bbalip.2006.05.008 (2006).

34. Subbaiah, P. V., Chen, C. H., Bagdade, J. D. & Albers, J. J. Substrate specificity of plasma lysolecithin acyltransferase and the molecular species of lecithin formed by the reaction. *J. Biol. Chem.* 260, 5308-5314 (1985).

35. Hodson, L., Skeaff, C. M. & Fielding, B. A. Fatty acid composition of adipose tissue and blood in humans and its use as a biomarker of dietary intake. *Prog. Lipid Res.* 47, 348-380, doi:10.1016/j.plipres.2008.03.003 (2008).

36. Molliver, D. C. et al. ASIC3, an acid-sensing ion channel, is expressed in metaboreceptive sensory neurons. *Mol. Pain* 1, 35, doi:10.1186/1744-8069-1-35 (2005).

37. McIntyre, T. M., Prescott, S. M. & Stafforini, D. M. The emerging roles of PAF acetylhydrolase. *J. Lipid Res.* 50 Suppl., S255-259, doi:10.1194/jlr.R800024-JLR200 (2009).

38. Chrousos, G. P. & Gold, P. W. The concepts of stress and stress system disorders. Overview of physical and behavioral homeostasis. *JAMA* 267, 1244-1252 (1992).

39. Salim, S. Oxidative stress and psychological disorders. *Curr. Neuropharmacol.* 12, 140-147, doi:10.2174/1570159X11666131120230309 (2014).

40. Cordero, M. D. et al. Oxidative stress and mitochondrial dysfunction in fibromyalgia. *Neuro. Endocrinol. Lett.* 31, 169-173 (2010).

41. Council, N. R. *Guide for the Care and Use of Laboratory Animals: Eighth Edition*. (The National Academies Press, 2011).

42. Chen, C. C. et al. A role for ASIC3 in the modulation of high-intensity pain stimuli. *Proc. Natl. Acad. Sci. U.S.A.* 99, 8992-8997, doi:10.1073/pnas.122245999 (2002).

43. Singh, V. B., Corley, K. C., Phan, T. H. & Boadle-Biber, M. C. Increases in the activity of tryptophan hydroxylase from rat cortex and midbrain in response to acute or repeated sound stress are blocked by adrenalectomy and restored by dexamethasone treatment. *Brain Res.* 516, 66-76 (1990).

44. Sluka, K. A., Kalra, A. & Moore, S. A. Unilateral intramuscular injections of acidic saline produce a bilateral, long-lasting hyperalgesia. *Muscle Nerve* 24, 37-46 (2001).

45. Hargreaves, K., Dubner, R., Brown, F., Flores, C. & Joris, J. A new and sensitive method for measuring thermal nociception in cutaneous hyperalgesia. *Pain* 32, 77-88 (1988).

46. Gregory, N. S., Brito, R. G., Fusaro, M. C. & Sluka, K. A. ASIC3 is required for development of fatigue-induced hyperalgesia. *Mol. Neurobiol.* 53, 1020-1030, doi:10.1007/s12035-014-9055-4 (2016).

47. Yokoyama, T., Lisi, T. L., Moore, S. A. & Sluka, K. A. Muscle fatigue increases the probability of developing hyperalgesia in mice. *J. Pain* 8, 692-699, doi:10.1016/j.jpain.2007.05.008 (2007).

48. Beiser, T., Numa, R., Kohen, R. & Yaka, R. Chronic treatment with Tempol during acquisition or withdrawal from CPP abolishes the expression of cocaine reward and diminishes oxidative damage. *Sci. Rep.* 7, 11162, doi:10.1038/s41598-017-11511-7 (2017).

49. Ohmichi, Y. et al. Two-week cast immobilization induced chronic widespread hyperalgesia in rats. *Eur. J. Pain* 16, 338-348, doi:10.1002/j.1532-2149.2011.00026.x (2012).

50. Li, J. et al. N-acetyl-cysteine attenuates neuropathic pain by suppressing matrix metalloproteinases. *Pain* 157, 1711-1723, doi:10.1097/j.pain.0000000000000575 (2016).

51. Shi, S. Y. et al. DJ-1 links muscle ROS production with metabolic reprogramming and systemic energy homeostasis in mice. *Nat. Commun.* 6, 7415, doi:10.1038/ncomms8415 (2015).

52. Rammal, H., Bouayed, J., Younos, C. & Soulimani, R. The impact of high anxiety level on the oxidative status of mouse peripheral blood lymphocytes, granulocytes and monocytes. *Eur. J. Pharmacol.* 589, 173-175, doi:10.1016/j.ejphar.2008.06.053 (2008).

53. Eruslanov, E. & Kusmartsev, S. Identification of ROS using oxidized DCFDA and flow-cytometry. *Methods Mol. Biol.* 594, 57-72, doi:10.1007/978-1-60761-411-1_4 (2010).

54. Hu, P. & McLachlan, E. M. Selective reactions of cutaneous and muscle afferent neurons to peripheral nerve transection in rats. *J. Neurosci.* 23, 10559-10567 (2003).

55. Bacskai, T., Rusznak, Z., Paxinos, G. & Watson, C. Musculotopic organization of the motor neurons supplying the mouse hindlimb muscles: a quantitative study using Fluoro-Gold retrograde tracing. *Brain Struct. Funct.* 219, 303-321, doi:10.1007/s00429-012-0501-7 (2014).

56. Ho, T. J., Kuo, C. H., Wang, S. Y., Chen, G. Y. & Tseng, Y. J. True ion pick (TIPick): a denoising and peak picking algorithm to extract ion signals from liquid chromatography/mass spectrometry data. *J. Mass Spectrom.* 48, 234-242, doi:10.1002/jms.3154 (2013).

57. Xia, J. & Wishart, D. S. Web-based inference of biological patterns, functions and pathways from metabolomic data using MetaboAnalyst. *Nat. Protoc.* 6, 743-760, doi:10.1038/nprot.2011.319 (2011).

58. Caboni P, Liori B, Kumar A. et al. Metabolomics analysis and modeling suggest a lysophosphocholines-PAF receptor interaction in fibromyalgia. *PLoS One.* 2014 Sep. 19; 9(9):e107626.

59. Tzellos T. G., Toulis K. A., Goulis D. G. et al. Gabapentin and pregabalin in the treatment of fibromyalgia: a systematic review and a meta-analysis. *J. Clin. Pharm. Ther.* 2010; 35(6):639-656.

60. Arnold L. M., Clauw D. J., Wohlreich M. M., et al. Efficacy of duloxetine in patients with fibromyalgia: pooled analysis of 4 placebo-controlled clinical trials. *Prim. Care Companion J. Clin. Psychiatry.* 2009:11(5): 237-244.

61. Geisser M. E., Palmer R. H., Gendreau R. M., Wang Y., Clauw D. J. A pooled analysis of 2 randomized, double-blind, placebo-controlled trials of milnacipran monotherapy in the treatment of fibromyalgia. *Pain Pract.* 2011; 11(2):120-131.

62. Harris R. E. & Clauw D. J. Newer Treatments for Fibromyalgia Syndrome *Ther. Clin. Risk Manag.* 2008 December; 4(6):1331-42.

63. Malin K. & Littlejohn G. O. Stress modulates key psychological processes and characteristic symptoms in females with fibromyalgia. *Clin. Exp. Rheumatol.* 2013 November-December; 31(6 Suppl. 79): S64-71. Epub. 2013 Oct. 21.

64. Yunus M. B. Central Sensitivity Syndromes: A new paradigm and group nosology for fibromyalgia and overlapping conditions, and the related issue of disease versus illness. Semin. *Arthritis Rheum.* 2008 June; 37(6):339-52.

65. Viola-Saltzman M. & Watson N. F. et al. High prevalence of restless legs syndrome among patients with fibromyalgia: a controlled cross-sectional study. *J. Clin. Sleep Med.* 2010 Oct. 15; 6(5): 423-427.

66. Hoogwout S. J. & Paananen M. V. et al. Musculoskeletal pain is associated with restless legs syndrome in young adults. BMC Musculoskeletal Disorders 16 (October, 2015): p. 294-294.

67. Zhua X. Y. & Wua T. T. Clinical features and subtypes of restless legs syndrome in Chinese population: a study of 359 patients. *Sleep Medicine* 59 (2019): p. 15-23.

What is claimed is:

1. A method for treating pain or a pain disorder comprising administering to a subject in need thereof an effective amount of an inhibitor of lysophosphatidylcholine (LPC) generation, wherein the pain or the pain disorder includes fibromyalgia, primary headache, migraine, tension type headache, restless leg syndrome (RLS), muscular discomfort, limb soreness, lower back pain, cancer pain, arthritis pain or psychogenic pain, or the pain is caused by an irritable bowel syndrome, a bladder pain syndrome or a temporomandibular disorder; and wherein the inhibitor of LPC generation is:

a pyrimidine-4-one derivative selected from N-[2-(diethylamino)ethyl]-2-{2-[(4-fluorobenzyl)sulfanyl]-4-oxo-4,5,6,7-tetrahydro-1H-cyclopenta[d]pyrimidin-1-yl}-N-{[4'-(trifluoromethyl)biphenyl-4-yl]methyl}acetamide

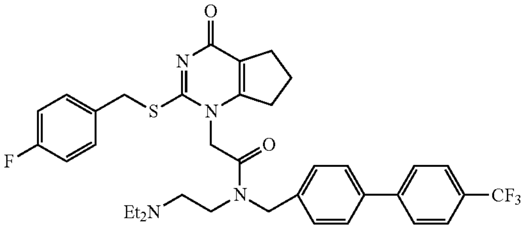

or

2-[2-[(2,3-difluorophenyl)methylsulfanyl]-4-oxoquinolin-1-yl]-N-[1-(2-methoxyethyl)piperidin-4-yl]-N-[4-[4-(trifluoromethyl)phenyl]phenyl]methyl]acetamide

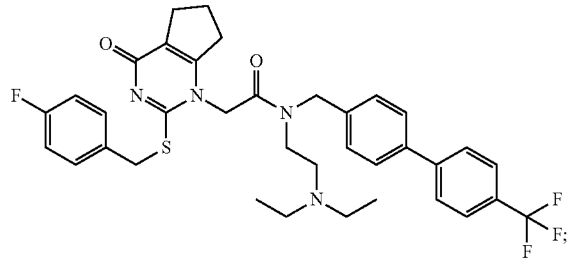

and an antioxidant selected from the group consisting of ascorbic acid, Na-ascorbate, L-cysteine, N-acetylcysteine (NAC), glutathione (GSH), Na2-EDTA, Na2-EDTA-Ca, and sodium bisulfite.

2. The method of claim 1, wherein administration of the inhibitor of LPC generation results in reduction of hydrolysis or deacylation of oxidized phosphatidylcholine in the subject.

3. The method of claim 1, wherein administration of the inhibitor of LPC generation results in reduction of synthesis of LPC16:0.

4. The method of claim 1, wherein the pain or the pain disorder is stress-related pain.

5. The method of claim 1, wherein administration of the inhibitor of LPC generation results in blocking progression of the pain or the pain disorder and provides a long term anti-nociceptive effect.

* * * * *